(12) United States Patent
Terrett et al.

(10) Patent No.: US 10,081,682 B2
(45) Date of Patent: Sep. 25, 2018

(54) CONJUGATED ANTIBODIES AGAINST LY75 FOR THE TREATMENT OF CANCER

(71) Applicant: OXFORD BIOTHERAPEUTICS LTD, Milton Park, Abingdon Oxfordshire (GB)

(72) Inventors: Jonathan Alexander Terrett, San Jose, CA (US); James Edward Ackroyd, Abigdon (GB)

(73) Assignee: Oxford Bio Therapeutics Ltd., Abington, Oxfordshire (GB)

( * ) Notice: Subject to any disclaimer, the term of this patent is extended or adjusted under 35 U.S.C. 154(b) by 116 days.

(21) Appl. No.: 15/028,666

(22) PCT Filed: Oct. 10, 2014

(86) PCT No.: PCT/GB2014/053057
§ 371 (c)(1),
(2) Date: Apr. 11, 2016

(87) PCT Pub. No.: WO2015/052537
PCT Pub. Date: Apr. 16, 2015

(65) Prior Publication Data
US 2016/0257760 A1 Sep. 8, 2016

Related U.S. Application Data

(60) Provisional application No. 61/890,104, filed on Oct. 11, 2013, provisional application No. 61/890,098, filed on Oct. 11, 2013.

(51) Int. Cl.
| | |
|---|---|
| *C07K 16/30* | (2006.01) |
| *C07K 16/28* | (2006.01) |
| *A61K 47/48* | (2006.01) |
| *A61K 47/68* | (2017.01) |
| *A61K 39/00* | (2006.01) |

(52) U.S. Cl.
CPC ............. *C07K 16/30* (2013.01); *A61K 47/68* (2017.08); *A61K 47/6803* (2017.08); *A61K 47/6849* (2017.08); *A61K 47/6851* (2017.08); *A61K 47/6855* (2017.08); *A61K 47/6857* (2017.08); *A61K 47/6859* (2017.08); *A61K 47/6861* (2017.08); *A61K 47/6863* (2017.08); *A61K 47/6865* (2017.08); *A61K 47/6867* (2017.08); *A61K 47/6869* (2017.08); *C07K 16/2851* (2013.01); *C07K 16/303* (2013.01); *C07K 16/3015* (2013.01); *C07K 16/3023* (2013.01); *C07K 16/3038* (2013.01); *C07K 16/3046* (2013.01); *C07K 16/3053* (2013.01); *C07K 16/3061* (2013.01); *C07K 16/3069* (2013.01); *A61K 2039/505* (2013.01); *C07K 2317/21* (2013.01); *C07K 2317/31* (2013.01); *C07K 2317/34* (2013.01); *C07K 2317/56* (2013.01); *C07K 2317/565* (2013.01); *C07K 2317/732* (2013.01); *C07K 2317/734* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,595,756 A | 1/1997 | Bally et al. | |
| 6,024,956 A * | 2/2000 | Matsushima | C07K 16/244 424/130.1 |
| 6,432,666 B1 | 8/2002 | Hart | |
| 6,900,016 B1 | 5/2005 | Venter et al. | |
| 7,608,413 B1 | 10/2009 | Joseloff et al. | |
| 7,842,466 B1 | 11/2010 | Kim et al. | |
| 7,998,689 B2 | 8/2011 | Joseloff et al. | |
| 8,147,835 B2 | 4/2012 | Ledbetter et al. | |
| 8,168,586 B1 | 5/2012 | Fang et al. | |
| 8,236,318 B2 | 8/2012 | Keler et al. | |
| 9,200,055 B2 | 12/2015 | Rohlff et al. | |
| 2004/0157307 A1 | 8/2004 | Harris | |
| 2004/0258688 A1 | 12/2004 | Hawiger et al. | |
| 2005/0186612 A1 | 8/2005 | Hart | |
| 2006/0281672 A1 | 12/2006 | Hart | |
| 2009/0087445 A1 | 4/2009 | Freund et al. | |
| 2009/0175880 A1 | 7/2009 | Keler et al. | |
| 2015/0297743 A1 | 10/2015 | Ackroyd | |

(Continued)

FOREIGN PATENT DOCUMENTS

| | | |
|---|---|---|
| AU | 2013201417 A1 | 4/2013 |
| CN | 103044552 A | 7/2013 |
| EP | 2067486 A1 | 6/2009 |

(Continued)

OTHER PUBLICATIONS

Lambert et al (Current Opinion in Pharmacology, 2005, vol. 5, pp. 543-549).*
Chames et al, British Journal of Phamacology, 2009, vol. 157, pp. 220-233.*
Abstract of Bressan (Cancer Research, 2017, vol. 77, No. 13, supplement, abstract No. 3646).*
Scott et al, Nature Reviews Cancer, 2012, vol. 12, pp. 278-287.*
U.S. Appl. No. 60/903,509, filed Feb. 26, 2007, Expired.
U.S. Appl. No. 60/903,510, filed Feb. 26, 2007, Expired.
PCT/GB2008/05012, filed Feb. 26, 2008, WO 2008/104806, Expired.
PCT/GB2013/52899, filed Feb. 26, 2008, WO 2014/072700, Expired.
U.S. Appl. No. 12/547,736, filed Aug. 26, 2009, now U.S. Pat. No. 9,200,055, Issued.

(Continued)

*Primary Examiner* — Karen A Canella
(74) *Attorney, Agent, or Firm* — Alston & Bird

(57) ABSTRACT

The invention provides antibodies which bind to LY75. Nucleic acid molecules encoding the antibodies, expression vectors, host cells and methods for expressing the antibodies are also provided. The antibodies may be used for the treatment of cancer, including pancreatic cancer, ovarian cancer, breast cancer, colorectal cancer, esophageal cancer, skin cancer, thyroid cancer, lung cancer, bladder cancer, multiple myeloma and lymphoma.

21 Claims, 29 Drawing Sheets

Specification includes a Sequence Listing.

(56) References Cited

U.S. PATENT DOCUMENTS

2016/0175437 A1 6/2016 Rohlff et al.

FOREIGN PATENT DOCUMENTS

| EP | 2159291 A1 | 3/2010 |
|---|---|---|
| EP | 2444409 A2 | 4/2012 |
| EP | 2520935 A2 | 11/2012 |
| WO | WO 96/023882 A1 | 8/1996 |
| WO | WO 97/045449 A1 | 12/1997 |
| WO | WO 01/057251 A2 | 8/2001 |
| WO | WO 02/102235 A2 | 12/2002 |
| WO | WO 03/042661 A2 | 5/2003 |
| WO | WO 03/080640 A1 | 10/2003 |
| WO | WO 03/083069 A2 | 10/2003 |
| WO | WO 04/019978 A1 | 3/2004 |
| WO | WO 04/024097 A2 | 3/2004 |
| WO | WO 04/035619 A1 | 4/2004 |
| WO | WO 04/053138 A1 | 6/2004 |
| WO | WO 05/016952 A2 | 2/2005 |
| WO | WO 05/016962 A2 | 2/2005 |
| WO | WO 05/017148 A1 | 2/2005 |
| WO | WO 05/019258 A2 | 3/2005 |
| WO | WO 05/037989 A2 | 4/2005 |
| WO | WO 05/067667 A2 | 7/2005 |
| WO | WO 06/093524 A2 | 9/2006 |
| WO | WO 07/030531 A2 | 3/2007 |
| WO | WO 07/141280 A2 | 12/2007 |
| WO | WO 08/016356 A2 | 2/2008 |
| WO | WO 08/021290 A2 | 2/2008 |
| WO | WO 08/104804 A2 | 9/2008 |
| WO | WO 08/104806 A2 | 9/2008 |
| WO | WO 09/061996 A2 | 5/2009 |
| WO | WO 11/011677 A2 | 1/2011 |
| WO | WO 11/044452 A2 | 4/2011 |
| WO | WO 12/122396 A1 | 9/2012 |
| WO | WO 15/052537 A1 | 4/2015 |

OTHER PUBLICATIONS

U.S. Appl. No. 61/890,098, filed Oct. 11, 2013, Expired.
U.S. Appl. No. 61/890,104, filed Oct. 11, 2013, Expired.
PCT/GB2014/05305, filed Oct. 10, 2014, WO 2015/052537, Expired.
U.S. Appl. No. 14/440,483, filed May 4, 2015, US-2015-0297743, Pending.
U.S. Appl. No. 14/950,087, filed Nov. 24, 2015, US-2016-0175437, Pending.
"Lectins," FluoProbes / Interchim, 2 pages, (2011). Author Unknown.
"Chronic Lymphocyfic Leukemia/ Small Lymphocytic Lymphoma (CLL/ALL)," Lymphoma Research Foundation, 3 pages, (2012). Author unknown.
Badiee et al., "Enhanced delivery of immunoliposomes to human dendritic cells by targeting the multilectin receptor DEC-2005," Vaccine, 25:4757-4766, (2007).
Birkholz et al., "Targeting of DEC-205 on human dendritic cells results in efficient MHC class II-restricted antigen presentation," Blood, 11:2277-2285., (2010).
Brown et al., "Tolerance to single, but no multiple, amino acid replacements in antibody VH CDR2," Journal of Immunology, 156(9):3285-3291, (1996).
Charalambous et al., "Dendritic cell targeting of survivin protein in a xenogeneic form elicits strong CD4+ T cell immunity to mouse survivin," J. Immunol., 177(12):8410-8421, (2006).
Chari, "Targeted Cancer Therapy: Conferiring Specifity to Cytotoxic Drugs," Accounts of Chemical Research, 41(1):98-107, (2008).
Gibbs et al., "Nanobodies," Scientific American Maganize, pp. 79-83, (2005).
Giridhar et al., "Interleukin-6 receptor enhances early colonization of the murine omentum by upregulation of a mannose family receptor, LY75, in ovarian tumor cells," Clin Exp Metastasis, 28:887-897, (2011).

Guo et al., "A Monoclonal Antibody to the DEC-205 Endocytosis Receptor on Human Dendritic Cells," Hum. Immunol., 61(8):729-738, (2000).
Heppner et al., "Tumor heterogeneity: biological implications and therapeutic consequences," Cancer Metastasis Review, 2:5-23; (1983).
Holt et al., "Domain antibodies: proteins for therapy," Trends in biotechnology, 21(11):484-490, (2003).
Jain "Barriers to drug delivery in solid tumors," Scientific American, pp. 58-65, (1994).
Johnson et al., "Inhibition of melanoma growth by targeting of antigen to dendritic cells via an anti-DEC-205 single-chain fragment variable molecule," Clin Cncer Res, 14:8169-8177, (2008).
Kato et al., "Expression of human DEC-205 (CD205) multilectin receptor on leukocytes," Int. Immunol., 18(6):857-869, (2006).
Kuppers "Hodgkin lymphoma," Atlas of Genetics and Cytogenetics in Oncology and Haematology, 15, 527-528, (2011). Published in Atlas Database: Sep. 2010.
Lollini et al., "Vaccines for tumour preventions," Nature Review Cancer, 6(3):204-216, (2006).
Mahnke et al., "Targeting of antigens to activated dendritic cells in vivo cures metastatic melanoma in mice," Cancer Res, 65:7007-7012, (2005).
Nchinda et al., "The efficacy of DNA vaccination is enhanced in mice by targeting the encoded protein to dendritic cells," J. Clin. Invest., 118(4):1427-1436, (2008).
Reddy "Chronic lymphocytic leukaemia (CLL)," Atlas of Genetics and Cytogenetics in Oncology and Haematology, 9:238-240, (2005).
Schwingshackl et al., "Distribution and maturation of skin dendritic cell subsets in two forms of cutaneous T-cell lymphoma: mycosis fungoides and Sezary Syndrome," ACTA Dermato-Venereologica, 92:269-275, (2012). Accepted Jun. 8, 2011.
Silverman et al., "Multivalent avimer proteins evolved by exon shuffling of a family of human receptor domains," Nature Biotechnology, 23(12):1556-1561, (2005).
Tubuly et al., "Differential expression of gp200-MR6 molecule in benign hyperplasia and down-regulation in invasive carcinoma of the breast," Bri J Can, 74:1005-1011, (1996).
Tubuly et al., "Inhibition of growth and enhancement of differentiation of colorectal carcinoma cell lines by MAb MR6 and IL-4," Int. J. Cancer, 71:605-611, (1997).
Vajdos et al., "Comprehensive Functional Maps of the Antigen binding Site of an Anti-ErbB2 Antibody Obtained with Shotgun Scanning Mutagenesis," Journal of Molecular Biology, 320(2):415-428, (2002).
U.S. Appl. No. 12/547,736, Non-Final Office Action dated Jul. 10, 2012.
U.S. Appl. No. 12/547,736, Non-Final Office Action dated Feb. 14, 2014.
U.S. Appl. No. 12/547,736, Non-Final Office Action dated Mar. 2, 2015.
U.S. Appl. No. 12/547,736, Non-Final Office Action dated Jul. 22, 2014.
U.S. Appl. No. 12/547,736, Non-Final Office Action dated Dec. 7, 2011.
U.S. Appl. No. 12/547,736, Notice of Allowance dated Jul. 20, 2015.
U.S. Appl. No. 12/547,736, Requirement for Restriction/Election dated Sep. 22, 2011.
U.S. Appl. No. 14/440,483, Non-Final Office Action dated Jul. 13, 2016.
U.S. Appl. No. 14/440,483, Requirement for Restriction/Election dated May 12, 2016.
WIPO Application No. PCT/GB2008/050127, PCT International Preliminary Report on Patentability dated Aug. 26, 2009.
WIPO Application No. PCT/GB2008/050127, PCT International Search Report dated Jan. 21, 2009.
WIPO Application No. PCT/GB2008/050127, PCT Written Opinion of the International Searching Authority dated Jan. 21, 2009.
WIPO Application No. PCT/GB2013/052899, PCT Written Opinion of the International Searching Authority dated Feb. 7, 2014.
WIPO Application No. PCT/GB2013/052899, PCT International Preliminary Report on Patentability dated May 12, 2015.

(56) References Cited

OTHER PUBLICATIONS

WIPO Application No. PCT/GB2013/052899, PCT International Search Report dated Feb. 7, 2014.
WIPO Application No. PCT/GB2014/053057, PCT International Preliminary Report on Patentability dated Apr. 12, 2016.
WIPO Application No. PCT/GB2014/053057, PCT International Search Report dated Jan. 21, 2015.
WIPO Application No. PCT/GB2014/053057, PCT Written Opinion of the International Searching Authority dated Jan. 21, 2015.
Nonaka et al., "Diagnostic Utility of Thymic Epithelial Markers CD205 (DEC205) and Foxn1 in Thymic Epithelial Neoplasms," Am J Surg Pathol, 31:1038-1044, (2007).
Tungekar et al., "Bladder carcinomas and normal urothelium universally express gp200-MR6, a molecule functionally associated with the interleukin 4 receptor (CD 124)," British Journal of Cancer, 73:429-432, (1996).
U.S. Appl. No. 14/950,087, Requirement for Restriction/Election dated Nov. 8, 2016.

* cited by examiner

SEQ ID No: 11    EVQLVESGGGLVKPGGSLRLSCAASGFTFSNAWMSWVRQAPGKGLEWVGRIKSKTDGGTT
SEQ ID No: 1     EVQLVESGGGLVKPGGSLRLSCAASGFTYSNAWMSWVRQAPGKGLEWVGRIKSKTDGGTT
SEQ ID No: 12    ------------------------------------------------------------
                 ***************************:****************************

SEQ ID No: 11    DYAAPVKGRFTISRDDSKNTLYLQMNSLKTEDTAVYYCTTTTVT----------------
SEQ ID No: 1     DYAAPVQGRFTISRDDSKNTLYLQMNSLKTEDTAVYYCTIFGVVSFDYWGQGTLVTVSS
SEQ ID No: 12    -------------------------------------YFDYWGQGTLVTVSS
                 ****:****************************         ***********

FIGURE 1

SEQ ID No: 2     DVQMTQSPSSLSASVGDRVTITCRASQSISDYLSWYQQRPGKAPNLLIYAASNLKTGVPS
SEQ ID No: 13    DIQMTQSPSSLSASVGDRVTITCRASQSISSYLNWYQQKPGKAPKLLIYAASSLQSGVPS
SEQ ID No: 14    ------------------------------------------------------------
                 *:*******************************   **:*:***** *: ****

SEQ ID No: 2     RFSGSGSGTDFTLTISTLQPEDFATYYCQQSYRSPWTFGQGTKVEIKR
SEQ ID No: 13    RFSGSGSGTDFTLTISSLQPEDFATYYCQQSYS---------------
SEQ ID No: 14    --------------------------------WTFGQGTKVEIKR
                 **************:*******************    ***********

```
sp|O60449|LY75_HUMAN    MRTGWATPRRPAGLLMLLFWFFDLAEPSGRAANDPFTIVHGNTGKCIKPVYGWIVADDCD 60
MS-Peptides_Elute1a     ---------------------------------------------CIKPVYGWIVADDCD
MS-Peptides_Elute1b     ---------------------------------------------CIKPVYGWIVADDCD
MS-Peptides_Elute2a     ------------------------------------------------------------
MS-Peptides_Elute2b     ------------------------------------------------------------
LC-Peptides             ------------------------------------------------------------ sp|O60449|LY75_HUMAN    ETEDKLWKWVSQHRLFHLHSQKCLGLDITKSVNELRMFSCDSSAMLWWKCEHHSLYGAAR 120
MS-Peptides_Elute1a     ETEDKLWK-------------------------------------CEHHSLYGAAR
MS-Peptides_Elute1b     ETEDKLWK-------------------------------------------------
MS-Peptides_Elute2a     ---------------------------------------------------------
MS-Peptides_Elute2b     ---------------------------------------------------------
LC-Peptides             --------------------------------------------------------- sp|O60449|LY75_HUMAN    YRLALKDGHGTAISNASDVWKKGGSEESLCDQPYHEIYTRDGNSYGRPCEFPFLIDGTWH 180
MS-Peptides_Elute1a     ------DGHGTAISNASDVWKKGGSEESLCDQPYHEIYTR--------------------
MS-Peptides_Elute1b     ----------------------KGGSEESLCDQPYHEIYTR--------------------
MS-Peptides_Elute2a     -----------------------GGSEESLCDQPYHEIYTR--------------------
MS-Peptides_Elute2b     -----------------------GGSEESLCDQPYHEIYTR--------------------
LC-Peptides             ------DGHGTAISNASDVWK--------------------------------------- sp|O60449|LY75_HUMAN    HDCILDEDHSGPWCATTLNYEYDRKWGICLKPENGCEDNWEKNEQFGSCYQFNTQTALSW 240
MS-Peptides_Elute1a     ------------------------------------------------------------
MS-Peptides_Elute1b     ------------------------WGICLKPENGCEDNWEK-------------------
MS-Peptides_Elute2a     ------------------------------------------------------------
MS-Peptides_Elute2b     ------------------------------------------------------------
LC-Peptides             ------------------------------------------------------------ sp|O60449|LY75_HUMAN    KEAYVSCQNQGADLLSINSAAELTYLKEKEGIAKIFWIGLNQLYSARGWEWSDHKPLNFL 300
MS-Peptides_Elute1a     -------------------------------IFWIGLNQLYSAR---------------
MS-Peptides_Elute1b     ------------------------------------------------------------
MS-Peptides_Elute2a     -------------------------------IFWIGLNQLYSAR---------------
MS-Peptides_Elute2b     ------------------------------------------------------------
LC-Peptides             ------------------------------------------------------------ sp|O60449|LY75_HUMAN    NWDPDRPSAPTIGGSSCARMDAESGLWQSFSCEAQLPYVCRKPLNNTVELTDVWTYSDTR 360
MS-Peptides_Elute1a     ------------------------------------------------------------
MS-Peptides_Elute1b     ------------------------------------------------------------
MS-Peptides_Elute2a     ------------------------------------------------------------
MS-Peptides_Elute2b     ------------------------------------------------------------
LC-Peptides             ------------------------------------------------------------ sp|O60449|LY75_HUMAN    CDAGWLPNNGFCYLLVNESNSWDKAHAKCKAFSSDLISIHSLADVEVVVTKLHNEDIKEE 420
MS-Peptides_Elute1a     ---------------------------------------------------LHNEDIKEE
MS-Peptides_Elute1b     ---------------------------------------------------LHNEDIKEE
MS-Peptides_Elute2a     ------------------------------------------------------------
MS-Peptides_Elute2b     ------------------------------------------------------------
LC-Peptides             ------------------------------------------------------------ sp|O60449|LY75_HUMAN    VWIGLKNINIPTLFQWSDGTEVTLTYWDENEPNVPYNKTPNCVSYLGELGQWKVQSCEEK 480
MS-Peptides_Elute1a     VWIGLK-------------------------TPNCVSYLGELGQWK-------
MS-Peptides_Elute1b     VWIGLK-------------------------TPNCVSYLGELGQWK-------
MS-Peptides_Elute2a     ------------------------------------------------------------
MS-Peptides_Elute2b     ------------------------------------------------------------
LC-Peptides             ------------------------------------------------------------
```

Figure 7B

```
sp|O60449|LY75_HUMAN    LKYVCKRKGEKLNDASSDKMCPPDEGWKRHGETCYKIYEDEVPFGTNCNLTITSRFEQEY 540
MS-Peptides_Elute1a     ------------------------------------------------------------
MS-Peptides_Elute1b     ------------------------------------------------------------
MS-Peptides_Elute2a     ------------------------------------------------------------
MS-Peptides_Elute2b     ------------------------------------------------------------
LC-Peptides             ------------------------------------------------------------ sp|O60449|LY75_HUMAN    LNDLMKKYDKSLRKYFWTGLRDVDSCGEYNWATVGGRRRAVTFSNWNFLEPASPGGCVAM 600
MS-Peptides_Elute1a     ---------------YFWTGLRDVDSCGEYNWATVGGR----------------------
MS-Peptides_Elute1b     ---------------YFWTGLRDVDSCGEYNWATVGGR----------------------
MS-Peptides_Elute2a     ---------------YFWTGLRDVDSCGEYNWATVGGR----------------------
MS-Peptides_Elute2b     ---------------YFWTGLRDVDSCGEYNWATVGGR----------------------
LC-Peptides             ------------------------------------------------------------ sp|O60449|LY75_HUMAN    STGKSVGKWEVKDCRSFKALSICKKMSGPLGPEEASPKPDDPCPEGWQSFPASLSCYKVF 660
MS-Peptides_Elute1a     ----SVGKWEVKDCR---ALSICKK-----------------------------------
MS-Peptides_Elute1b     ------------------------------------------------------------
MS-Peptides_Elute2a     ------------------------------------------------------------
MS-Peptides_Elute2b     ------------------------------------------------------------
LC-Peptides             --------WEVKDCRSFK-----------------------------PASLSCYKVF sp|O60449|LY75_HUMAN    HAERIVRKRNWEEAERFCQALGAHLSSFSHVDEIKEFLHFLTDQFSGQHWLWIGLNKRSP 720
MS-Peptides_Elute1a     ---------RNWEEAER----------------------------------------RSP
MS-Peptides_Elute1b     ---------RNWEEAER----------------------------------------RSP
MS-Peptides_Elute2a     ------------------------------------------------------------
MS-Peptides_Elute2b     ------------------------------------------------------------
LC-Peptides             HA---------------------------------------------------------- sp|O60449|LY75_HUMAN    DLQGSWQWSDRTPVSTIIMPNEFQQDYDIRDCAAVKVFHRPWRRGWHFYDDREFIYLRPF 780
MS-Peptides_Elute1a     -----------TPVSTIIMPNEFQQDYDIR------------------------------
MS-Peptides_Elute1b     DLQGSWQWSDRTPVSTIIMPNEFQQDYDIR------------------------------
MS-Peptides_Elute2a     ------------------------------------------GWHFYDDR----------
MS-Peptides_Elute2b     ------------------------------------------------------------
LC-Peptides             --------------------------------------PWRRGWHFYDDREFIYLRPF sp|O60449|LY75_HUMAN    ACDTKLEWVCQIPKGRTPKTPDWYNPDRAGIHGPPLIIEGSEYWFVADLHLNYEEAVLYC 840
MS-Peptides_Elute1a     ------------------------------------------------------------
MS-Peptides_Elute1b     ------------------------------------------------------------
MS-Peptides_Elute2a     ------------------------------------------------------------
MS-Peptides_Elute2b     ------------------------------------------------------------
LC-Peptides             ------------------------------------------------------------ sp|O60449|LY75_HUMAN    ASNHSFLATITSFVGLKAIKNKIANISGDGQKWWIRISEWPIDDHFTYSRYPWHRFPVTF 900
MS-Peptides_Elute1a     -------------------------------------ISEWPIDDHFTYSR----FPVTF
MS-Peptides_Elute1b     -------------------------------------ISEWPIDDHFTYSR---------
MS-Peptides_Elute2a     ------------------------------------------------------------
MS-Peptides_Elute2b     ------------------------------------------------------------
LC-Peptides             -------------------------------------------DDHFTYSRYPWHRFPVTF
                                                                    ******** sp|O60449|LY75_HUMAN    GEECLYMSAKTWLIDLGKPTDCSTKLPFICEKYNVSSLEKYSPDSAAKVQCSEQWIPFQN 960
MS-Peptides_Elute1a     GEECLYMSAKTWLIDLGKPTDCSTK-------YNVSSLEK--------VQCSEQWIPFQN
MS-Peptides_Elute1b     ----------TWLIDLGKPTDCSTK-------YNVSSLEK--------VQCSEQWIPFQN
MS-Peptides_Elute2a     ----------TWLIDLGKPTDCSTK-----------------------------------
MS-Peptides_Elute2b     ----------TWLIDLGKPTDCSTK-----------------------------------
LC-Peptides             G-----------------------------------------------------------
```

Figure 7C

```
sp|O60449|LY75_HUMAN  KCFLKIKPVSLTFSQASDTCHSYGGTLPSVLSQIEQDFITSLLPDMEATLWIGLRWTAYE 1020
MS-Peptides_Elute1a   ------------------------------------------------------------
MS-Peptides_Elute1b   ------------------------------------------------------------
MS-Peptides_Elute2a   ------------------------------------------------------------
MS-Peptides_Elute2b   ------------------------------------------------------------
LC-Peptides           ------------------------------------------------------------ sp|O60449|LY75_HUMAN  KINKWTDNRELTYSNFHPLLVSGRLRIPENFFEEESRYHCALILNLQKSPFTGTWNFTSC 1080
MS-Peptides_Elute1a   K--------ELTYSNFHPLLVSGRLRIPENFFEEESRYHCALILNLQK------------
MS-Peptides_Elute1b   K-----------------------------------YHCALILNLQK------------
MS-Peptides_Elute2a   ------------------------------------------------------------
MS-Peptides_Elute2b   ------------------------------------------------------------
LC-Peptides           --------RELTYSNFHPLL--------------------------------FTSC sp|O60449|LY75_HUMAN  SERHFVSLCQKYSEVKSRQTLQNASETVKYLNNLYKIIPKTLTWHSAKRECLKSNMQLVS 1140
MS-Peptides_Elute1a   ---HFVSLCQK-------QTLQNASETVK-----------TLTWHSAK------------
MS-Peptides_Elute1b   ---HFVSLCQK-------QTLQNASETVK-----------TLTWHSAK------------
MS-Peptides_Elute2a   ------------------------------------------------------------
MS-Peptides_Elute2b   ------------------------------------------------------------
LC-Peptides           SERHFVSLCQKYS-----------TVKYLNNLYKII------------------------
                         ******           * sp|O60449|LY75_HUMAN  ITDPYQQAFLSVQALLHNSSLWIGLFSQDDELNFGWSDGKRLHFSRWAETNGQLEDCVVL 1200
MS-Peptides_Elute1a   ------------------------------------------------------------
MS-Peptides_Elute1b   ------------------------------------------------------------
MS-Peptides_Elute2a   ------------------------------------------------------------
MS-Peptides_Elute2b   ------------------------------------------------------------
LC-Peptides           ------------------------------------------------------------ sp|O60449|LY75_HUMAN  DTDGFWKTVDCNDNQPGAICYYSGNETEKEVKPVDSVKCPSPVLNTPWIPFQNCCYNFII 1260
MS-Peptides_Elute1a   ------------------------------------------------------------
MS-Peptides_Elute1b   ------------------------------------------------------------
MS-Peptides_Elute2a   ------------------------------------------------------------
MS-Peptides_Elute2b   ------------------------------------------------------------
LC-Peptides           ------------------------------------------------------------ sp|O60449|LY75_HUMAN  TKNRHMATTQDEVHTKCQKLNPKSHILSIRDEKENNFVLEQLLYFNYMASWVMLGITYRN 1320
MS-Peptides_Elute1a   ------------------------------SHILSIR-----------------------
MS-Peptides_Elute1b   --NRHMATTQDEVHTK-------SHILSIR------------------------------
MS-Peptides_Elute2a   ------------------------------------------------------------
MS-Peptides_Elute2b   ------------------------------------------------------------
LC-Peptides           ------------------------------------------------------------ sp|O60449|LY75_HUMAN  KSLMWFDKTPLSYTHWRAGRPTIKNEKFLAGLSTDGFWDIQTFKVIEEAVYFHQHSILAC 1380
MS-Peptides_Elute1a   -SLMWFDKTPLSYTHWR-------------------------------------------
MS-Peptides_Elute1b   -SLMWFDK----------------------------------------------------
MS-Peptides_Elute2a   -SLMWFDK----------------------------------------------------
MS-Peptides_Elute2b   ------------------------------------------------------------
LC-Peptides           ---------------------------------------EAVYFHQHSIL-- sp|O60449|LY75_HUMAN  KIEMVDYKEEYNTTLPQFMPYEDGIYSVIQKKVTWYEALNMCSQSGGHLASVHNQNGQLF 1440
MS-Peptides_Elute1a   ------------------------------------------------------------
MS-Peptides_Elute1b   ------------------------------------------------------------
MS-Peptides_Elute2a   ------------------------------------------------------------
MS-Peptides_Elute2b   ------------------------------------------------------------
LC-Peptides           ------------------------------------------------------------
```

Figure 7D

```
sp|O60449|LY75_HUMAN    LEDIVKRDGFPLWVGLSSHDGSESSFEWSDGSTFDYIPWKGQTSPGNCVLLDPKGTWKHE 1500
MS-Peptides_Elute1a     ------------------------------------------------------------
MS-Peptides_Elute1b     ------------------------------------------------------------
MS-Peptides_Elute2a     ------------------------------------------------------------
MS-Peptides_Elute2b     ------------------------------------------------------------
LC-Peptides             ------------------------------------------------------------ sp|O60449|LY75_HUMAN    KCNSVKDGAICYKPTKSKKLSRLTYSSRCPAAKENGSRWIQYKGHCYKSDQALHSFSEAK 1560
MS-Peptides_Elute1a     ------------------------------------------------------------
MS-Peptides_Elute1b     ------------------------------------------------------------
MS-Peptides_Elute2a     ------------------------------------------------------------
MS-Peptides_Elute2b     ------------------------------------------------------------
LC-Peptides             ------------------KKLSRLTYSS-C-----NGSRWIQYKGHCYKSDQALH------ sp|O60449|LY75_HUMAN    KLCSKHDHSATIVSIKDEDENKFVSRLMRENNNITMRVWLGLSQHSVDQSWSWLDGSEVT 1620
MS-Peptides_Elute1a     -----HDHSATIVSIKDEDENKFVSR----------------------------------
MS-Peptides_Elute1b     -----HDHSATIVSIKDEDENKFVSR----------------------------------
MS-Peptides_Elute2a     -----HDHSATIVSIKDEDENKFVSR----------------------------------
MS-Peptides_Elute2b     ------------------------------------------------------------
LC-Peptides             ------------------------------------------------------------ sp|O60449|LY75_HUMAN    FVKWENKSKSGVGRCSMLIASNETWKKVECEHGFGRVVCKVPLGPDYTAIAIIVATLSIL 1680
MS-Peptides_Elute1a     ---------------------------VECEHGFGR------------------------
MS-Peptides_Elute1b     ---------------------------VECEHGFGR------------------------
MS-Peptides_Elute2a     ------------------------------------------------------------
MS-Peptides_Elute2b     ------------------------------------------------------------
LC-Peptides             ------------------------------------------------------------ sp|O60449|LY75_HUMAN    VLMGGLIWFLFQRHRLHLAGFSSVRYAQGVNEDEIMLPSFHD 1722
MS-Peptides_Elute1a     ------------------------------------------
MS-Peptides_Elute1b     ------------------------------------------
MS-Peptides_Elute2a     ------------------------------------------
MS-Peptides_Elute2b     ------------------------------------------
LC-Peptides             ------------------------------------------
```

CONJUGATED ANTIBODIES AGAINST LY75 FOR THE TREATMENT OF CANCER

CROSS-REFERENCE TO RELATED APPLICATION

The present application is a US National Stage entry of PCT/GB2014/053057 filed Oct. 10, 2014, which claims the benefit under 35 USC 119(e) of U.S. Provisional Application No. 61/890,098 filed Oct. 11, 2013 and U.S. Provisional Application No. 61/890,104 filed Oct. 11, 2013, all of which are incorporated by reference it its entirety for all purposes.

INTRODUCTION

The present disclosure relates generally to the fields of immunology and molecular biology. More specifically, provided herein are antibodies and other therapeutic proteins directed against LY75, nucleic acids encoding such antibodies and therapeutic proteins, methods for preparing monoclonal antibodies and other therapeutic proteins, and methods for the treatment of diseases, such as cancers mediated by LY75 expression/activity and/or associated with abnormal expression/activity of ligands therefore.

BACKGROUND

Lymphocyte antigen 75 acts as an endocytic receptor to direct captured antigens from the extracellular space to a specialized antigen-processing compartment and is thought to cause a reduction in proliferation of B-lymphocytes. Expression of Lymphocyte antigen 75 has been observed in pancreatic, ovarian, breast, colorectal, esophageal, skin, thyroid and lung (non-small-cell) cancers as well as Multiple Myeloma and many different subtypes of lymphomas and leukaemias.

WO2009/061996 discloses isolated monoclonal antibodies which bind to human DEC-205 (LY75) and related antibody based compositions and molecules. Also disclosed are pharmaceutical compositions comprising the antibodies, as well as therapeutic and diagnostic methods for using the antibodies.

WO2008/104806 discloses affinity reagents capable of binding to LY75 for use in the treatment or prophylaxis of cancer.

BRIEF SUMMARY OF THE INVENTION

The present invention provides antibodies directed against LY75, nucleic acids encoding such antibodies, host cells comprising such nucleic acids encoding the antibodies of the invention, methods for preparing anti-LY75, and methods for the treatment of diseases, such as the LY75 mediated disorders, e.g. human cancers, including pancreatic cancer, ovarian cancer, breast cancer, colorectal cancer, esophageal cancer, skin cancer, thyroid cancer, lung cancer, head and neck cancer, bladder cancer, gastric cancer, leukaemia, multiple myeloma and lymphoma.

In one aspect, the invention provides an antibody, or an antigen-binding portion thereof, which: (a) binds an epitope on LY75 which is recognized by an antibody comprising a heavy chain variable region comprising the amino acid sequence set forth in SEQ ID NO: 1 and a light chain variable region comprising the amino acid sequence set forth in SEQ ID NO: 2, or (b) competes for binding to LY75 with an antibody comprising a heavy chain variable region comprising the amino acid sequence set forth in SEQ ID NO: 1, and a light chain variable region comprising the amino acid sequence set forth in SEQ ID NO: 2.

In one embodiment, the antibody or antigen-binding portion thereof binds to human LY75 and comprises a heavy chain variable region comprising 1, 2 or 3 CDRs selected from the group consisting of CDRs comprising SEQ ID NOs: 5, 6, and 7, and/or a light chain variable region comprising 1, 2 or 3 CDRs selected from the group consisting of CDRs comprising SEQ ID NOs: 8, 9 and 10.

In preferred embodiments said antibodies are isolated antibodies.

In some embodiments, the antibodies of the invention bind to LY75 (SEQ ID No: 15) and are internalized by a cell expressing LY75, elicit an antibody dependent cellular cytotoxicity (ADCC) response in the presence of effector cells or elicit a cytotoxic T-Cell response in the presence of effector cells.

In another embodiment, the antibody comprises the heavy and/or light chain complementarity determining regions (CDRs) or variable regions (VRs) of the particular antibody described herein (e.g., referred to herein as "LY75_A1"). Accordingly, in one embodiment, the antibody comprises the CDR1, CDR2, and CDR3 domains of the heavy chain variable (VH) region of antibody LY75_A1 having the sequence shown in SEQ ID NO:1, and/or the CDR1, CDR2 and CDR3 domains of the light chain variable (VL) region of LY75_A1 having the sequence shown in SEQ ID NO:2. In another embodiment, the antibody comprises a heavy chain variable region comprising a first vhCDR comprising SEQ ID NO:5; a second vhCDR comprising SEQ ID NO:6; and a third vhCDR comprising SEQ ID NO:7; and/or a light chain variable region comprising a first vlCDR comprising SEQ ID NO:8; a second vlCDR comprising SEQ ID NO:9; and a third vlCDR comprising SEQ ID NO:10, optionally wherein any one or more of the CDRs independently comprise one, two, three, four or five amino acid substitutions, additions or deletions.

In another embodiment, the antibodies of the invention bind to human LY75 and include a heavy chain variable region comprising SEQ ID NO:1, and/or conservative sequence modifications thereof. The antibody may further include a light chain variable region comprising SEQ ID NO:2, and/or conservative sequence modifications thereof.

In a further embodiment, the antibodies of the invention bind to human LY75 and include a heavy chain variable region and a light chain variable region including the amino acid sequences set forth in SEQ ID NOs:1 and/or 2, respectively, and conservative sequence modifications thereof.

Isolated antibodies which include heavy and light chain variable regions having at least 80%, or at least 85%, or at least 90%, or at least 91%, or at least 92%, or at least 93%, or at least 94%, or at least 95%, or at least 96%, or at least 97%, or at least 98%, or at least 99%, or more sequence identity to any of the above sequences are also included in the present invention. Ranges intermediate to the above-recited values, e.g., heavy and light chain variable regions having at least 80-85%, 85-90%, 90-95% or 95-100% sequence identity to any of the above sequences are also intended to be encompassed by the present invention. In one embodiment, the antibody comprises a heavy chain variable region comprising SEQ ID NO:1 or a sequence that is at least 80%, at least 85%, at least 90%, at least 91%, at least 92%, at least 93%, at least 94%, at least 95%, at least 96%, at least 97%, at least 98%, at least 99% identical to SEQ ID NO: 1. In another embodiment, the antibody comprises a light chain variable region comprising SEQ ID NO:2 or a sequence that is at least 80%, at least 85%, at least 90%, at least 91%, at least 92%, at least 93%, at least 94%, at least 95%, at least 96%, at least 97%, at least 98%, at least 99% identical to SEQ ID NO: 2. In another embodiment, the antibody comprises a heavy chain framework region comprising an amino acid sequence that is at least 80%, at least 85%, at least 90%, at least 91%, at least 92%, at least 93%, at least 94%, at least 95%, at least 96%, at least 97%, at least 98%, at least 99% identical to the framework of the heavy chain variable region of SEQ ID NO: 1 as shown in SEQ ID NOS: 16, 17, 18 and 19. In another embodiment, the antibody comprises a light chain framework region comprising an amino acid sequence that is at least 80%, at least 85%, at least 90%, at least 91%, at least 92%, at least 93%, at least 94%, at least 95%, at least 96%, at least 97%, at least 98%, at least 99% identical to the framework of the light chain variable region of SEQ ID NO:2 as shown in SEQ ID NOS: 20, 21, 22 and 23.

Also encompassed by the present invention are antibodies which compete for binding to LY75 with the antibodies of the invention. In a particular embodiment, the antibody competes for binding to LY75 with an antibody comprising heavy and/or light chain variable regions comprising the amino acid sequences set forth in SEQ ID NOs:1 and 2, respectively, or amino acid sequences at least 80%, at least 85%, at least 90%, at least 91%, at least 92%, at least 93%, at least 94%, at least 95%, at least 96%, at least 97%, at least 98%, at least 99% identical thereto. In another embodiment, the antibody competes for binding to LY75 with an antibody comprising heavy and/or light chain variable regions comprising the amino acid sequences set forth in SEQ ID NOs:1 and 2 (LY75_A1).

Other antibodies of the invention bind to the same epitope or an epitope on LY75 recognized by the antibodies described herein. In another particular embodiment, the antibody binds to an epitope on LY75 recognized by an antibody comprising heavy and/or light chain variable regions comprising the amino acid sequences set forth in SEQ ID NOs:1 and 2, respectively, or amino acid sequences at least 80% identical thereto. In another embodiment, the antibody binds to an epitope on LY75 recognized by an antibody comprising heavy and/or light chain variable regions comprising the amino acid sequences set forth in SEQ ID NOs:1 and 2 (LY75_A1).

In a further embodiment, the antibodies of the invention bind specifically to one or more, for example, 2, 3, 4, 5, 6, 7, 8, 9 or 10, peptide(s) selected from the group comprising SEQ ID NOs: 24, 25, 26, 27, 28, 29, 30, 31, 32, 33, 34, 35, 36 or 37 or fragments thereof, wherein said fragments comprises at least 2, at least 3, at least 4, at least 5, at least 6, at least 7, at least 8, at least 9 or at least 10 contiguous amino acids. In a further embodiment, the epitope recognized by the antibodies of the present invention comprises one or more peptides, two or more or three or more peptides selected from the group consisting of SEQ ID NOs: 27, 29, 30, 34, 35, 36 or 37 or fragments thereof wherein said fragments comprises at least 2, at least 3, at least 4, at least 5, at least 6, at least 7, at least 8, at least 9 or at least 10 contiguous amino acids. In a further embodiment, the epitope recognized by the antibodies of the present invention comprises one or more peptides, for example, two or three peptides selected from the group consisting of SEQ ID NOs: 30, 36 and 37 or fragments thereof wherein said fragments comprises at least 2, at least 3, at least 4, at least 5, at least 6, at least 7, at least 8, at least 9 or at least 10 contiguous amino acids.

In a further embodiment, the antibodies of the invention comprise variable CDRs as compared to the parent antibodies described herein. Thus, the invention provides variant antibodies comprising variant variable regions of a parent antibody, wherein the parent antibody comprises a first vhCDR comprising SEQ ID NO:5, a second vhCDR comprising SEQ ID NO: 6, a third vhCDR comprising SEQ ID NO:7, a first vlCDR comprising SEQ ID NO:8, a second vlCDR comprising SEQ ID NO:9 and a third vlCDR comprising a SEQ ID NO:10, and wherein the variant antibody has 1, 2, 3, 4, 5 or 6 amino acid substitutions collectively in the set of the first vhCDR, the second vhCDR, the third vhCDR, the first vlCDR, the second vlCDR and the third vlCDR, with from 1 to 4, 1 to 3 or 1 to 2 substitutions of particular use, and wherein the antibody retains specific binding to LY75.

The antibodies of the invention can either be full-length, for example, any of the following isotypes: IgG1, IgG2, IgG3, IgG4, IgM, IgA1, IgA2, IgAsec, IgD, and IgE. Alternatively, the antibodies can be fragments such as an antigen-binding portion or a single chain antibody (e.g., a Fab, F(ab')$_2$, Fv, a single chain Fv fragment, an isolated complementarity determining region (CDR) or a combination of two or more isolated CDRs). The antibodies can be any kind of antibody, including, but not limited to, human, humanized, and chimeric antibodies.

In other embodiments, the antibodies of the invention are in the form of an immunoconjugate (i.e., further include a covalently attached moiety). In a particular embodiment, the moiety is a drug, such as a maytansinoid, a dolastatin, an auristatin, a trichothecene, a calicheamicin, CC1065 or derivatives thereof. In a preferred embodiment, the drug moiety is DM1 or DM4

In other embodiments, the antibodies of the invention further encompass a bispecific molecule and as such can elicit an antibody dependent cellular cytotoxicity (ADCC) response in the presence of effector cells, thus killing LY75-expressing cells.

In other embodiments, the antibodies of the invention further encompass a bispecific molecule and as such can elicit a cytotoxic T-cell response in the presence of effector cells, thus killing LY75-expressing cells.

In another aspect, the invention provides, nucleic acids encoding the heavy and/or light chain variable regions of the antibodies of the invention. In one embodiment, there is provided a nucleic acid comprising a sequence encoding the heavy chain of the antibody of the invention or the antigen-binding portion thereof. In another embodiment there is provided a nucleic acid comprising a sequence encoding the light chain of the antibody of the invention or the antigen-binding portion thereof. In a further embodiment there is provided a nucleic acid comprising a sequence encoding the heavy and light chain variable regions of the antibodies of the invention.

In one embodiment, the invention provides an isolated monoclonal antibody that binds human LY75, wherein the antibody comprises a heavy chain variable region and a light chain variable region encoded by nucleic acid sequences comprising SEQ ID NOs:3 and 4, respectively, or nucleic acid sequences having at least 85%, 86%, 87%, 88%, 89%, 90%, 91%, 92%, 93%, 94%, 95%, 96%, 97%, 98% or 99% identity to the aforementioned nucleic acid sequences or sequences which differ from SEQ ID NOs: 3 and 4 due to degeneracy of the genetic code.

In another aspect of the present invention there are provided expression vectors comprising nucleic acids encoding heavy and/or light chain variable regions of the antibodies of the invention operably linked to one or more regulatory elements.

In another aspect, the invention provides host cells containing nucleic acids encoding heavy and/or light chain variable regions or the antigen binding portions thereof of the foregoing antibodies. Preferably, wherein the host cell expresses said heavy and/or light chain variable regions or the antigen binding portions thereof when the host cell is grown under conditions wherein the nucleic acid(s) is expressed.

In a preferred embodiment the host cell comprises: (i) an expression vector according to the present invention; or (ii) a first expression vector comprising the nucleic acid sequence encoding the heavy chain of the antibody of the invention or the antigen-binding portion thereof and a second expression vector comprising the nucleic acid sequence encoding the light chain of the antibody of the invention or the antigen-binding portion thereof.

In a further aspect of the present invention there is provided of making an antibody or an antigen-binding portion thereof, comprising culturing a host cell according to the present invention under conditions where the antibody or an antigen-binding portion thereof is expressed and optionally isolating the antibody or an antigen-binding portion thereof.

In a further aspect there is provided a method of treating cancer comprising administering to a patient in need thereof an antibody or an antigen-binding portion thereof of according to the present invention wherein the antibody or antigen-binding portion thereof is internalized by a cell expressing LY75, said antibody or antigen-binding portion comprising a covalently attached drug conjugate. It will be understood that the antibody or an antigen-binding portion thereof of the invention is one which binds to LY75 (SEQ ID No: 15). In one embodiment, the antibody comprises a heavy chain variable region comprising a first vhCDR comprising SEQ ID NO:5; a second vhCDR comprising SEQ ID NO:6; and a third vhCDR comprising SEQ ID NO:7; and a light chain variable region comprising a first vlCDR comprising SEQ ID NO:8; a second vlCDR comprising SEQ ID NO: 9; and a third vlCDR comprising SEQ ID NO:10 and a covalently attached drug conjugate.

In a further aspect, there is provided a method of treating cancer, wherein a patient in need thereof is administered an antibody or antibodies or an antigen-binding portion thereof of the invention and wherein such antibody or antibodies or an antigen-binding portion thereof of the invention elicit an ADCC response in the presence of effector cells. Preferably, the antibody or an antigen-binding portion thereof comprises a heavy chain variable region comprising a first vhCDR comprising SEQ ID NO: 5; a second vhCDR comprising SEQ ID NO: 6; and a third vhCDR comprising SEQ ID NO: 7; and a light chain variable region comprising a first vlCDR comprising SEQ ID NO: 8; a second vlCDR comprising SEQ ID NO: 9; and a third vlCDR comprising SEQ ID NO: 10.

In a further aspect there is provided a method of treating cancer, wherein a patient in need thereof is administered an antibody or antibodies or an antigen-binding portion thereof of the invention and wherein such antibody or antibodies or an antigen-binding portion thereof of the invention elicit a cytotoxic T-cell response in the presence of effector cells. Preferably, the antibody comprises a heavy chain variable region comprising a first vhCDR comprising SEQ ID NO: 5; a second vhCDR comprising SEQ ID NO: 6; and a third vhCDR comprising SEQ ID NO: 7; and a light chain variable region comprising a first vlCDR comprising SEQ ID NO: 8; a second vlCDR comprising SEQ ID NO: 9; and a third vlCDR comprising SEQ ID NO: 10.

In a further aspect of the present invention there is provided one or more antibodies of the invention for use in the treatment of cancer.

Also provided is the use of one or more antibodies of the invention in the manufacture of a medicament for the treatment of cancer.

In some embodiments, the cancer is selected from the group consisting of pancreatic cancer, kidney cancer, liver cancer, ovarian cancer, breast cancer, colorectal cancer, esophageal cancer, head and neck cancer, skin cancer, thyroid cancer, bladder cancer, gastric cancer, lung cancer, leukaemia, myeloma, preferably multiple myeloma, and lymphoma. Particularly preferred cancers include non-Hodgkin's lymphoma, diffuse large B-cell lymphoma (DLBCL), B-Cell Lymphoma, Follicular Lymphoma, Mantle Cell Lymphoma, Lymphoma of Mucosa-Associated Lymphoid Tissue (MALT), T-Cell/Histiocyte-Rich B-Cell Lymphoma, Burkitt's Lymphoma, Lymphoplasmacytic Lymphoma, Small Lymphocytic Lymphoma, Marginal Zone Lymphoma, T Cell Lymphoma, Peripheral T-Cell Lymphoma, Anaplastic Large Cell Lymphoma and AngioImmunoblastic T-Cell Lymphoma, acute myeloid leukaemia, chronic lymphocytic leukaemia, bladder cancer, pancreatic cancer and triple-negative breast cancer.

According to a still further aspect of the invention there is provided method of detecting, diagnosing and/or screening for or monitoring the progression of a cancer wherein LY75 is expressed in said cancer, or of monitoring the effect of a cancer drug or therapy directed to said cancer, in a subject which comprises detecting the presence or level of antibodies capable of immunospecific binding to LY75, or one or more fragments thereof.

Preferably, the cancer is selected from the group consisting of pancreatic cancer, kidney cancer, liver cancer, ovarian cancer, breast cancer, colorectal cancer, esophageal cancer, head and neck cancer, skin cancer, thyroid cancer, bladder cancer, gastric cancer, lung cancer, leukaemia, myeloma, preferably multiple myeloma, and lymphoma. Particularly preferred cancers include non-Hodgkin's lymphoma, diffuse large B-cell lymphoma (DLBCL), B-Cell Lymphoma, Follicular Lymphoma, Mantle Cell Lymphoma, Lymphoma of Mucosa-Associated Lymphoid Tissue (MALT), T-Cell/Histiocyte-Rich B-Cell Lymphoma, Burkitt's Lymphoma, Lymphoplasmacytic Lymphoma, Small Lymphocytic Lymphoma, Marginal Zone Lymphoma, T Cell Lymphoma, Peripheral T-Cell Lymphoma, Anaplastic Large Cell Lymphoma and AngioImmunoblastic T-Cell Lymphoma, acute myeloid leukaemia, chronic lymphocytic leukaemia, bladder cancer, pancreatic cancer and triple-negative breast cancer.

Also within the scope of the invention are kits comprising the compositions (e.g., antibodies) of the invention and, optionally, instructions for use. The kit can further contain a least one additional reagent or one or more additional antibodies of the invention.

Other features and advantages of the instant invention will be apparent from the following detailed description and claims.

BRIEF DESCRIPTION OF THE DRAWINGS

FIG. 1 depicts the alignment of LY75_A1 heavy chain (SEQ ID NO:1), the human VH 3-15 Germline (SEQ ID NO:11) and the human JH4 Germline (SEQ ID NO:12). The CDR regions of LY75_A1 heavy chain are underlined.

FIG. 2 depicts the alignment of LY75_A1 light chain (SEQ ID NO:2), the human VK O12 Germline (SEQ ID NO:13) and the human JK4 Germline (SEQ ID NO:14). The CDR regions of LY75_A1 light chain are underlined.

FIGS. 7A, 7B, 7C, & 7D, together, show shows an amino acid alignment of peptides bound by antibody LY75_A1 in both the peptide microarray assay and the peptide pull down assay. Peptides highlighted are those likely to form the epitope recognized by antibody LY75_A1.

DETAILED DESCRIPTION OF THE INVENTION

Figure 3A:
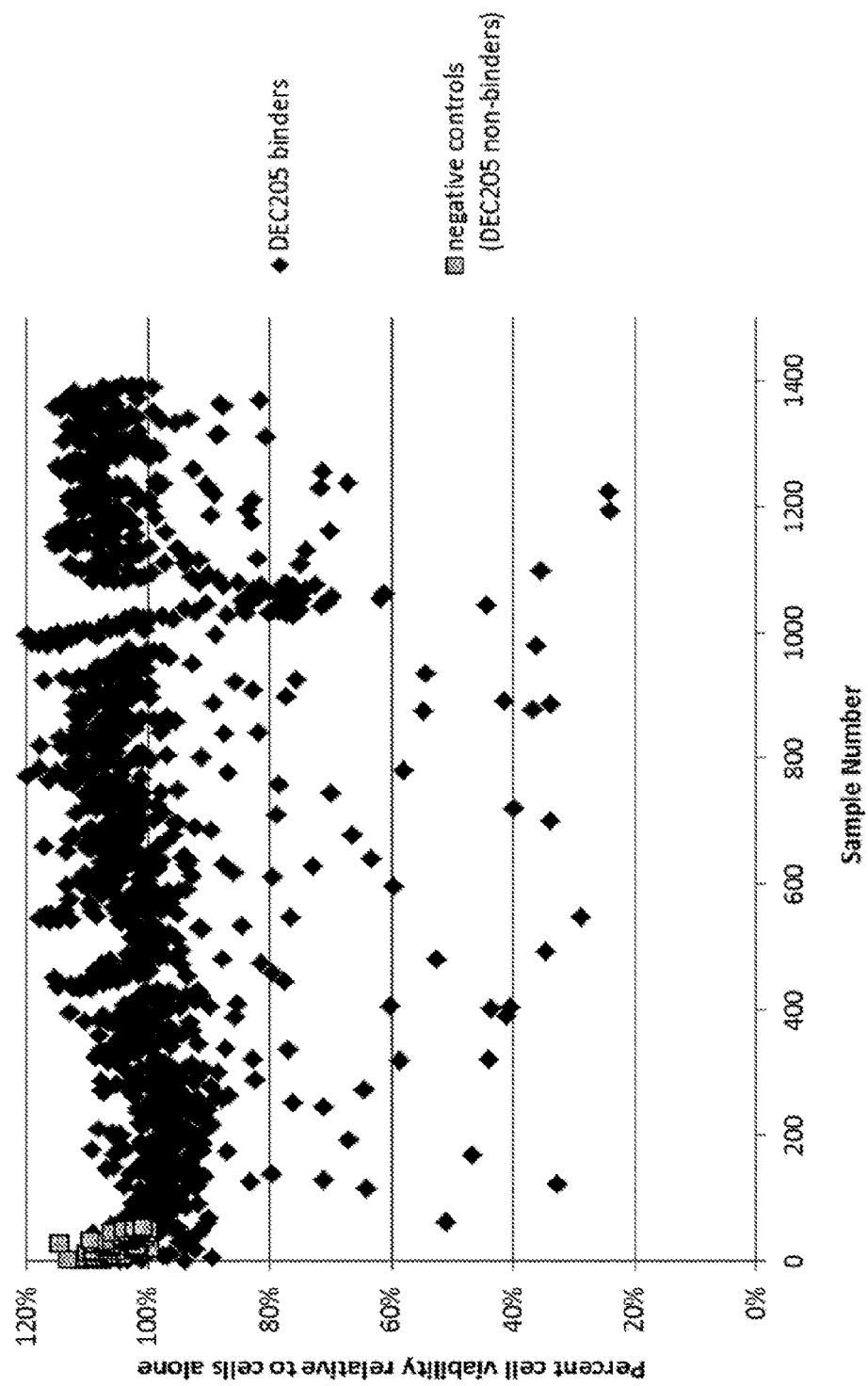
FIG. 3a depicts cytotoxic activity of anti-LY75 monoclonal antibodies conjugated with DM1 in HT-29 and shows while most antibodies bind to LY75 only a few display efficacy.

The present disclosure relates to isolated antibodies which bind to LY75 protein described in SEQ ID No: 15 as outlined herein.

In addition, the LY75 antibodies of the present invention maybe a bispecific molecule and as such can elicit an antibody dependent cellular cytotoxicity (ADCC) response in the presence of effector cells, thus killing LY75-expressing cells.

In addition, the LY75 antibodies of the present invention maybe a bispecific molecule and as such can elicit a cytotoxic T-cell response in the presence of effector cells, thus killing LY75-expressing cells.

In addition, the LY75 antibodies of the present invention maybe internalized when contacted with cells expressing the LY75 receptor. As discussed herein, the LY75 receptor is overexpressed and/or differentially expressed on certain cancer cells, including but not limited to, kidney cancer, liver cancer, esophageal cancer, head and neck cancer, skin cancer, thyroid cancer, gastric cancer, colorectal cancer, pancreatic cancer, prostate cancer, breast cancer, ovarian cancer bladder cancer, leukaemia preferably acute myeloid leukaemia or chronic lymphocytic leukaemia, myeloma, preferably multiple myeloma, lymphoma, preferably DLBCL B-Cell Lymphoma, Follicular Lymphoma, Mantle Cell Lymphoma, Lymphoma of Mucosa-Associated Lymphoid Tissue (MALT), T-Cell/Histiocyte-Rich B-Cell Lymphoma, Burkitt's Lymphoma, Lymphoplasmacytic Lymphoma, Small Lymphocytic Lymphoma, Marginal Zone Lymphoma, T Cell Lymphoma, Peripheral T-Cell Lymphoma, Anaplastic Large Cell Lymphoma and Angiolmmunoblastic T-Cell Lymphoma, and lung cancer.

As such, when the LY75 antibodies of the present invention are conjugated to drugs (sometimes referred to herein as "antibody-drug conjugates" or "ADCs"), the internalization of these ADC molecules into cancer cells results in cell death and thus tumor treatment.

The present invention provides antibodies that possess particular structural features such as CDR regions with particular amino acid sequences. Described herein, are a set of CDRs which can form an affinity reagent, e.g. an antibody, which exhibits binding to LY75.

Thus, the disclosure provides antibodies, preferably isolated antibodies (which, as outlined below, includes a wide variety of well-known antibody structures, derivatives, mimetics and conjugates), nucleic acids encoding these antibodies, host cells used to make the antibodies, methods of making the antibodies, and pharmaceutical compositions comprising the antibodies and optionally a pharmaceutical carrier, methods of treatment and diagnosis comprising the use of the antibodies and the use of the antibodies for the treatment of cancers.

LY75 Proteins

Lymphocyte antigen 75 acts as an endocytic receptor to direct captured antigens from the extracellular space to a specialized antigen-processing compartment and is thought to cause a reduction in proliferation of B-lymphocytes.

According to SWISS-PROT, Lymphocyte antigen 75 is expressed in spleen, thymus, colon and peripheral blood lymphocytes. It has been detected in myeloid and B lymphoid cell lines. Isoforms designated herein OGTA076b and OGTA076c are expressed in malignant Hodgkin's lymphoma cells called Hodgkin's and Reed-Sternberg (HRS) cells. LY75 acts as an endocytic receptor to direct captured antigens from the extracellular space to a specialized antigen-processing compartment. It causes reduced proliferation of B-lymphocytes.

Expression of LY75 has been observed in pancreatic, bladder, ovarian, breast (including triple negative), colorectal, esophageal, skin, thyroid and lung (non-small-cell) cancers as well as Multiple Myeloma and many different subtypes of lymphomas (including DLBCL) and leukaemias.

The antibody of the invention may, in certain cases, cross-react with the LY75 from species other than human. For example, to facilitate clinical testing, the antibodies of the invention may cross react with murine or primate LY75 molecules. Alternatively, in certain embodiments, the antibodies may be completely specific for human LY75 and may not exhibit species or other types of non-human cross-reactivity.

Antibodies

The present invention provides anti-LY75 antibodies, generally therapeutic and/or diagnostic antibodies as described herein. Antibodies that find use in the present invention can take on a number of formats as described herein, including traditional antibodies as well as antibody derivatives, fragments and mimetics, described below. In one embodiment, the invention provides antibody structures that contain a set of 6 CDRs as defined herein (including small numbers of amino acid changes as described below).

"Antibody" as used herein includes a wide variety of structures, as will be appreciated by those in the art, that in some embodiments contain at a minimum a set of 6 CDRs as defined herein; including, but not limited to traditional antibodies (including both monoclonal and polyclonal antibodies), humanized and/or chimeric antibodies, antibody fragments, engineered antibodies (e.g. with amino acid modifications as outlined below), multispecific antibodies (including bispecific antibodies), and other analogs known in the art.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Thus, "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. It should be understood that therapeutic antibodies can also comprise hybrids of any combination of isotypes and/or subclasses.

In many embodiments, IgG isotypes are used in the present invention, with IgG1 finding particular use in a number of applications.

The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

Throughout the present specification, the Kabat numbering system is generally used when referring to a residue in the variable domain (approximately, residues 1-107 of the light chain variable region and residues 1-113 of the heavy chain variable region) (e.g, Kabat et al., supra (1991)).

The CDRs contribute to the formation of the antigen-binding, or more specifically, epitope binding site of antibodies. The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. As described herein, methods for determining what epitopes are bound by a given antibody (i.e., epitope mapping) are well known in the art and include, for example, immunoblotting and immunoprecipitation assays, wherein overlapping or contiguous peptides from LY75 are tested for reactivity with the given anti-LY75 antibody. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)). The term "epitope mapping" refers to the process of identification of the molecular determinants for antibody-antigen recognition.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al.).

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230.

Of particular interest in the present invention are the Fc regions. By "Fc" or "Fc region" or "Fc domain" as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, the last three constant region immunoglobulin domains of IgE and IgM, and the flexible hinge N-terminal to these domains. For IgA and IgM, Fc may include the J chain. For IgG, the Fc domain comprises immunoglobulin domains Cγ2 and Cγ3 (Cγ2 and Cγ3) and the lower hinge region between Cγ1 (Cγ1) and Cγ2 (Cγ2). Although the boundaries of the Fc region may vary, the human IgG heavy chain Fc region is usually defined to include residues C226 or P230 to its carboxyl-terminus, wherein the numbering is according to the EU index as in Kabat. In some embodiments, as is more fully described below, amino acid modifications are made to the Fc region, for example to alter binding to one or more FcγR receptors or to the FcRn receptor.

In some embodiments, the antibodies are full length. By "full length antibody" herein is meant the structure that constitutes the natural biological form of an antibody, including variable and constant regions, including one or more modifications as outlined herein.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively. Structures that rely on the use of a set of CDRs are included within the definition of "antibody".

In one embodiment, the antibody is an antibody fragment. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable region, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all entirely incorporated by reference).

Chimeric and Humanized Antibodies

In some embodiments, the antibody can be a mixture from different species, e.g. a chimeric antibody and/or a humanized antibody. That is, in the present invention, the CDR sets can be used with framework and constant regions other than those specifically described by sequence herein.

In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

In one embodiment, the antibodies of the invention can be multispecific antibodies, and notably bispecific antibodies, also sometimes referred to as "diabodies". These are antibodies that bind to two (or more) different antigens, or different epitopes on the same antigen. Diabodies can be manufactured in a variety of ways known in the art (Holliger and Winter, 1993, Current Opinion Biotechnol. 4:446-449, entirely incorporated by reference), e.g., prepared chemically or from hybrid hybridomas.

In one embodiment, the antibody is a minibody. Minibodies are minimized antibody-like proteins comprising a scFv joined to a CH3 domain. Hu et al., 1996, Cancer Res. 56:3055-3061, entirely incorporated by reference. In some cases, the scFv can be joined to the Fc region, and may include some or the entire hinge region. It should be noted that minibodies are included within the definition of "antibody" despite the fact it does not have a full set of CDRs.

The antibodies of the present invention are generally isolated or recombinant. "Isolated," when used to describe the various polypeptides disclosed herein, means a polypeptide that has been identified and separated and/or recovered from a cell or cell culture from which it was expressed. Thus an isolated antibody is intended to refer to an antibody that is substantially free of other antibodies having different antigenic specificities (e.g. an isolated antibody that specifically binds to the LY75 is substantially free of antibodies that specifically bind antigens other than the LY75). Thus, an "isolated" antibody is one found in a form not normally found in nature (e.g. non-naturally occurring). An isolated antibody as defined herein may, in one embodiment, include at least one amino acid which does not occur in the "naturally" occurring antibody. This amino acid may be introduced by way of an addition or a substitution. It will be understood that the introduced amino acid may be a naturally occurring or non-naturally occurring amino acid. In some embodiments, the antibodies of the invention are recombinant proteins, isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. In the case of recombinant proteins, the definition includes the production of an antibody in a wide variety of organisms and/or host cells that are known in the art in which it is not naturally produced. Ordinarily, an isolated polypeptide will be prepared by at least one purification step. An "isolated antibody," refers to an antibody which is substantially free of other antibodies having different antigenic specificities. For instance, an isolated antibody that specifically binds to LY75 is substantially free of antibodies that specifically bind antigens other than LY75.

Isolated monoclonal antibodies, having different specificities, can be combined in a well-defined composition. Thus for example, the antibody of the invention can optionally and individually be included or excluded in a formulation, as is further discussed below.

The anti-LY75 antibodies of the present invention specifically bind LY75 (e.g. SEQ ID No: 15). "Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a $K_D$ for an antigen or epitope of at least about $10^{-4}$ M, at least about $10^{-5}$ M, at least about $10^{-8}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where $K_D$ refers to a dissociation rate of a particular antibody-antigen interaction. Typically, an antibody that specifically binds an antigen will have a $K_D$ that is 20-, 50-, 100-, 500-, 1000-, 5,000-, 10,000- or more times greater for a control molecule relative to the antigen or epitope. However, in the present invention, when administering ADCs of the LY75 antibodies of the invention, what is important is that the $K_D$ is sufficient to allow internalization and thus cell death without significant side effects.

Also, specific binding for a particular antigen or an epitope can be exhibited, for example, by an antibody having a $K_A$ or $K_a$ for an antigen or epitope of at least 20-, 50-, 100-, 500-, 1000-, 5,000-, 10,000- or more times greater for the epitope relative to a control, where $K_A$ or $K_a$ refers to an association rate of a particular antibody-antigen interaction.

Standard assays to evaluate the binding ability of the antibodies toward LY75 can be done on the protein or cellular level and are known in the art, including for example, ELISAs, Western blots, RIAs, BIAcore® assays and flow cytometry analysis. Suitable assays are described in detail in the Examples. The binding kinetics (e.g. binding affinity) of the antibodies also can be assessed by standard assays known in the art, such as by Biacore® system analysis. To assess binding to Raji or Daudi B cell tumor cells, Raji (ATCC Deposit No. CCL-86) or Daudi (ATCC Deposit No. CCL-213) cells can be obtained from publicly available sources, such as the American Type Culture Collection, and used in standard assays, such as flow cytometric analysis.

LY75 Antibodies

The present invention provides LY75 antibodies that bind to LY75 (SEQ ID No: 15) and maybe internalized when contacted with cells expressing LY75 on the cell surface or may elicit an ADCC response in the presence of effector cells or elicit a cytotoxic T-cell response in the presence of effector cells. These antibodies are referred to herein either as "anti-LY75" antibodies or, for ease of description, "LY75 antibodies".

The LY75 antibodies are internalized upon contact with cells, particularly tumor cells, which express LY75 on the surface. That is, LY75 antibodies as defined herein that also comprise drug conjugates are internalized by tumor cells, resulting in the release of the drug and subsequent cell death, allowing for treatment of cancers that exhibit LY75 expression. Internalization in this context can be measured in several ways. In one embodiment, the LY75 antibodies of the invention are contacted with cells, such as a cell line as outlined herein, using standard assays such as MAbZap. It would be clear to the skilled person that the MabZap assay is representative of the effect that would be expected to be seen with an antibody-drug conjugate (ADC). In the latter case, the ADC would be internalized, thus taking the drug into the cell. A toxic drug would have the capacity to kill the cell, i.e. to kill the targeted cancer cell. Data from MabZap assays are readily accepted by persons of skill in the art to be representative of ADC assays (Kohls, M and Lappi, D., [2000] Biotechniques, vol. 28, no. 1, 162-165).

In these in vitro assay embodiments, the LY75 antibodies of the invention are added, along with an anti-LY75 antibody comprising a toxin; for example, the LY75 antibody may be murine or humanized and the anti-LY75 antibody can be anti-murine or anti-humanized and contain a toxin such as saporin. Upon formation of the [LY75 antibody of the invention]-[anti-LY75 antibody-drug conjugate] complex, the complex is internalized and the drug (e.g. saporin) is released, resulting in cell death. Only upon internalization does the drug get released, and thus cells remain viable in the absence of internalization. As outlined below, without being bound by theory, in therapeutic applications, the anti-LY75 antibody contains the toxin, and upon internalization, the bond between the antibody and the toxin is cleaved, releasing the toxin and killing the cell.

In addition, the LY75 antibodies elicit an ADCC response in the presence of effector cells, particularly tumor cells, that express LY75 on the surface.

In one embodiment, the antibody comprises the heavy and light chain complementarity determining regions (CDRs) or variable regions (VRs) of the particular antibody described herein (e.g., referred to herein as "LY75_A1"). Accordingly, in one embodiment, the antibody comprises the CDR1, CDR2, and CDR3 domains of the heavy chain variable (VH) region of antibody LY75_A1 having the sequence shown in SEQ ID NO:1, and the CDR1, CDR2 and CDR3 domains of the light chain variable (VL) region of antibody LY75_A1 having the sequence shown in SEQ ID NO:2.

In another embodiment, the antibody comprises a heavy chain variable region comprising a first vhCDR comprising SEQ ID NO: 5; a second vhCDR comprising SEQ ID NO: 6; and a third vhCDR comprising SEQ ID NO:7; and a light chain variable region comprising a first vlCDR comprising SEQ ID NO:8; a second vlCDR comprising SEQ ID NO: 9; and a third vlCDR comprising SEQ ID NO:10.

In another embodiment, the antibodies of the invention bind to human LY75 and include a heavy chain variable region comprising an amino acid sequence comprising SEQ ID NO:1, and conservative sequence modifications thereof. The antibody may further include a light chain variable region comprising an amino acid sequence comprising SEQ ID NO:2, and conservative sequence modifications thereof.

In a further embodiment, the antibodies of the invention bind to human LY75 and include a heavy chain variable region and a light chain variable region comprising the amino acid sequences set forth in SEQ ID NOs:1 and/or 2, respectively, and conservative sequence modifications thereof. As used herein, the term conservative sequence modification refers to, for example, the substitution of an amino acid with an amino acid having similar characteristics. It is common general knowledge for one skilled in the art what such substitutions may be considered conservative. Other modifications which can be considered to be conservative sequence modifications include, for example, glycosylation.

Isolated antibodies which include heavy and light chain variable regions having at least 80%, or at least 85%, or at least 90%, or at least 91%, or at least 92%, or at least 93%, or at least 94%, or at least 95%, or at least 96%, or at least 97%, or at least 98%, or at least 99%, or more sequence identity to any of the above sequences are also included in the present invention. Ranges intermediate to the above-recited values, e.g., heavy and light chain variable regions having at least 80-85%, 85-90%, 90-95% or 95-100% sequence identity to any of the above sequences are also intended to be encompassed by the present invention. In one embodiment, the antibody comprises a heavy chain variable region comprising SEQ ID NO:1 or a sequence that is at least 90%, at least 91%, at least 92%, at least 93%, at least 94%, at least 95%, at least 96%, at least 97%, at least 98%, at least 99% identical to SEQ ID NO: 1. In another embodiment, the antibody comprises a light chain variable region comprising SEQ ID NO:2 or a sequence that is at least 90%, at least 91%, at least 92%, at least 93%, at least 94%, at least 95%, at least 96%, at least 97%, at least 98%, at least 99% identical to SEQ ID NO: 2. In another embodiment, the antibody comprises a heavy chain framework region comprising an amino acid sequence that is at least 90%, at least 91%, at least 92%, at least 93%, at least 94%, at least 95%, at least 96%, at least 97%, at least 98%, at least 99% identical to the framework of the heavy chain variable region of SEQ ID NO: 1 comprising SEQ ID NOs: 16, 17 and 18. In another embodiment, the antibody comprises a light chain framework region comprising an amino acid sequence that is at least 90%, at least 91%, at least 92%, at least 93%, at least 94%, at least 95%, at least 96%, at least 97%, at least 98%, at least 99% identical to the framework of the light chain variable region of SEQ ID NO:2 comprising SEQ ID NOs:19, 20 and 21.

In one embodiment, the antibody of the invention is an anti-LY75 antibody (referred to herein as "LY75_A1 antibody") comprising the following CDRs, as well as variants containing a limited number of amino acid variants:

| A1 | SEQ ID NOs |
|---|---|
| variable heavy CDR1 | 5 |
| variable heavy CDR2 | 6 |
| variable heavy CDR3 | 7 |
| variable light CDR1 | 8 |
| variable light CDR2 | 9 |
| variable light CDR3 | 10 |

Disclosed herein are also variable heavy and light chains that comprise the CDR sets of the invention, as well as full length heavy and light chains (e.g. comprising constant regions as well). As will be appreciated by those in the art, the CDR sets of the invention can be incorporated into murine, humanized or human constant regions (including framework regions). Accordingly, the present invention provides variable heavy and light chains that are at least about 90%-99% identical to the SEQ IDs disclosed herein, with 90, 91, 92, 93, 94, 95, 96, 97, 98 and 99% all finding use in the present invention.

Antibodies that Bind to the Same Epitope as the LY75 Antibodies of the Invention In another embodiment, the invention provides antibodies that bind to the same epitope on the human LY75 as any of the LY75 monoclonal antibodies of the invention. The term "binds to the same epitope" with reference to two or more antibodies means that the antibodies compete for binding to an antigen and bind to the same, overlapping or encompassing continuous or discontinuous segments of amino acids. Those of skill in the art understand that the phrase "binds to the same epitope" does not necessarily mean that the antibodies bind to exactly the same amino acids, although in one embodiment it can be defined as such. In another embodiment, the precise amino acids to which the antibodies bind can differ. For example, a first antibody can bind to a segment of amino acids that is completely encompassed by the segment of amino acids bound by a second antibody. In another example, a first antibody binds one or more segments of amino acids that significantly overlap the one or more segments bound by the second antibody. For the purposes herein, such antibodies are considered to "bind to the same epitope."

Accordingly, also, encompassed by the present invention in one embodiment are antibodies that bind to an epitope on LY75 which comprises all or a portion of an epitope recognized by the particular antibodies described herein (e.g., the same or an overlapping region or a region between or spanning the region). Also encompassed by the present invention, are antibodies that bind specifically to at least one, for example, 2, 3, 4, 5, 6, 7, 8, 9 or 10, peptide(s) selected from the group comprising SEQ ID NOs: 24, 25, 26, 27, 28, 29, 30, 31, 32, 33, 34, 35, 36 or 37 or a fragment thereof, wherein said fragment comprises at least 2, at least 3, at least 4, at least 5, at least 6, at least 7, at least 8, at least 9 or at least 10 contiguous amino acids. In a further embodiment, the epitope recognized by the antibodies of the present invention comprises at least one peptide, at least two or at least three peptides selected from the group consisting of SEQ ID NOs: 27, 29, 30, 34, 35, 36 or 37 or fragments thereof wherein said fragments comprises at least 2, at least 3, at least 4, at least 5, at least 6, at least 7, at least 8, at least 9 or at least 10 contiguous amino acids. In a further embodiment, the epitope recognized by the antibodies of the present invention comprises at least one peptides, for example, one, two or three peptides selected from the group consisting of SEQ ID NOs: 30, 36 and 37 or fragments thereof, wherein said fragments comprises at least 2, at least 3, at least 4, at least 5, at least 6, at least 7, at least 8, at least 9 or at least 10 contiguous amino acids.

Also encompassed by the present invention are antibodies that bind the same epitope and/or antibodies that compete for binding to human LY75 with the antibodies described herein. Antibodies that recognize the same epitope or compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen, such as LY75. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al, *J. Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., *Mol. Immunol.* 25(1):7 (1988)); solid phase direct biotin-avidin EIA (Cheung et al, *Virology* 176:546 (1990)); and direct labeled RIA. (Moldenhauer et al., *Scand. J. Immunol* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% 75-80% 80-85% 85-90% 90-95% 95-99% or more.

Other techniques include, for example, epitope mapping methods, such as, x-ray analyses of crystals of antigen: antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

In a particular embodiment, the antibody competes for binding to LY75 with an antibody comprising heavy and/or light chain variable regions comprising the amino acid sequences set forth in SEQ ID NOs:1 and 2, respectively, or amino acid sequences at least 80%, at least 85%, at least 90%, at least 95%, at least 96%, at least 97%, at least 98% or at least 99% identical thereto. In another embodiment, the antibody competes for binding to LY75 with an antibody comprising heavy and/or light chain variable regions comprising the amino acid sequences set forth in SEQ ID NOs:1 and 2 (LY75_A1).

Other antibodies of the invention bind to an epitope on LY75 recognized by the antibodies described herein. In another particular embodiment, the antibody binds to an epitope on LY75 recognized by an antibody comprising heavy and/or light chain variable regions comprising the amino acid sequences set forth in SEQ ID NOs:1 and 2, respectively, or amino acid sequences at least 80%, at least 85%, at least 90%, at least 95%, at least 96%, at least 97%, at least 98% or at least 99% identical thereto. In another embodiment, the antibody binds to an epitope on LY75 recognized by an antibody comprising heavy and/or light chain variable regions comprising the amino acid sequences set forth in SEQ ID NOs:1 and 2 (LY75).

Characterization of Monoclonal Antibodies to LY75

Monoclonal antibodies of the invention can be characterized for binding to LY75 using a variety of known techniques. Generally, the antibodies are initially characterized by ELISA. Briefly, microtiter plates can be coated with purified LY75 in PBS, and then blocked with irrelevant proteins such as bovine serum albumin (BSA) diluted in PBS. Dilutions of plasma from LY75-immunized mice are added to each well and incubated for 1-2 hours at 37° C. The plates are washed with PBS/Tween 20 and then incubated with a goat-anti-human IgG Fc-specific polyclonal reagent conjugated to alkaline phosphatase for 1 hour at 37° C. After washing, the plates are developed with ABTS substrate, and analyzed at OD of 405. Preferably, mice which develop the highest titers will be used for fusions.

An ELISA assay as described above can be used to screen for antibodies and, thus, hybridomas that produce antibodies that show positive reactivity with the LY75 immunogen. Hybridomas that bind, preferably with high affinity, to LY75 can then be sub cloned and further characterized. One clone from each hybridoma, which retains the reactivity of the parent cells (by ELISA), can then be chosen for making a cell bank, and for antibody purification.

To purify anti-LY75 antibodies, selected hybridomas can be grown in roller bottles, two-liter spinner-flasks or other culture systems. Supernatants can be filtered and concentrated with affinity chromatography with protein A-Sepharose (Pharmacia, Piscataway, N.J.) to purify the protein. After buffer exchange to PBS, the concentration can be determined by $OD_{280}$ using 1.43 extinction coefficient or preferably by nephelometric analysis. IgG can be checked by gel electrophoresis and by antigen specific method.

To determine if the selected anti-LY75 monoclonal antibodies bind to unique epitopes, each antibody can be biotinylated using commercially available reagents (Pierce, Rockford, Ill.). Biotinylated MAb binding can be detected with a streptavidin labeled probe. To determine the isotype of purified antibodies, isotype ELISAs can be performed using art recognized techniques. For example, wells of microtiter plates can be coated with 10 µg/ml of anti-Ig overnight at 4° C. After blocking with 5% BSA, the plates are reacted with 10 µg/ml of monoclonal antibodies or purified isotype controls, at ambient temperature for two hours. The wells can then be reacted with either IgGI or other isotype specific conjugated probes. Plates are developed and analyzed as described above.

To test the binding of monoclonal antibodies to live cells expressing LY75, flow cytometry can be used. Briefly, cell lines and/or human PBMCs expressing membrane-bound LY75 (grown under standard growth conditions) are mixed with various concentrations of monoclonal antibodies in PBS containing 0.1% BSA at 4° C. for 1 hour. After washing, the cells are reacted with Fluorescein-labeled anti-IgG antibody under the same conditions as the primary antibody staining. The samples can be analyzed by FACScan instrument using light and side scatter properties to gate on single cells and binding of the labeled antibodies is determined. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-LY75 IgGs can be further tested for reactivity with the LY75 antigen by Western blotting. Briefly, cell extracts from cells expressing LY75 can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. IgG binding can be detected using anti-IgG alkaline phosphatase and developed with BCIP/NBT substrate tablets (Sigma Chem. Co., St. Louis, Mo.).

Methods for analyzing binding affinity, cross-reactivity, and binding kinetics of various anti-LY75 antibodies include standard assays known in the art, for example, Biacore™ surface plasmon resonance (SPR) analysis using a Biacore™ 2000 SPR instrument (Biacore AB, Uppsala, Sweden.

In one embodiment, the antibody specifically binds to human LY75 comprising SEQ ID NO:15) Preferably, an antibody of the invention binds to human LY75 with high affinity.

Preferably, an antibody of the invention binds to a LY75 protein with a $K_D$ of $5 \times 10^{-8}$ M or less, binds to a LY75 protein with a $K_D$ of $2 \times 10^{-8}$ M or less, binds to a LY75 protein with a $K_D$ of $5 \times 10^{-9}$ M or less, binds to a LY75 protein with a $K_D$ of $4 \times 10^{-9}$ M or less, binds to a LY75 protein with a $K_D$ of $3 \times 10^{-9}$ M or less, binds to a LY75 protein with a $K_D$ of $2 \times 10^{-9}$ M or less, binds to a LY75 protein with a $K_D$ of $1 \times 10^{-9}$ M or less, binds to a LY75 protein with a $K_D$ of $5 \times 10^{-10}$ M or less, or binds to a LY75 protein with a $K_D$ of $1 \times 10^{-10}$ M or less.

In one embodiment, antibodies of the invention compete (e.g., cross-compete) for binding to LY75 with the particular anti-LY75 antibodies described herein (e.g., _LY75_A1). Such competing antibodies can be identified based on their ability to competitively inhibit binding to LY75 of one or more of mAbs in standard LY75 binding assays. For example, standard ELISA assays can be used in which a recombinant human LY75 protein is immobilized on the plate, one of the antibodies is fluorescently labeled and the ability of non-labeled antibodies to compete off the binding of the labeled antibody is evaluated. Additionally or alternatively, BIAcore analysis can be used to assess the ability of the antibodies to cross-compete. The ability of a test antibody to inhibit the binding of an anti-LY75 antibody of the invention to human LY75 demonstrates that the test antibody can compete with the antibody for binding to human LY75.

In one embodiment, the competing antibody is an antibody that binds to the same epitope on human LY75 as the particular anti-LY75 monoclonal antibodies described herein (e.g., LY75_A1). Standard epitope mapping techniques, such as x-ray crystallography and 2-dimensional nuclear magnetic resonance, can be used to determine whether an antibody binds to the same epitope as a reference antibody (see, e.g., Epitope Mapping Protocols in Methods in Molecular Biology, Vol. 66, G. E. Morris, Ed. (1996)).

In one embodiment, the antibody that competes for binding to LY75 and/or binds to the same epitope on human LY75 is a human antibody.

Once a single, archetypal anti-LY75 mAb has been isolated that has the desired properties described herein, other mAbs with similar properties, e.g., having the same epitope may be generated. For example, mice may be immunized with LY75 as described herein, hybridomas produced, and the resulting mAbs screened for the ability to compete with the archetypal mAb for binding to LY75. Mice can also be immunized with a smaller fragment of LY75 containing the epitope to which the archetypal mAb binds. The epitope can be localized by, e.g., screening for binding to a series of overlapping peptides spanning LY75. Alternatively, the method of Jespers et al., Biotechnology 12:899, 1994 may be used to guide the selection of mAbs having the same epitope and therefore similar properties to the archetypal mAb. Using phage display, first the heavy chain of the archetypal antibody is paired with a repertoire of (preferably human) light chains to select a LY75-binding mAb, and then the new light chain is paired with a repertoire of (preferably human) heavy chains to select a (preferably human) LY75-binding mAb having the same epitope as the archetypal mAb. Alternatively variants of the archetypal mAb can be obtained by mutagenesis of cDNA encoding the heavy and light chains of the antibody.

Epitope mapping, e.g., as described in Champe et al. (1995) J. Biol. Chem. 270:1388-1394, can be performed to determine whether the antibody binds an epitope of interest. "Alanine scanning mutagenesis," as described by Cunningham and Wells (1989) Science 244: 1081-1085, or some other form of point mutagenesis of amino acid residues in human LY75 may also be used to determine the functional epitope for an anti-LY75 antibody of the present invention. Mutagenesis studies, however, may also reveal amino acid residues that are crucial to the overall three-dimensional structure of LY75 but that are not directly involved in antibody-antigen contacts, and thus other methods may be necessary to confirm a functional epitope determined using this method.

The epitope bound by a specific antibody may also be determined by assessing binding of the antibody to peptides comprising fragments of human LY75. A series of overlapping peptides encompassing the sequence of LY75 may be synthesized and screened for binding, e.g. in a direct ELISA, a competitive ELISA (where the peptide is assessed for its ability to prevent binding of an antibody to LY75 bound to a well of a microtiter plate), or on a chip. Such peptide screening methods may not be capable of detecting some discontinuous functional epitopes, i.e. functional epitopes that involve amino acid residues that are not contiguous along the primary sequence of the LY75 polypeptide chain.

The epitope bound by antibodies of the present invention may also be determined by structural methods, such as X-ray crystal structure determination (e.g., WO2005/044853), molecular modeling and nuclear magnetic resonance (NMR) spectroscopy, including NMR determination of the H-D exchange rates of labile amide hydrogens in LY75 when free and when bound in a complex with an antibody of interest (Zinn-Justin et al. (1992) Biochemistry 31, 11335-11347; Zinn-Justin et al. (1993) Biochemistry 32, 6884-6891).

With regard to X-ray crystallography, crystallization may be accomplished using any of the known methods in the art (e.g. Giege et al. (1994) Acta Crystallogr. D50:339-350; McPherson (1990) Eur. J. Biochem. 189:1-23), including microbatch (e.g. Chayen (1997) Structure 5:1269-1274), hanging-drop vapor diffusion (e.g. McPherson (1976) J. Biol. Chem. 251:6300-6303), seeding and dialysis. It is desirable to use a protein preparation having a concentration of at least about 1 mg/mL and preferably about 10 mg/mL to about 20 mg/mL. Crystallization may be best achieved in a precipitant solution containing polyethylene glycol 1000-20,000 (PEG; average molecular weight ranging from about 1000 to about 20,000 Da), preferably about 5000 to about 7000 Da, more preferably about 6000 Da, with concentrations ranging from about 10% to about 30% (w/v). It may also be desirable to include a protein stabilizing agent, e.g. glycerol at a concentration ranging from about 0.5% to about 20%. A suitable salt, such as sodium chloride, lithium chloride or sodium citrate may also be desirable in the precipitant solution, preferably in a concentration ranging from about 1 mM to about 1000 mM. The precipitant is preferably buffered to a pH of from about 3.0 to about 5.0, preferably about 4.0. Specific buffers useful in the precipitant solution may vary and are well-known in the art (Scopes, Protein Purification: Principles and Practice, Third ed., (1994) Springer-Verlag, New York). Examples of useful buffers include, but are not limited to, HEPES, Tris, MES and acetate. Crystals may be grow at a wide range of temperatures, including 2° C., 4° C., 8° C. and 26° C.

Antibody:antigen crystals may be studied using well-known X-ray diffraction techniques and may be refined using computer software such as X-PLOR (Yale University, 1992, distributed by Molecular Simulations, Inc.; see e.g. Blundell & Johnson (1985) Meth. Enzymol. 114 & 115, H. W. Wyckoff et al., eds., Academic Press; U.S. Patent Application Publication No. 2004/0014194), and BUSTER (Bricogne (1993) Acta Cryst. D49:37-60; Bricogne (1997) Meth. Enzymol. 276A:361-423, Carter & Sweet, eds.; Roversi et al. (2000) Acta Cryst. D56:1313-1323), the disclosures of which are hereby incorporated by reference in their entireties.

Antibody competition assays, as described herein, can be used to determine whether an antibody "binds to the same epitope" as another antibody. Typically, competition of 50% or more, 60% or more, 70% or more, such as 70%, 71%, 72%, 73%, 74%, 75%, 80%, 85%, 90%, 95%, 96%, 97%, 98%, 99% or more, of an antibody known to interact with the epitope by a second antibody under conditions in which the second antibody is in excess and the first saturates all sites, is indicative that the antibodies "bind to the same epitope." To assess the level of competition between two antibodies, for example, radioimmunoassays or assays using other labels for the antibodies, can be used. For example, a LY75 antigen can be incubated with a saturating amount of a first anti-LY75 antibody or antigen-binding fragment thereof conjugated to a labeled compound (e.g., $^3$H, $^{125}$I, biotin, or rubidium) in the presence the same amount of a second unlabeled anti-LY75 antibody. The amount of labeled antibody that is bound to the antigen in the presence of the unlabeled blocking antibody is then assessed and compared to binding in the absence of the unlabeled blocking antibody. Competition is determined by the percentage change in binding signals in the presence of the unlabeled blocking antibody compared to the absence of the blocking antibody. Thus, if there is a 50% inhibition of binding of the labeled antibody in the presence of the blocking antibody compared to binding in the absence of the blocking antibody, then there is competition between the two antibodies of 50%. Thus, reference to competition between a first and second antibody of 50% or more, 60% or more, 70% or more, such as 70%, 71%, 72%, 73%, 74%, 75%, 80%, 85%, 90%, 95%, 96%, 97%, 98%, 99% A or more, means that the first antibody inhibits binding of the second antibody (or vice versa) to the antigen by 50%, 60%, 70%, 71%, 72%, 73%, 74%, 75%, 80%, 85%, 90%, 95%, 96%, 97%, 98%, 99% A or more (compared to binding of the antigen by the second antibody in the absence of the first antibody). Thus, inhibition of binding of a first antibody to an antigen by a second antibody of 50%, 605, 70%, 71%, 72%, 73%, 74%, 75%, 80%, 85%, 90%, 95%, 96%, 97%, 98%, 99% A or more indicates that the two antibodies bind to the same epitope.

Antibody Modifications

The present invention further provides variant antibodies, sometimes referred to as "antibody derivatives" or "antibody analogs" as well. That is, there are a number of modifications that can be made to the antibodies of the invention, including, but not limited to, amino acid modifications in the CDRs (affinity maturation), amino acid modifications in the framework regions, amino acid modifications in the Fc region, glycosylation variants, covalent modifications of other types (e.g. for attachment of drug conjugates, etc.).

By "variant" herein is meant a polypeptide sequence that differs from that of a parent polypeptide by virtue of at least one amino acid modification. In this case, the parent polypeptide is either the full length variable heavy or light chains, listed in SEQ ID Nos: 1 or 2, respectively or the CDR regions or the framework regions of the heavy and light chains listed in SEQ ID NOs 5-10 and 16-21. Amino acid modifications can include substitutions, insertions and deletions, with the former being preferred in many cases. It will be understood that an amino acid substitution may be a conservative or non-conservative substitution with conservative substitutions being preferred. Further said substitution may be a substitution with either a naturally or non-naturally occurring amino acid.

In general, variants can include any number of modifications, as long as the function of the antibody is still present, as described herein. That is, LY75_A1, for example, the antibody should still specifically bind to human LY75. Similarly, if amino acid variants are generated with the Fc region, for example, the variant antibodies should maintain the required receptor binding functions for the particular application or indication of the antibody.

"Variants" in this case can be made in either the listed CDR sequences, the framework or Fc regions of the antibody.

However, in general, from 1, 2, 3, 4, 5, 6, 7, 8, 9 or 10 amino acid substitutions are generally utilized as often the goal is to alter function with a minimal number of modifications. In some cases, there are from 1 to 5 modifications (e.g. individual amino acid substitutions, insertions or deletions), with from 1-2, 1-3 and 1-4 also finding use in many embodiments. The number of modifications can depend on the size of the region being modified; for example, in general, fewer modifications are desired in CDR regions. It will be understood by the skilled person that even within the CDR regions the location of the modification can significantly alter the effect. In one embodiment, the modifications can be made in any of CDR1, CDR2 or CDR3 of the heavy and/or light chains. In a further embodiment, the modifications are made in any of CDR1 or CDR2 of the heavy and/or light chains. In a still further embodiment, the modifications are located in CDR1 of the heavy and/or light chains.

It should be noted that the number of amino acid modifications may be within functional domains: for example, it may be desirable to have from 1-5 modifications in the Fc region of wild-type or engineered proteins, as well as from 1 to 5 modifications in the Fv region, for example. A variant polypeptide sequence will preferably possess at least about 80%, 85%, 90%, 91%, 92%, 93%, 94%, 95%, 96%, 97%, 98% or 99% A identity to the parent sequences (e.g. the variable regions, the constant regions, and/or the heavy and light chain sequences and/or the CDRs of LY75_A1). It should be noted that depending on the size of the sequence, the percent identity will depend on the number of amino acids.

By "amino acid substitution" or "substitution" herein is meant the replacement of an amino acid at a particular position in a parent polypeptide sequence with another amino acid which may be a natural or non-naturally occurring amino acid. For example, the substitution S100A refers to a variant polypeptide in which the serine at position 100 is replaced with alanine. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

By "parent polypeptide", "parent protein", "precursor polypeptide", or "precursor protein" as used herein is meant an unmodified polypeptide that is subsequently modified to generate a variant. In general, the parent polypeptides herein are LY75_A1. Accordingly, by "parent antibody" as used herein is meant an antibody that is modified to generate a variant antibody.

By "wild type" or "WT" or "native" herein is meant an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified.

By "variant Fc region" herein is meant an Fc sequence that differs from that of a wild-type Fc sequence by virtue of at least one amino acid modification. Fc variant may refer to the Fc polypeptide itself, compositions comprising the Fc variant polypeptide, or the amino acid sequence.

In some embodiments, one or more amino acid modifications are made in one or more of the CDRs of LY75_A1. In general, only 1 or 2 or 3 amino acids are substituted in any single CDR, and generally no more than from 4, 5, 6, 7, 8 9 or 10 changes are made within a set of 6 CDRs. However, it should be appreciated that any combination of no substitutions, 1, 2 or 3 substitutions in any CDR can be independently and optionally combined with any other substitution. It will be apparent that substitutions can be made in any of the 6 CDRs. In one embodiment, substitutions are made in CDR1 of the heavy and/or light chains.

In some cases, amino acid modifications in the CDRs are referred to as "affinity maturation". An "affinity matured" antibody is one having one or more alteration(s) in one or more CDRs which results in an improvement in the affinity of the antibody for antigen, compared to a parent antibody which does not possess those alteration(s). In some cases, although rare, it may be desirable to decrease the affinity of an antibody to its antigen, but this is generally not preferred.

Affinity maturation can be done to increase the binding affinity of the antibody for the antigen by at least about 10%, about 20%, about 30%, about 40%, about 50%, about 60%, about 70%, about 80%, about 90%, about 100%, about 110%, about 120%, about 130%, about 140%, about 150% or more, or 1, 2, 3, 4 to 5 fold as compared to the "parent" antibody. Preferred affinity matured antibodies will have nanomolar or even picomolar affinities for the target antigen. Affinity matured antibodies are produced by known procedures. See, for example, Marks et al., 1992, Biotechnology 10:779-783 that describes affinity maturation by variable heavy chain (VH) and variable light chain (VL) domain shuffling. Random mutagenesis of CDR and/or framework residues is described in: Barbas, et al. 1994, Proc. Nat. Acad. Sci, USA 91:3809-3813; Shier et al., 1995, Gene 169:147-155; Yelton et al., 1995, J. Immunol. 155:1994-2004; Jackson et al., 1995, J. Immunol. 154(7):3310-9; and Hawkins et al, 1992, J. Mol. Biol. 226:889-896, for example.

Alternatively, amino acid modifications can be made in one or more of the CDRs of the antibodies of the invention that are "silent", e.g. that do not significantly alter the affinity of the antibody for the antigen. These can be made for a number of reasons, including optimizing expression (as can be done for the nucleic acids encoding the antibodies of the invention).

Thus, included within the definition of the CDRs and antibodies of the invention are variant CDRs and antibodies; that is, the antibodies of the invention can include amino acid modifications in one or more of the CDRs of LY75_A1. In addition, as outlined below, amino acid modifications can also independently and optionally be made in any region outside the CDRs, including framework and constant regions as described herein.

In some embodiments, the anti-LY75 antibodies of the invention are composed of a variant Fc domain. As is known in the art, the Fc region of an antibody interacts with a number of Fc receptors and ligands, imparting an array of important functional capabilities referred to as effector functions. These Fc receptors include, but are not limited to, (in humans) FcγRI (CD64) including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158, correlated to antibody-dependent cell cytotoxicity (ADCC)) and FcγRIIIb (including allotypes FcγRIIIb-NA1 and FcγRIIIb-NA2), FcRn (the neonatal receptor), C1q (complement protein involved in complement dependent cytotoxicity (CDC)) and FcRn (the neonatal receptor involved in serum half-life). Suitable modifications can be made at one or more positions as is generally outlined, for example in U.S. patent application Ser. No. 11/841,654 and references cited therein, US 2004/013210, US 2005/0054832, US 2006/0024298, US 2006/0121032, US 2006/0235208, US 2007/0148170, U.S. Ser. No. 12/341, 769, U.S. Pat. No. 6,737,056, U.S. Pat. No. 7,670,600, U.S. Pat. No. 6,086,875 all of which are expressly incorporated by reference in their entirety, and in particular for specific amino acid substitutions that increase binding to Fc receptors.

In addition to the modifications outlined above, other modifications can be made. For example, the molecules may be stabilized by the incorporation of disulphide bridges linking the VH and VL domains (Reiter et al., 1996, Nature Biotech. 14:1239-1245, entirely incorporated by reference).

In addition, modifications at cysteines are particularly useful in antibody-drug conjugate (ADC) applications, further described below. In some embodiments, the constant region of the antibodies can be engineered to contain one or more cysteines that are particularly "thiol reactive", so as to allow more specific and controlled placement of the drug moiety. See for example U.S. Pat. No. 7,521,541, incorporated by reference in its entirety herein.

In addition, there are a variety of covalent modifications of antibodies that can be made as outlined below.

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues may also be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole and the like.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using 125I or 131I to prepare labeled proteins for use in radioimmunoassay, the chloramine T method described above being suitable.

Carboxyl side groups (aspartyl or glutamyl) are selectively modified by reaction with carbodiimides (R'—N═C═N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antibodies to a water-insoluble support matrix or surface for use in a variety of methods, in addition to methods described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cynomolgusogen bromide-activated carbohydrates and the reactive substrates described in U.S. Pat. Nos. 3,969,287; 3,691,016; 4,195,128; 4,247,642; 4,229,537; and 4,330,440, all entirely incorporated by reference, are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, pp. 79-86 [1983], entirely incorporated by reference), acetylation of the N-terminal amine, and amidation of any C-terminal carboxyl group.

In addition, as will be appreciated by those in the art, labels (including fluorescent, enzymatic, magnetic, radioactive, etc. can all be added to the antibodies (as well as the other compositions of the invention).

Bispecific Molecules

In another aspect, the present invention features bispecific molecules comprising an anti-LY75 antibody, or a fragment thereof, of the invention. An antibody of the invention, or antigen-binding portions thereof, can be derivatized or linked to another functional molecule, e.g. another peptide or protein (e.g. another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g. by chemical coupling, genetic fusion, non-covalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for a first target epitope (i.e. LY75) and a second binding specificity for a second target epitope. The second target epitope maybe present on the same target protein as that bound by the first binding specificity; or the second target epitope may be present of a different target protein to that bound by the first protein to that bound by the first binding specificity. The second target epitope may be present on the same cell as the first target epitope (i.e. LY75); or the second target epitope may be present on a target which is not displayed by the cell which displays the first target epitope. As used herein, the term 'binding specificity' refers to a moiety comprising at least one antibody variable domain.

In a one embodiment of the invention, the second target epitope is an Fc receptor, e.g. human FcγRI (CD64) or a human Fcα receptor (CD89). Therefore, the invention includes bispecific molecules capable of binding both to FcγR or FcαR expressing effector cells (e.g. monocytes, macrophages or polymorphonuclear cells (PMNs), and to target cells expressing LY75. These bispecific molecules target LY75 expressing cells to effector cell and trigger Fc receptor-mediated effector cell activities, such as phagocytosis of LY75 expressing cells, antibody dependent cell-mediated cytotoxicity (ADCC), cytokine release, or generation of superoxide anion.

In another embodiment of the invention, the second target epitope is CD3 or CD5. Therefore, the invention includes bispecific molecules capable of binding both to CD3 or CD5 expressing effector cells (e.g. CD3 or CD5 expressing cytotoxic T cells), and to target cells expressing LY75. These bispecific molecules target LY75 expressing cells to effector cell and trigger CD3 or CD5-mediated effector cell activities, such as T cell clonal expansion and T cell cytotoxicity. In this embodiment, the bispecific antibody of the invention may have a total of either two or three antibody variable domains, wherein first portion of the bispecific antibody is capable of recruiting the activity of a human immune effector cell by specifically binding to an effector antigen located on the human immune effector cell, in which the effector antigen is the human CD3 antigen or the human CD5 antigen, said first portion consisting of one antibody variable domain, and a second portion of the bispecific antibody is capable of specifically binding to a target antigen other than the effector antigen e.g. LY75, said target antigen being located on a target cell other than said human immune effector cell, and said second portion comprising one or two antibody variable domains.

In an embodiment of the invention in which the bispecific molecule is multispecific, the molecule can further include a third binding specificity, in addition to an anti-Fc binding specificity or anti-CD3 or anti-CD5 binding specificity and an anti-LY75 binding specificity. In one embodiment, the third binding specificity is an anti-enhancement factor (EF) portion, e.g. a molecule which binds to a surface protein involved in cytotoxic activity and thereby increases the immune response against the target cell. The "anti-enhancement factor portion" can be an antibody, functional antibody fragment or a ligand that binds to a given molecule, e.g. an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g. an Fab, Fab', F(ab')$_2$, Fv, Fd, dAb or a single chain Fv. The antibody may also be a light chain or heavy chain dimer, or any minimal fragment thereof such as an Fv or a single chain construct as described in U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32), and FcγRIII (CD16). In one preferred embodiment, the Fcγ receptor is a human high affinity FcγRI. The human FcγRI is a 72 kDa molecule, which shows high affinity for monomeric IgG ($10^8$-$10^9$ $M^{-1}$).

The production and characterization of certain preferred anti-Fcγ monoclonal antibodies are described in PCT Publication WO 88/00052 and in U.S. Pat. No. 4,954,617, the teachings of which are fully incorporated by reference herein. These antibodies bind to an epitope of FcγRI, FcγRII or Fc γRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J. Immunol* 155 (10): 4996-5002 and PCT Publication WO 94/10332. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g. an Fc-alpha receptor [FcαRI (CD89)], the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5 \times 10^7$ $M^{-1}$) for both IgA1 and IgA2, which is increased upon exposure to cytokines such as G-CSF or GM-CSF [Morton, H. C. et al. (1996) *Critical Reviews in Immunology* 16:423-440]. Four FcαRI-specific monoclonal antibodies, identified as A3, A59, A62 and A77, which bind FcαRI outside the IgA ligand binding domain, have been described [Monteiro, R. C. et al. (1992) *J. Immunol.* 148:1764].

FcαRI and FcγRI are preferred trigger receptors for use in the bispecific molecules of the invention because they are (1) expressed primarily on immune effector cells, e.g. monocytes, PMNs, macrophages and dendritic cells; (2) expressed at high levels (e.g. 5,000-100,000 per cell); (3) mediators of cytotoxic activities (e.g. ADCC, phagocytosis); and (4) mediate enhanced antigen presentation of antigens, including self-antigens, targeted to them.

Antibodies which can be employed in the bispecific molecules of the invention are murine, human, chimeric and humanized monoclonal antibodies.

The bispecific molecules of the present invention can be prepared by conjugating the constituent binding specificities, e.g. the anti-FcR, anti-CD3 anti-CD5 and anti-LY75 binding specificities, using methods known in the art. For example, the binding specificity of each bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohexane-1-carboxylate (sulfo-SMCC) [see e.g. Karpovsky et al. (1984) *J. Exp. Med.* 160:1686; Liu, M A et al. (1985) *Proc. Natl. Acad. Sci. USA* 82:8648]. Other methods include those described in Paulus (1985) *Behring Ins. Mitt. No.* 78, 118-132; Brennan et al. (1985) *Science* 229:81-83, and Glennie et al. (1987) *J. Immunol.* 139: 2367-2375. Preferred conjugating agents are SATA and sulfo-SMCC, both available from Pierce Chemical Co. (Rockford, Ill.)].

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260, 203; 5,455,030; 4,881,175; 5,132,405; 5,091,513; 5,476, 786; 5,013,653; 5,258,498; and 5,482,858, all of which are expressly incorporated herein by reference.

The antibodies of the invention may be Bi-specific T-cell engagers (BiTEs). BiTEs are a class of artificial bispecific monoclonal antibodies. They direct a host's immune system, more specifically the T cells' cytotoxic activity, against cancer cells. BiTEs are generally fusion proteins consisting of two single-chain variable fragments (scFvs) of different antibodies, or amino acid sequences from four different genes, on a single peptide chain, preferably of about 55 kilodaltons. Preferably, one of the scFvs binds to T cells via the CD3 receptor, and the other to a tumour cell via a tumour-specific molecule.

Binding of the bispecific molecules to their specific targets can be confirmed by, for example, enzyme-linked immunosorbent assay (ELISA), radioimmunoassay (RIA), FACS analysis, bioassay (e.g. growth inhibition), or Western Blot assay. Each of these assays generally detects the presence of protein-antibody complexes of particular interest by employing a labeled reagent (e.g. an antibody) specific for the complex of interest. For example, the FcR-antibody complexes can be detected using e.g. an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Glycosylation

Another type of covalent modification is alterations in glycosylation. In some embodiments, the antibodies disclosed herein can be modified to include one or more engineered glycoforms. By "engineered glycoform" as used herein is meant a carbohydrate composition that is covalently attached to the antibody, wherein the carbohydrate composition differs chemically from that of a parent antibody. Engineered glycoforms may be useful for a variety of purposes, including but not limited to enhancing or reducing effector function. For example, an aglycoslated antibody can be made (i.e. the antibody that lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al., and can be accomplished by removing the asparagine at position 297.

A preferred form of engineered glycoform is afucosylation, which has been shown to be correlated to an increase in ADCC function, presumably through tighter binding to the FcγRIIIa receptor. In this context, "afucosylation" means that the majority of the antibody produced in the host cells is substantially devoid of fucose, e.g. 90-95-98% of the generated antibodies do not have appreciable fucose as a component of the carbohydrate moiety of the antibody (generally attached at N297 in the Fc region). Defined functionally, afucosylated antibodies generally exhibit at least a 50% or higher affinity to the FcγRIIIa receptor.

Engineered glycoforms may be generated by a variety of methods known in the art (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1, all entirely incorporated by reference; (POTELLIGENT® technology [Biowa, Inc., Princeton, N.J.]; GlycoMAb® glycosylation engineering technology [Glycart Biotechnology AG, Zurich, Switzerland]). Many of these techniques are based on controlling the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells, by regulating enzymes involved in the glycosylation pathway (for example FUT8 [α1,6-fucosyltransferase] and/or β1-4-N-acetylglucosaminyltransferase III [GnTIII]), or by modifying carbohydrate(s) after the IgG has been expressed. For example, the "sugar engineered antibody" or "SEA technology" of Seattle Genetics functions by adding modified saccharides that inhibit fucosylation during production; see for example US2009/0317869, hereby incorporated by reference in its entirety. "Engineered glycoform" typically refers to the different carbohydrate or oligosaccharide as compared to the antibody made in the absence of the glycosylation technology; thus an antibody can include an engineered glycoform.

Alternatively, engineered glycoform may refer to the IgG variant that comprises the different carbohydrate or oligosaccharide. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antibody is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 and in Aplin and Wriston, 1981, CRC Crit. Rev. Biochem., pp. 259-306, both entirely incorporated by reference.

Removal of carbohydrate moieties present on the starting antibody (e.g. post-translationally) may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131, both entirely incorporated by reference. Enzymatic cleavage of carbohydrate moieties on polypeptides can be achieved by the use of a variety of endo- and exo-glycosidases as described by Thotakura et al., 1987, Meth. Enzymol. 138:350, entirely incorporated by reference, including removal of fucose residues using a fucosidase enzyme as is known in the art. Glycosylation at potential glycosylation sites may be prevented by the use of the compound tunicamycin as described by Duskin et al., 1982, J. Biol. Chem. 257:3105, entirely incorporated by reference. Tunicamycin blocks the formation of protein-N-glycoside linkages.

Another type of covalent modification of the antibody comprises linking the antibody to various non-proteinaceous polymers, including, but not limited to, various polyols such as polyethylene glycol, polypropylene glycol or polyoxyalkylenes, in the manner set forth in, for example, 2005-2006 PEG Catalog from Nektar Therapeutics (available at the Nektar website) U.S. Pat. Nos. 4,640,835; 4,496,689; 4,301,144; 4,670,417; 4,791,192 or 4,179,337, all entirely incorporated by reference. In addition, as is known in the art, amino acid substitutions may be made in various positions within the antibody to facilitate the addition of polymers such as PEG. See for example, U.S. Publication No. 2005/0114037A1, entirely incorporated by reference.

In additional embodiments, for example in the use of the antibodies of the invention for diagnostic or detection purposes, the antibodies may comprise a label. By "labeled" herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent dyes; although labels include enzymes and particles such as magnetic particles as well. Preferred labels include, but are not limited to, fluorescent lanthanide complexes (including those of Europium and Terbium), and fluorescent labels including, but not limited to, quantum dots, fluorescein, rhodamine, tetramethylrhodamine, eosin, erythrosin, coumarin, methyl-coumarins, pyrene, Malacite green, stilbene, Lucifer Yellow, Cascade Blue, Texas Red, the Alexa dyes, the Cy dyes, and others described in the 6th Edition of the Molecular Probes Handbook by Richard P. Haugland, hereby expressly incorporated by reference.

Antibody-Drug Conjugates

In some embodiments, the anti-LY75 antibodies of the invention are conjugated with drugs to form antibody-drug conjugates (ADCs). In general, ADCs are used in oncology applications, where the use of antibody-drug conjugates for the local delivery of cytotoxic or cytostatic agents allows for the targeted delivery of the drug moiety to tumors, which can allow higher efficacy, lower toxicity, etc. An overview of this technology is provided in Ducry et al., Bioconjugate Chem., 21:5-13 (2010), Carter et al., Cancer J. 14(3):154 (2008) and Senter, Current Opin. Chem. Biol. 13:235-244 (2009), all of which are hereby incorporated by reference in their entirety.

Thus the invention provides anti-LY75 antibodies conjugated to drugs. Generally, conjugation is done by covalent attachment to the antibody, as further described below, and generally relies on a linker, often a peptide linkage (which, as described below, may be designed to be sensitive to cleavage by proteases at the target site or not). In addition, as described above, linkage of the linker-drug unit (LU-D) can be done by attachment to cysteines within the antibody. As will be appreciated by those in the art, the number of drug moieties per antibody can change, depending on the conditions of the reaction, and can vary from 1:1 to 10:1 drug: antibody. As will be appreciated by those in the art, the actual number is an average.

Thus the invention provides anti-LY75 antibodies conjugated to drugs. As described below, the drug of the ADC can be any number of agents, including but not limited to cytotoxic agents such as chemotherapeutic agents, growth inhibitory agents, toxins (for example, an enzymatically active toxin of bacterial, fungal, plant, or animal origin, or fragments thereof), or a radioactive isotope (that is, a radioconjugate) are provided. In other embodiments, the invention further provides methods of using the ADCs.

Drugs for use in the present invention include cytotoxic drugs, particularly those which are used for cancer therapy. Such drugs include, in general, DNA damaging agents, anti-metabolites, natural products and their analogs. Exemplary classes of cytotoxic agents include the enzyme inhibitors such as dihydrofolate reductase inhibitors, and thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, dolastatins, maytansinoids, differentiation inducers, and taxols.

Members of these classes include, for example, taxol, methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, caminomycin, aminopterin, tallysomycin, podophyllotoxin and podophyllotoxin derivatives such as etoposide or etoposide phosphate, vinblastine, vincristine, vindesine, taxanes including taxol, taxotere retinoic acid, butyric acid, N8-acetyl spermidine, camptothecin, calicheamicin, esperamicin, ene-diynes, duocarmycin A, duocarmycin SA, calicheamicin, camptothecin, hemiasterlins, maytansinoids (including DM1), monomethylauristatin E (MMAE), monomethylauristatin F (MMAF), and maytansinoids (DM4) and their analogues.

Toxins may be used as antibody-toxin conjugates and include bacterial toxins such as diphtheria toxin, plant toxins such as ricin, small molecule toxins such as geldanamycin (Mandler et al (2000) J. Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342), hemiasterlins (WO2004/026293; Zask et al., (2004) J. Med. Chem, 47: 4774-4786). Toxins may exert their cytotoxic and cytostatic effects by mechanisms including tubulin binding, DNA binding, or topoisomerase inhibition.

Conjugates of an anti-LY75 antibody and one or more small molecule toxins, such as a maytansinoids, dolastatins, auristatins, a trichothecene, calicheamicin, and CC1065, and the derivatives of these toxins that have toxin activity, may also be used.

Maytansinoids

Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. As described below, drugs may be modified by the incorporation of a functionally active group such as a thiol or amine group for conjugation to the antibody.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides) and those having modifications at other positions.

Exemplary maytansinoid drug moieties also include those having modifications such as: C-9-SH (U.S. Pat. No. 4,424,219) (prepared by the reaction of maytansinol with H2S or P2S5); C-14-alkoxymethyl(demethoxy/CH$_2$OR) (U.S. Pat. No. 4,331,598); C-14-hydroxymethyl or acyloxymethyl (CH$_2$OH or CH$_2$OAc) (U.S. Pat. No. 4,450,254) (prepared from *Nocardia*); C-15-hydroxy/acyloxy (U.S. Pat. No. 4,364,866) (prepared by the conversion of maytansinol by

*Streptomyces*); C-15-methoxy (U.S. Pat. Nos. 4,313,946 and 4,315,929) (isolated from *Trewia nudlflora*); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol).

Of particular use are DM1 (disclosed in U.S. Pat. No. 5,208,020, incorporated by reference) and DM4 (disclosed in U.S. Pat. No. 7,276,497, incorporated by reference). See also a number of additional maytansinoid derivatives and methods in U.S. Pat. No. 5,416,064, WO/01/24763, U.S. Pat. Nos. 7,303,749, 7,601,354, U.S. Ser. No. 12/631,508, WO02/098883, U.S. Pat. Nos. 6,441,163, 7,368,565, WO02/16368 and WO04/1033272, all of which are expressly incorporated by reference in their entirety.

ADCs containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference. Liu et al., Proc. Natl. Acad. Sci. USA 93:8618-8623 (1996) described ADCs comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Chari et al., Cancer Research 52:127-131 (1992) describe ADCs in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses 3×105 HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Auristatins and Dolastatins

In some embodiments, the ADC comprises an anti-LY75 antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Senter et al, Proceedings of the American Association for Cancer Research, Volume 45, Abstract Number 623, presented Mar. 28, 2004 and described in United States Patent Publication No. 2005/0238648, the disclosure of which is expressly incorporated by reference in its entirety.

An exemplary auristatin embodiment is MMAE (shown in FIG. 10 wherein the wavy line indicates the covalent attachment to a linker (L) of an antibody drug conjugate; see U.S. Pat. No. 6,884,869 expressly incorporated by reference in its entirety).

Another exemplary auristatin embodiment is MMAF, shown in FIG. 10 wherein the wavy line indicates the covalent attachment to a linker (L) of an antibody drug conjugate (US 2005/0238649, U.S. Pat. Nos. 5,767,237 and 6,124,431, expressly incorporated by reference in their entirety):

Additional exemplary embodiments comprising MMAE or MMAF and various linker components (described further herein) have the following structures and abbreviations (wherein Ab means antibody and p is 1 to about 8):

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lubke, The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat Biotechnol 21(7):778-784.

Calicheamicin

In other embodiments, the ADC comprises an antibody of the invention conjugated to one or more calicheamicin molecules. For example, Mylotarg is the first commercial ADC drug and utilizes calicheamicin γ1 as the payload (see U.S. Pat. No. 4,970,198, incorporated by reference in its entirety). Additional calicheamicin derivatives are described in U.S. Pat. Nos. 5,264,586, 5,384,412, 5,550,246, 5,739,116, 5,773,001, 5,767,285 and 5,877,296, all expressly incorporated by reference. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, γ1I, α2I, α2I, N-acetyl-γ1I, PSAG and θI1 (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Duocarmycins

CC-1065 (see U.S. Pat. No. 4,169,888, incorporated by reference) and duocarmycins are members of a family of antitumor antibiotics utilized in ADCs. These antibiotics appear to work through sequence-selectively alkylating DNA at the N3 of adenine in the minor groove, which initiates a cascade of events that result in apoptosis.

Important members of the duocarmycins include duocarmycin A (U.S. Pat. No. 4,923,990, incorporated by reference) and duocarmycin SA (U.S. Pat. No. 5,101,038, incorporated by reference), and a large number of analogues as described in U.S. Pat. Nos. 7,517,903, 7,691,962, 5,101,038; 5,641,780; 5,187,186; 5,070,092; 5,070,092; 5,641,780; 5,101,038; 5,084,468, 5,475,092, 5,585,499, 5,846,545, WO2007/089149, WO2009/017394A1, U.S. Pat. Nos.

5,703,080, 6,989,452, 7,087,600, 7,129,261, 7,498,302, and 7,507,420, all of which are expressly incorporated by reference.

Pyrrolobenzodiazepines

Pyrrolobenzodiazepine (PBD) (Journal of Medicinal Chemistry 2001, 44, 737-748) are DNA-interactive agents with significant cytotoxicity. Thirteen structures of this family have been isolated, including compounds such as anthramycin, mazethramycin, porothramycin, prothracarcin, sibanomycin, tomaymycin, sibiromycin, chicamycin A, neothramycin A, B, and DC-81 (Medicinal Chemistry and Drug Design, ISBN: 978-953-51-0513-8, Ahmed Kamal et al. DOI: 10.5772/38869). Other analogues of this family have been prepared and have been conjugated to antibodies as described in Patent Nos. WO2011/130598 and WO2011/130616, which are expressly incorporated by reference.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an ADC formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radio-conjugated antibodies. Examples include At211, I131, I125, Y90, Re186, Re188, Sm153, Bi212, P32, Pb212 and radioactive isotopes of Lu.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as Tc99m or I123, Re186, Re188 and In111 can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate Iodine-123. "Monoclonal Antibodies in Immunoscintigraphy" (Chatal, CRC Press 1989) describes other methods in detail.

For compositions comprising a plurality of antibodies, the drug loading is represented by p, the average number of drug molecules per Antibody. Drug loading may range from 1 to 20 drugs (D) per Antibody. The average number of drugs per antibody in preparation of conjugation reactions may be characterized by conventional means such as mass spectroscopy, ELISA assay, and HPLC. The quantitative distribution of Antibody-Drug-Conjugates in terms of p may also be determined.

In some instances, separation, purification, and characterization of homogeneous Antibody-Drug-conjugates where p is a certain value from Antibody-Drug-Conjugates with other drug loadings may be achieved by means such as reverse phase HPLC or electrophoresis. In exemplary embodiments, p is 2, 3, 4, 5, 6, 7, or 8 or a fraction thereof.

The generation of Antibody-drug conjugate compounds can be accomplished by any technique known to the skilled artisan. Briefly, the Antibody-drug conjugate compounds can include an anti-LY75 antibody as the Antibody unit, a drug, and optionally a linker that joins the drug and the binding agent.

A number of different reactions are available for covalent attachment of drugs and/or linkers to binding agents. This is can be accomplished by reaction of the amino acid residues of the binding agent, for example, antibody molecule, including the amine groups of lysine, the free carboxylic acid groups of glutamic and aspartic acid, the sulfhydryl groups of cysteine and the various moieties of the aromatic amino acids. A commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule.

Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents. Other techniques are known to the skilled artisan and within the scope of the present invention.

In some embodiments, an intermediate, which is the precursor of the linker, is reacted with the drug under appropriate conditions. In other embodiments, reactive groups are used on the drug and/or the intermediate. The product of the reaction between the drug and the intermediate, or the derivatized drug, is subsequently reacted with an anti-LY75 antibody of the invention under appropriate conditions.

It will be understood that chemical modifications may also be made to the desired compound in order to make reactions of that compound more convenient for purposes of preparing conjugates of the invention. For example a functional group e.g. amine, hydroxyl, or sulfhydryl, may be appended to the drug at a position which has minimal or an acceptable effect on the activity or other properties of the drug.

Linker Units

Typically, the antibody-drug conjugate compounds comprise a Linker unit between the drug unit and the antibody unit. In some embodiments, the linker is cleavable under intracellular or extracellular conditions, such that cleavage of the linker releases the drug unit from the antibody in the appropriate environment. For example, solid tumors that secrete certain proteases may serve as the target of the cleavable linker; in other embodiments, it is the intracellular proteases that are utilized. In yet other embodiments, the linker unit is not cleavable and the drug is released, for example, by antibody degradation in lysosomes.

In some embodiments, the linker is cleavable by a cleaving agent that is present in the intracellular environment (for example, within a lysosome or endosome or caveolea). The linker can be, for example, a peptidyl linker that is cleaved by an intracellular peptidase or protease enzyme, including, but not limited to, a lysosomal or endosomal protease. In some embodiments, the peptidyl linker is at least two amino acids long or at least three amino acids long or more.

Cleaving agents can include, without limitation, cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Peptidyl linkers that are cleavable by enzymes that are present in LY75-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker (SEQ ID NO: X)). Other examples of such linkers are described, e.g., in U.S. Pat. No. 6,214,345, incorporated herein by reference in its entirety and for all purposes.

In some embodiments, the peptidyl linker cleavable by an intracellular protease is a Val-Cit linker or a Phe-Lys linker (see, e.g., U.S. Pat. No. 6,214,345, which describes the synthesis of doxorubicin with the val-cit linker).

In other embodiments, the cleavable linker is pH-sensitive, that is, sensitive to hydrolysis at certain pH values. Typically, the pH-sensitive linker hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) may be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (for example, a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935).

In other embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker unit is not cleavable and the drug is released by antibody degradation. (See U.S. Publication No. 2005/0238649 incorporated by reference herein in its entirety and for all purposes).

In many embodiments, the linker is self-immolative. As used herein, the term "self-immolative Spacer" refers to a bifunctional chemical moiety that is capable of covalently linking together two spaced chemical moieties into a stable tripartite molecule. It will spontaneously separate from the second chemical moiety if its bond to the first moiety is cleaved. See for example, WO 2007/059404A2, WO06/110476A2, WO05/112919A2, WO2010/062171, WO09/017394, WO07/089149, WO 07/018431, WO04/043493 and WO02/083180, which are directed to drug-cleavable substrate conjugates where the drug and cleavable substrate are optionally linked through a self-immolative linker and which are all expressly incorporated by reference.

Often the linker is not substantially sensitive to the extracellular environment. As used herein, not substantially sensitive to the extracellular environment," in the context of a linker, means that no more than about 20%, 15%, 10%, 5%, 3%, or no more than about 1% of the linkers, in a sample of antibody-drug conjugate compound, are cleaved when the antibody-drug conjugate compound presents in an extracellular environment (for example, in plasma).

Whether a linker is not substantially sensitive to the extracellular environment can be determined, for example, by incubating with plasma the antibody-drug conjugate compound for a predetermined time period (for example, 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent (that is, in the milieu of the linker-therapeutic agent moiety of the antibody-drug conjugate compound as described herein). In yet other embodiments, the linker promotes cellular internalization when conjugated to both the auristatin compound and the anti-LY75 antibodies of the invention.

A variety of exemplary linkers that can be used with the present compositions and methods are described in WO 2004/010957, U.S. Publication No. 2006/0074008, U.S. Publication No. 20050238649, and U.S. Publication No. 2006/0024317 (each of which is incorporated by reference herein in its entirety and for all purposes).

Drug Loading

Drug loading is represented by p and is the average number of Drug moieties per antibody in a molecule. Drug loading ("p") may be 1, 2, 3, 4, 5, 6, 7, 8, 9, 10, 11, 12, 13, 14, 15, 16, 17, 18, 19, 20 or more moieties (D) per antibody, although frequently the average number is a fraction or a decimal. Generally, drug loading of from 1 to 4 is frequently useful, and from 1 to 2 is also useful. ADCs of the invention include collections of antibodies conjugated with a range of drug moieties, from 1 to 20, for example, 1-15, 1-10, 2-9, 3-8, 4-7, 5-6. The average number of drug moieties per antibody in preparations of ADC from conjugation reactions may be characterized by conventional means such as mass spectroscopy and, ELISA assay.

The quantitative distribution of ADC in terms of p may also be determined. In some instances, separation, purification, and characterization of homogeneous ADC where p is a certain value from ADC with other drug loadings may be achieved by means such as electrophoresis.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the invention ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antibody may be less than 8, and may be about 2 to about 5. See US 2005/0238649 A1 (herein incorporated by reference in its entirety).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments (such as thioMab or thioFab prepared as disclosed herein and in WO2006/034488 (herein incorporated by reference in its entirety)).

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography.

In some embodiments, a homogeneous ADC with a single loading value may be isolated from the conjugation mixture by electrophoresis or chromatography.

Methods of Determining Cytotoxic Effect of ADCs

Methods of determining whether a Drug or Antibody-Drug conjugate exerts a cytostatic and/or cytotoxic effect on a cell are known. Generally, the cytotoxic or cytostatic activity of an Antibody Drug conjugate can be measured by: exposing mammalian cells expressing a target protein of the Antibody Drug conjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the Antibody Drug conjugate.

For determining whether an Antibody Drug conjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of $^3$H-thymidine during the final 8 hours of the 72-hour period. The incorporation of $^3$H-thymidine into cells of the culture is measured in the presence and absence of the Antibody Drug conjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an Antibody Drug conjugate is useful in the treatment of cancers.

Cell viability can be measured by determining in a cell the uptake of a dye such as neutral red, trypan blue, or ALA-MAR™ blue (see, e.g., Page et al., 1993, Intl. J. Oncology 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytotoxicity (Skehan et al., 1990, J. Natl. Cancer Inst. 82:1107-12).

Alternatively, a tetrazolium salt, such as MTT, is used in a quantitative colorimetric assay for mammalian cell survival and proliferation by detecting living, but not dead, cells (see, e.g., Mosmann, 1983, J. Immunol. Methods 65:55-63).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., 1995, Cancer Research 55:3110-16).

In vivo, the effect of a therapeutic composition of the anti-LY75 antibody of the invention can be evaluated in a suitable animal model. For example, xenogenic cancer models can be used, wherein cancer explants or passaged xenograft tissues are introduced into immune compromised animals, such as nude or SCID mice (Klein et al, 1997, Nature Medicine 3: 402-408). Efficacy can be measured using assays that measure inhibition of tumor formation, tumor regression or metastasis, and the like.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

Methods for Producing the Antibodies of the Invention

The present invention further provides methods for producing the disclosed anti-LY75 antibodies. These methods encompass culturing a host cell containing isolated nucleic acid(s) encoding the antibodies of the invention. As will be appreciated by those in the art, this can be done in a variety of ways, depending on the nature of the antibody. In some embodiments, in the case where the antibodies of the invention are full length traditional antibodies, for example, a heavy chain variable region and a light chain variable region under conditions such that an antibody is produced and can be isolated.

The variable heavy and light chains of LY75_A1 are disclosed herein (both protein and nucleic acid sequences); as will be appreciated in the art, these can be easily augmented to produce full length heavy and light chains. That is, having provided the DNA fragments encoding $V_H$ and $V_K$ segments as outlined herein, these DNA fragments can be further manipulated by standard recombinant DNA techniques, for example, to convert the variable region genes to full-length antibody chain genes, to Fab fragment genes, or to a scFv gene. In these manipulations, a $V_K$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_H1$, $C_H2$ and $C_H3$). The sequences of murine heavy chain constant region genes are known in the art [see e.g. Kabat, E. A., et al. (1991) Sequences of Proteins of Immunological Interest, Fifth Edition, US Department of Health and Human Services, NIH Publication No. 91-3242] and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_H1$ constant region.

The isolated DNA encoding the VL/VK region can be converted to a full-length light chain gene (as well as a Fab light chain gene) by operatively linking the $V_L$-encoding DNA to another DNA molecule encoding the light chain constant region, $C_L$. The sequences of murine light chain constant region genes are known in the art [see, e.g. Kabat, E. A., et al. (1991) Sequences of Proteins of Immunological Interest, Fifth Edition, US Department of Health and Human Services, NIH Publication No. 91-3242] and DNA fragments encompassing these regions can be obtained by standard PCR amplification. In preferred embodiments, the light chain constant region can be a kappa or lambda constant region.

To create a scFv gene, the $V_H$- and $V_L/V_K$-encoding DNA fragments are operatively linked to another fragment encoding a flexible linker, e.g. encoding the amino acid sequence $(Gly_4\text{-}Ser)_3$, such that the $V_H$ and $V_L/V_K$ sequences can be expressed as a contiguous single-chain protein, with the $V_L/V_K$ and $V_H$ regions joined by the flexible linker [see e.g. Bird et al. (1988) Science 242:423-426; Huston et al. (1988) Proc. Natl. Acad. Sci. USA 85:5879-5883; McCafferty et al., (1990) Nature 348:552-554].

In general, nucleic acids are provided which encode the antibodies of the invention. Such polynucleotides encode for both the variable and constant regions of each of the heavy and light chains, although other combinations are also contemplated by the present invention in accordance with the compositions described herein. The present invention also contemplates oligonucleotide fragments derived from the disclosed polynucleotides and nucleic acid sequences complementary to these polynucleotides.

The polynucleotides can be in the form of RNA or DNA. Polynucleotides in the form of DNA, cDNA, genomic DNA, nucleic acid analogs, and synthetic DNA are within the scope of the present invention. The DNA may be double-stranded or single-stranded, and if single stranded, may be the coding (sense) strand or non-coding (anti-sense) strand. The coding sequence that encodes the polypeptide may be identical to the coding sequence provided herein or may be a different coding sequence, which sequence, as a result of the redundancy or degeneracy of the genetic code, encodes the same polypeptides as the DNA provided herein.

In some embodiments, nucleic acid(s) encoding the antibodies of the invention are incorporated into expression vectors, which can be extrachromosomal or designed to integrate into the genome of the host cell into which it is introduced. Expression vectors can contain any number of appropriate regulatory sequences (including, but not limited to, transcriptional and translational control sequences, promoters, ribosomal binding sites, enhancers, origins of replication, etc.) or other components (selection genes, etc.), all of which are operably linked as is well known in the art. In some cases two nucleic acids are used and each put into a different expression vector (e.g. heavy chain in a first expression vector, light chain in a second expression vector), or alternatively they can be put in the same expression vector. It will be appreciated by those skilled in the art that the design of the expression vector(s), including the selection of regulatory sequences may depend on such factors as the choice of the host cell, the level of expression of protein desired, etc.

In general, the nucleic acids and/or expression can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g. in the presence of an inducer, in a suitable non-human animal, in suitable culture media supplemented with appropriate salts, growth factors, antibiotics, nutritional supplements, etc.), whereby the encoded polypeptide(s) are produced. In some cases, the heavy chains are produced in one cell and the light chain in another.

Mammalian cell lines available as hosts for expression are known in the art and include many immortalized cell lines available from the American Type Culture Collection (ATCC), Manassas, Va. including but not limited to Chinese hamster ovary (CHO) cells, HEK 293 cells, NSO cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. In some embodiments, the antibodies can be produced in transgenic animals such as cows or chickens.

General methods for antibody molecular biology, expression, purification, and screening are well known, for example, see U.S. Pat. Nos. 4,816,567, 4,816,397, 6,331,415 and 7,923,221, as well as Antibody Engineering, edited by Kontermann & Dubel, Springer, Heidelberg, 2001 and 2010 Hayhurst & Georgiou, 2001, Curr Opin Chem Biol 5:683-689; Maynard & Georgiou, 2000, Annu Rev Biomed Eng 2:339-76; and Morrison, S. (1985) Science 229:1202.

Pharmaceutical Compositions

In another aspect, the present invention provides a composition, e.g. a pharmaceutical composition, containing one or a combination of LY75 antibodies, or antigen-binding portion(s) thereof, of the present invention, formulated together with a pharmaceutically acceptable carrier. Such compositions may include one or a combination of (e.g. two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e. combined with other agents. For example, the combination therapy can include an anti-antibody of the present invention combined with at least one other anti-tumor agent, or an anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion). Depending on the route of administration, the active compound, i.e. antibody, immunoconjugate, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects [see, e.g. Berge, S. M., et al. (1977) *J. Pharm. Sci.* 66:1-19]. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of 100 percent, this amount will range from about 0.01 percent to about 99 percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g. a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, for example, 0.001 to 50 mg/kg, 0.005 to 20 mg/kg, 0.01 to 10 mg/kg and more usually 0.01 to 5 mg/kg, of the host body weight. For example dosages can be 0.05 mg/kg body weight, 0.1 mg/kg body weight, 0.3 mg/kg body weight, 0.3 mg/kg body weight, 0.5 mg/kg body weight, 1 mg/kg body weight, 2 mg/kg body weight, 3 mg/kg body weight, 4 mg/kg body weight, 5 mg/kg body weight 6 mg/kg body weight, 7 mg/kg body weight, 8 mg/kg body weight, 9 mg/kg body weight, 10 mg/kg body weight, 12 mg/kg body weight, 15 mg/kg body weight, 20 mg/kg body weight, 25 mg/kg body weight, 30 mg/kg body weight, or within the range of 0.1-20 mg/kg, 0.5-15 mg/kg, 1-10 mg/kg, 2-8 mg/kg, 3-7 mg/kg, 4-6 mg/kg. An exemplary treatment regime entails administration once per day, once every 2 days, once per week, once every two weeks, once every three weeks, once every four weeks, once a month, once every 6 weeks, once every 3 months or once every three to 6 months. Preferred dosage regimens for an anti-LY75 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, daily, twice weekly, weekly, monthly, every three months, every six months, or yearly. Intervals can also be irregular as indicated by measuring blood levels of antibody to the target antigen in the patient. In some methods, dosage is adjusted to achieve a plasma antibody concentration of about 1-1000 µg/ml, 5-750 µg/ml, 10-600 µg/ml, 15-500 µg/ml, 20-400 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-LY75 antibody of the invention preferably results in a decrease in severity of disease symptoms, an increase in frequency and duration of disease symptom-free periods, or a prevention of impairment or disability due to the disease affliction. For example, for the treatment of the LY75 mediated tumors, a "therapeutically effective dosage" preferably inhibits cell growth or tumor growth by at least about 20%, at least about 30%, more preferably by at least about 40%, at least about 50% even more preferably by at least about 60%, at least about 70% and still more preferably by at least about 80% or at least about 90%, relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art [see, e.g. *Sustained and Controlled Release Drug Delivery Systems* (1978) J. R. Robinson, ed., Marcel Dekker, Inc., N.Y].

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g. U.S. Pat. Nos. 4,522,811; 5,374,548; and 5,399,331. The liposomes may comprise one or more moieties which are selectively transported into specific cells or organs, thus enhance targeted drug delivery [see, e.g. V. V. Ranade (1989) *J. Clin. Pharmacol.* 29:685]. Exemplary targeting moieties include folate or biotin (see, e.g. U.S. Pat. No. 5,416,016.); mannosides [Umezawa et al. (1988) *Biochem. Biophys. Res. Commun.* 153:1038]; antibodies [P. G. Bloeman et al. (1995) *FEBS Lett.* 357:140; M. Owais et al. (1995) *Antimicrob. Agents Chemother.* 39:180]; surfactant protein A receptor [Briscoe et al. (1995) *Am. J. Physiol* 1233:134]; p 120 [Schreier et al. (1994) *J. Biol. Chem.* 269:9090]; see also K. Keinanen; M. L. Laukkanen (1994) *FEBS Lett.* 346:123; J. J. Killion; I. J. Fidler (1994) *Immunomethods* 4:273.

Uses and Methods

The antibodies, antibody compositions and methods of the present invention have numerous in vitro and in vivo diagnostic and therapeutic utilities involving the diagnosis and treatment of LY75 mediated disorders.

In some embodiments, these molecules can be administered to cells in culture, in vitro or ex vivo, or to human subjects, e.g. in vivo, to treat, prevent and to diagnose a variety of disorders. As used herein, the term "subject" is intended to include human and non-human animals. Non-human animals include all vertebrates, e.g. mammals and non-mammals, such as non-human primates, sheep, dogs, cats, cows, horses, chickens, amphibians, and reptiles. Preferred subjects include human patients having disorders mediated by LY75 activity. The methods are particularly suitable for treating human patients having a disorder associated with the aberrant LY75 expression. When antibodies to LY75 are administered together with another agent, the two can be administered in either order or simultaneously.

Given the specific binding of the antibodies of the invention for LY75, the antibodies of the invention can be used to specifically detect LY75 expression on the surface of cells and, moreover, can be used to purify LY75 via immunoaffinity purification.

Furthermore, given the expression of LY75 on tumor cells, the antibodies, antibody compositions and methods of the present invention can be used to treat a subject with a tumorigenic disorder, e.g. a disorder characterized by the presence of tumor cells expressing LY75 or in the manufacture of a medicament for the treatment of such a disorder including, for example gastric cancer, kidney cancer, thyroid cancer, oesophageal cancer, head and neck cancer, skin cancer, liver cancer, pancreatic cancer, colorectal cancer, bladder cancer, prostate cancer, breast cancer including triple negative breast cancer, ovarian cancer, lung cancer, myeloma, leukaemia, including chronic lymphocytic leukaemia and acute myeloid leukaemia, non-Hodgkin's lymphoma, including DLBCL, B-Cell Lymphoma, Follicular Lymphoma, Mantle Cell Lymphoma, Lymphoma of Mucosa-Associated Lymphoid Tissue (MALT), T-Cell/Histiocyte-Rich B-Cell Lymphoma, Burkitt's Lymphoma, Lymphoplasmacytic Lymphoma, Small Lymphocytic Lymphoma, Marginal Zone Lymphoma, T Cell Lymphoma, Peripheral T-Cell Lymphoma, Anaplastic Large Cell Lymphoma and Angiolmmunoblastic T-Cell Lymphoma. LY75 has been demonstrated to be internalised on antibody binding as illustrated in Examples 5 and 7 below, thus enabling the antibodies of the invention to be used in any payload mechanism of action e.g. an ADC approach, radioimmunoconjugate, or ADEPT approach.

In one embodiment, the antibodies (e.g. monoclonal antibodies, antibody fragments, Nanobody®, multispecific and bispecific molecules and compositions, etc.) of the invention can be used to detect levels of LY75, or levels of cells which contain LY75 on their membrane surface, which levels can then be linked to certain disease symptoms. Alternatively, the antibodies, generally administered as ADCs, can be used to inhibit or block LY75 function which, in turn, can be linked to the prevention or amelioration of certain disease symptoms, thereby implicating the LY75 as a mediator of the disease. This can be achieved by contacting a sample and a control sample with the anti-LY75 antibody under conditions that allow for the formation of a complex between the antibody and LY75. Any complexes formed between the antibody and the LY75 are detected and compared in the sample and the control.

In another embodiment, the antibodies (e.g. monoclonal antibodies, multispecific and bispecific molecules and compositions) of the invention can be initially tested for binding activity associated with therapeutic or diagnostic use in vitro. For example, compositions of the invention can be tested using the flow cytometric assays described in the Examples below.

The antibodies (e.g. monoclonal antibodies, multispecific and bispecific molecules, immunoconjugates and compositions) of the invention have additional utility in therapy and diagnosis of LY75 related diseases. For example, the monoclonal antibodies, the multispecific or bispecific molecules and the immunoconjugates can be used to elicit in vivo or in vitro one or more of the following biological activities: to inhibit the growth of and/or kill a cell expressing LY75; to mediate phagocytosis or ADCC of a cell expressing LY75 in the presence of human effector cells, or to block LY75 ligand binding to LY75.

In a particular embodiment, the antibodies (e.g. monoclonal antibodies, multispecific and bispecific molecules and compositions) are used in vivo to treat, prevent or diagnose a variety of LY75-related diseases. Examples of LY75-related diseases include, among others, human cancer tissues representing gastric cancer, colorectal cancer, prostate cancer, breast cancer, ovarian cancer kidney cancer, thyroid cancer, oesophageal cancer, head and neck cancer, skin cancer, liver cancer, pancreatic cancer, bladder cancer, myeloma, leukaemia, including chronic lymphocytic leukaemia, acute myeloid leukaemia, non-Hodgkin's lymphoma, including DLBCL, B-Cell Lymphoma, Follicular Lymphoma, Mantle Cell Lymphoma, Lymphoma of Mucosa-Associated Lymphoid Tissue (MALT), T-Cell/Histiocyte-Rich B-Cell Lymphoma, Burkitt's Lymphoma, Lymphoplasmacytic Lymphoma, Small Lymphocytic Lymphoma, Marginal Zone Lymphoma, T Cell Lymphoma, Peripheral T-Cell Lymphoma, Anaplastic Large Cell Lymphoma and AngioImmunoblastic T-Cell Lymphoma and lung cancer.

Suitable routes of administering the antibody compositions (e.g. monoclonal antibodies, multispecific and bispecific molecules and immunoconjugates) of the invention in vivo and in vitro are well known in the art and can be selected by those of ordinary skill. For example, the antibody compositions can be administered by injection (e.g. intravenous or subcutaneous). Suitable dosages of the molecules used will depend on the age and weight of the subject and the concentration and/or formulation of the antibody composition.

As previously described, the anti-LY75 antibodies of the invention can be co-administered with one or other more therapeutic agents, e.g. a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g. an anti-cancer therapy, e.g. radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/kg dose once every four weeks and adriamycin is intravenously administered as a 60-75 mg/ml dose once every 21 days. Other agents suitable for co-administration with the antibodies of the invention include other agents used for the treatment of cancers, e.g. gastric cancer, colorectal cancer, prostate cancer, breast cancer, ovarian cancer or lung cancer, such as Avastin®, 5FU and gemcitabine. Co-administration of the anti-LY75 antibodies or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Target-specific effector cells, e.g. effector cells linked to compositions (e.g. monoclonal antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$, but will vary depending on the therapeutic purpose. In general, the amount will be sufficient to obtain localization at the target cell, e.g. a tumor cell expressing LY75, and to affect cell killing by, e.g. phagocytosis. Routes of administration can also vary.

Therapy with target-specific effector cells can be performed in conjunction with other techniques for removal of targeted cells. For example, anti-tumor therapy using the compositions (e.g. monoclonal antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-LY75 antibodies linked to anti-Fc-gamma RI or anti-CD3 may be used in conjunction with IgG- or IgA-receptor specific binding agents.

Bispecific and multispecific molecules of the invention can also be used to modulate FcγR or FcγR levels on effector cells, such as by capping and elimination of receptors on the cell surface. Mixtures of anti-Fc receptors can also be used for this purpose.

The compositions (e.g. monoclonal antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g. monoclonal antibodies, multispecific and bispecific molecules) of the invention can also be lysed by complement. In yet another embodiment, the compositions of the invention do not activate complement.

The compositions (e.g. monoclonal antibodies, multispecific and bispecific molecules and immunoconjugates) of the invention can also be administered together with complement. In certain embodiments, the instant disclosure provides compositions comprising antibodies, multispecific or bispecific molecules and serum or complement. These compositions can be advantageous when the complement is located in close proximity to the antibodies, multispecific or bispecific molecules. Alternatively, the antibodies, multispecific or bispecific molecules of the invention and the complement or serum can be administered separately.

Also within the scope of the present invention are kits comprising the antibody compositions of the invention (e.g. monoclonal antibodies, bispecific or multispecific molecules, or immunoconjugates) and instructions for use. The kit can further contain one or more additional reagents, such as an immunosuppressive reagent, a cytotoxic agent or a radiotoxic agent, or one or more additional antibodies of the invention (e.g. an antibody having a complementary activity which binds to an epitope in the LY75 antigen distinct from the first antibody).

Accordingly, patients treated with antibody compositions of the invention can be additionally administered (prior to, simultaneously with, or following administration of an antibody of the invention) with another therapeutic agent, such as a cytotoxic or radiotoxic agent, which enhances or augments the therapeutic effect of the antibodies.

In other embodiments, the subject can be additionally treated with an agent that modulates, e.g. enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

The compositions (e.g. antibodies, multispecific and bispecific molecules) of the invention can also be used to target cells expressing FcγR or LY75, for example, for labeling such cells. For such use, the binding agent can be linked to a molecule that can be detected. Thus, the invention provides methods for localizing ex vivo or in vitro cells expressing Fc receptors, such as FcγR, or LY75. The detectable label can be, e.g. a radioisotope, a fluorescent compound, an enzyme, or an enzyme co-factor.

In a particular embodiment, the invention provides methods for detecting the presence of the LY75 antigen in a sample, or measuring the amount of the LY75 antigen, comprising contacting the sample, and a control sample, with a monoclonal antibody, or an antigen binding portion thereof, which specifically binds to LY75, under conditions that allow for formation of a complex between the antibody or portion thereof and LY75. The formation of a complex is then detected, wherein a difference complex formation between the sample compared to the control sample is indicative the presence of the LY75 antigen in the sample.

In other embodiments, the invention provides methods for treating a LY75 mediated disorder in a subject, e.g. human cancers, including gastric cancer, kidney cancer, thyroid cancer, oesophageal cancer, head and neck cancer, skin cancer, liver cancer, pancreatic cancer, colorectal cancer, bladder cancer, prostate cancer, breast cancer including triple negative breast cancer, ovarian cancer, lung cancer, myeloma, leukaemia, including chronic lymphocytic leukaemia and acute myeloid leukaemia, and non-Hodgkin's lymphoma, including DLBCL, B-Cell Lymphoma, Follicular Lymphoma, Mantle Cell Lymphoma, Lymphoma of Mucosa-Associated Lymphoid Tissue (MALT), T-Cell/Histiocyte-Rich B-Cell Lymphoma, Burkitt's Lymphoma, Lymphoplasmacytic Lymphoma, Small Lymphocytic Lymphoma, Marginal Zone Lymphoma, T Cell Lymphoma, Peripheral T-Cell Lymphoma, Anaplastic Large Cell Lymphoma and Angiolmmunoblastic T-Cell Lymphoma.

In all embodiments of the invention, preferred cancers include non-Hodgkin's lymphoma, acute myeloid leukaemia, chronic lymphocytic leukaemia and triple-negative breast cancer bladder cancer and pancreatic cancer.

All references cited in this specification, including without limitation all papers, publications, patents, patent applications, presentations, texts, reports, manuscripts, brochures, books, internet postings, journal articles, periodicals, product fact sheets, and the like, one hereby incorporated by reference into this specification in their entireties. The discussion of the references herein is intended to merely summarize the assertions made by their authors and no admission is made that any reference constitutes prior art and Applicants' reserve the right to challenge the accuracy and pertinence of the cited references.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the dependent claims.

The present invention is further illustrated by the following examples which should not be construed as further limiting.

Example 1: Generation of Human Monoclonal Antibodies Against LY75-Antigen

Following standard procedures, mice (xenomouse IgG1) were immunized with CHO cells transfected with full length LY75.

The specificity of antibodies raised against the LY75 was tested by flow cytometry on HEK293 cells transfected with LY75 and subsequently on LY75-expressing HT29 cells. To test the ability of the antibodies to bind to the cell surface LY75 protein, the antibodies were incubated with the LY75-expressing cells. Cells were washed in FACS buffer (DPBS, 2% FBS), centrifuged and resuspended in 100 μl of the diluted primary LY75 antibody (also diluted in FACS buffer) . The antibody-cell line complex was incubated on ice for 60 min and then washed twice with FACS buffer as described above. The cell-antibody pellet was resuspended in 100 μl of the diluted secondary antibody (also diluted in FACS buffer) and incubated on ice for 60 min on ice. The pellet was washed as before and resuspended in 200 μl FACS buffer. The samples were loaded onto the BD FACScanto II flow cytometer and the data analyzed using the BD FACSdiva software (results not shown).

Example 2: Structural Characterization of Monoclonal Antibodies to LY75

The cDNA sequences encoding the heavy and light chain variable regions of the LY75_A1 monoclonal antibody were obtained using standard PCR techniques and were sequenced using standard DNA sequencing techniques.

The antibody sequences may be mutagenized to revert back to germline residues at one or more residues.

The nucleotide and amino acid sequences of the heavy chain variable region of LY75_A1 are shown in SEQ ID NO: 3 and 1, respectively.

The nucleotide and amino acid sequences of the light chain variable region of LY75_A1 are shown in SEQ ID NO: 4 and 2, respectively.

Comparison of the LY75_A1 heavy chain immunoglobulin sequence to the known human germline immunoglobulin heavy chain sequences demonstrated that the LY75_A1 heavy chain utilizes a $V_H$ segment from human germline $V_H$ 3-15 and a $J_H$ segment from human germline $J_H$JH4. Further analysis of the LY75_A1 $V_H$ sequence using the Kabat system of CDR region determination led to the delineation of the heavy chain CDR1, CDR2 and CDR3 regions as shown in SEQ ID NOs: 5, 6 and 7, respectively. The alignments of the LY75_A1 CDR1, CDR2 and CDR3 $V_H$ sequences to the germline $V_H$ 3-15 and germline $J_H$JH4 sequence are shown in FIG. 1.

Comparison of the LY75_A1 light chain immunoglobulin sequence to the known human germline immunoglobulin light chain sequences demonstrated that the LY75_A1 light chain utilizes a $V_K$ segment from human germline $V_K$ O12 and a $J_K$ segment from human germline $J_K$JK4. Further analysis of the LY75_A1 $V_K$ sequence using the Kabat system of CDR region determination led to the delineation of the light chain CDR1, CDR2 and CDR3 regions as shown in SEQ ID NOs:8, 9 and 10, respectively. The alignments of the LY75_A1 CDR1, CDR2 and CDR3 $V_K$ sequences to the germline $V_K$ O12 and germline $J_K$JK4 sequences are shown in FIG. 2.

Example 3: Immunohistochemistry Using Monoclonal Antibody to LY75

Using the human monoclonal antibodies specific to LY75, immunohistochemistry was performed on FFPE HT-29 and A549 cell pellets, FFPE non-Hodgkin's lymphoma and pancreatic cancer arrays, and fresh frozen lymphoma/leukaemia tumours, ovarian cancer, pancreatic cancer, and breast cancer sections and a normal tissue array.

Materials and Methods
Materials
Xylenes (X5P-1gal) from Fisher Scientific, PA, USA.
Histoprep 100% ethanol (HC-800-1GAL) from Fisher Scientific, PA, USA.
10× Citrate buffer for heat induced epitope retrieval (AP9003125) from Thermo Scientific, MA, USA.
Thermo Scientific* Pierce* Peroxidase Suppressor (35000) from Thermo Scientific, MA, USA.
Serum free protein block (X0909) from Dako, Calif., USA
Secondary antibody: goat anti-human IgG Fab-FITC conjugated (109-097-003) from Jackson Immunoresearch, PA, USA
Chrome pure Human IgG, whole molecule (09-000-003) from Jackson Immunoresearch, PA, USA
Tertiary antibody: mouse anti-FITC (ab10257) from Abcam, Mass., USA
Purified human IgG isotype control (1-001A) from R&D Systems, Minn., USA
Tween-20 (BP337-100) from Fisher Scientific, PA, USA
Acetone (BP2403-4) from Fisher Scientific, PA, USA
Dual Link EnVision+ HRP-conjugated polymer, Mouse and Rabbit (K4063) from Dako, Calif., USA.
DAB 2-solution kit (882014) from Invitrogen, N.Y., USA.
Harris Hematoxylin (23-245-677) from Fisher Scientific, PA, USA.
Faramount mounting media (S302580) from Dako, Calif., USA.
Tissue sections and arrays were purchased from US Biomax Inc., MD, USA or Origene, Md., USA.

Preparation of FFPE Slides: Deparaffinisation and Rehydration

FFPE slides were deparaffinised in xylene (2×3 minutes) then rehydrated through 1:1 xylene: 100% ethanol (1×3 minutes), 100% ethanol (2×3 minutes), 95% ethanol (1×3 minutes), 70% ethanol (1×3 minutes), 50% ethanol (1×3 minutes), and tap water (1×3 minutes). Preparation of FFPE slides: Antigen Retrieval (Microwave).

The LY75 antigen was retrieved using microwave heat, high power until boiling then low power for 10 minutes in 50 mL 1× citrate buffer in a Coplin jar. Slides were then left to cool to room temperature for a further 15 min, then washed in tap water, 3 minutes. Circles were drawn around each tissue section/TMA with a hydrophobic barrier pen and slides were then washed 3 times in PBS, 3 minutes each wash.

Preparation of FF slides

Slides were removed from storage at −80 C and allowed to dry at room temperature in the fume hood for 20-30 minutes. The slides were fixed for 10 min in ice cold acetone at −20 C, then allowed to dry for 20 min in the fume hood at room temperature. Slides were washed and rehydrated in PBS, 3 washes for 3 min each. Sections were outlined with a hydrophobic barrier pen.

Preparation of Antibody Complexes

The primary anti-LY75 antibody was diluted in serum free protein block (SFPB) to obtain a solution with a concentration 20-fold greater than the final desired concentration (20 µg/mL for 1 µg/mL final). The secondary antibody, goat anti-human immunoglobulin G (IgG) antigen-binding fragment (Fab), was prepared similarly in SFPB to create a solution of equal concentration.

Equal volumes of primary and secondary antibodies were combined in a labelled tube, gently mixed, and incubated for 3 minutes at room temperature, resulting in a primary antibody concentration 10-fold greater than the desired final concentration (10 µg/mL for 1 µg/mL final). This mixture was diluted 1:5 with SFPB, gently mixed, and incubated for 30 minutes at room temperature, resulting in a primary antibody concentration twice that of the desired final concentration (2 µg/mL for 1 µg/mL final).

To produce the final staining complexes, a 1% (10 µg/µL) solution of human IgG was prepared in SFPB and equal volume added to the primary/secondary antibody mixture. This combination was gently mixed and incubated at room temperature for 30 minutes, diluting by half the primary antibody concentration of the primary/secondary antibody mixture and resulting in the desired final primary antibody concentration (1 µg/mL).

Immunostaining

Meanwhile, endogenous tissue peroxidase activity was blocked by incubating tissues with peroxidase suppressor for 5-10 minutes at RT in a humidified chamber. Slides were then washed in PBS 3×3 minutes each wash. Tissues were incubated in SFPB for 30 minutes at room temperature in a humidified chamber. Final staining complexes were applied to each tissue section and/or microarray, and the slides were incubated for 30 min at room temperature in a humidified chamber. Slides were then washed once in PBS and once in PBST (PBS+0.125% Tween-20), 3 minutes each wash. The tertiary antibody mouse anti-FITC, was applied at 2 μg/mL concentration for 30 min, room temperature, in a humidified chamber. Sections were then washed once in PBS and once in PBST, 3 min each wash. Dual Link EnVision+ anti-mouse/rabbit-HRP-conjugated polymer was then applied to the tissues and the slides were incubated for 30 min at room temperature in a humidified chamber. Slides were then washed once in PBS, once in PBST, 3 minutes each wash. Tissues were incubated in DAB solution prepared according to the manufacturer's instructions at room temperature for 10 min. Slides were then washed once in running tap water for 2 minutes and once in PBS for 3 minutes. The slides were counterstained with Hematoxylin for 30 seconds at room temperature, and washed with running tap water. The slides were dried at room temperature for 30 minutes and coverslips were then mounted onto the slides using Faramount mounting media.

Results

LY75_A1 showed positivity in FFPE Triple Negative breast cancer samples, where 77% of the sections showed positive staining and 55% exhibited robust (+++) staining.

Staining for LY75 in FF normal tissues was generally absent to low. Ductal epithelium of the breast, salivary gland, and pancreas exhibited marked low to moderate staining, and the spleen stained low positive. Therefore antibodies directed to LY75 may have utility as therapeutics and diagnostics in some of the tested cancers and possibly other cancer types showing expression of LY75.

Example 4: Efficacy of DM1-Conjugated Anti-LY75 Monoclonal Antibodies in HT-29 Cells Materials
Cell stripper (Non-enzymatic cell dissociation) (MT-25-056CI) from Fisher Scientific, PA, USA.
PBS pH 7.4 (1×) (SH30028LS) from Fisher Scientific, PA, USA.
RPMI 1640 Media (MT-10-041-CM) from Fisher Scientific, PA, USA.
Cell Titer Glo (G7572) from Promega, Wis., USA.
Method
Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

The results depicted in FIG. 3a show a subpopulation of antibodies, know to bind to LY75, which can induce cell kill of HT-29 cells. This suggests while antibodies can bind to LY75 only a few display efficacy when conjugated to DM1. Antibodies where then chosen from the subpopulation for further cytotoxic activity analysis.

Example 5: Efficacy of DM1-Conjugated and DM4-Conjugated Anti-LY75 Monoclonal Antibodies in Colorectal Cancer Cells Materials
Cell stripper (Non-enzymatic cell dissociation) (MT-25-056CI) from Fisher Scientific, PA, USA.
PBS pH 7.4 (1×) (SH30028LS) from Fisher Scientific, PA, USA.
RPMI 1640 Media (MT-10-041-CM) from Fisher Scientific, PA, USA.
Cell Titer Glo (G7572) from Promega, Wis., USA.
Method
Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

Figure 3B:
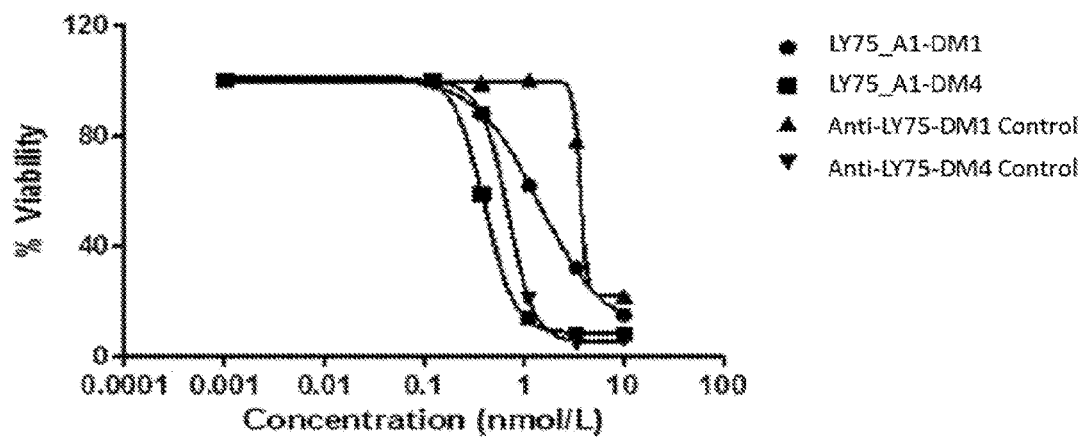
FIG. 3b depicts cytotoxic activity of anti-LY75 antibodies conjugated to either DM1 or DM4 in HT-29.

FIG. 3b shows the cytotoxic activity of anti-LY75 antibodies conjugated to DM1 and DM4 towards HT-29 cells These results demonstrate an increase in cytotoxic activity proportional to antibody concentration and other anti-LY75 antibodies conjugated to a toxin (selected from Example 1).

Example 6: Efficacy of DM1-Conjugated and DM4-Conjugated Anti-LY75 Monoclonal Antibodies in Lymphoma Cell Lines Materials
Cell stripper (Non-enzymatic cell dissociation) (MT-25-056CI) from Fisher Scientific, PA, USA.
PBS pH 7.4 (1×) (SH30028LS) from Fisher Scientific, PA, USA.
RPMI 1640 Media (MT-10-041-CM) from Fisher Scientific, PA, USA.
Cell Titer Glo (G7572) from Promega, Wis., USA.
Method
Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

Figure 3C:
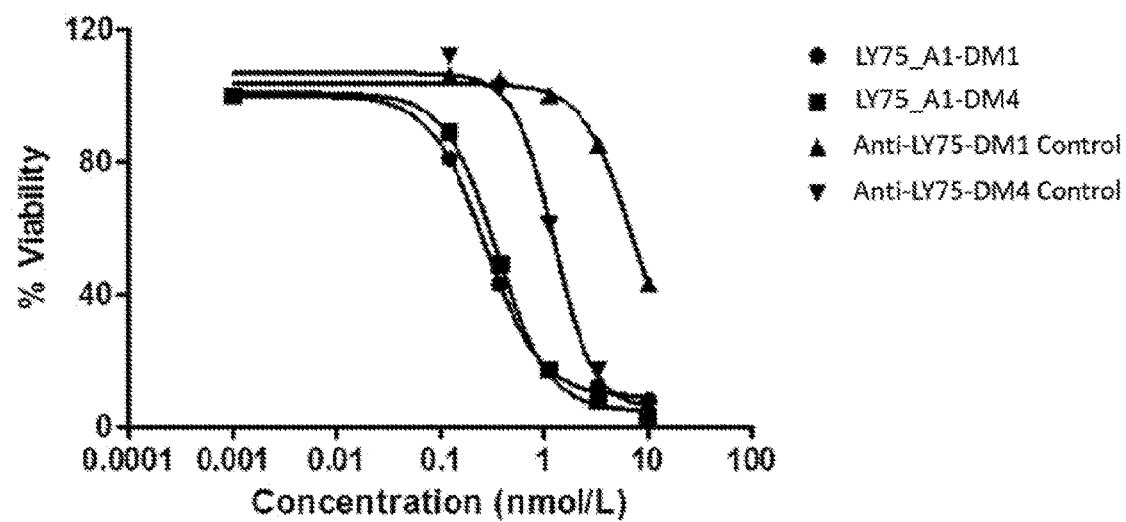
FIG. 3c depicts cytotoxic activity of anti-LY75 antibodies conjugated to either DM1 or DM4 in RAJI cells.
Figure 3D:
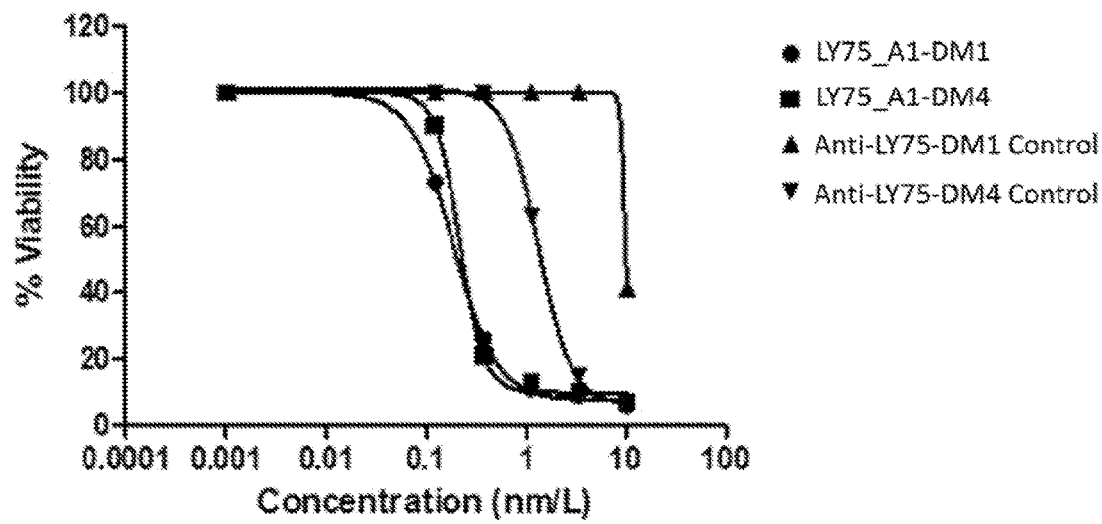
FIG. 3d depicts cytotoxic activity of anti-LY75 antibodies conjugated to either DM1 or DM4 in Namalwa cells.
Figure 3E:
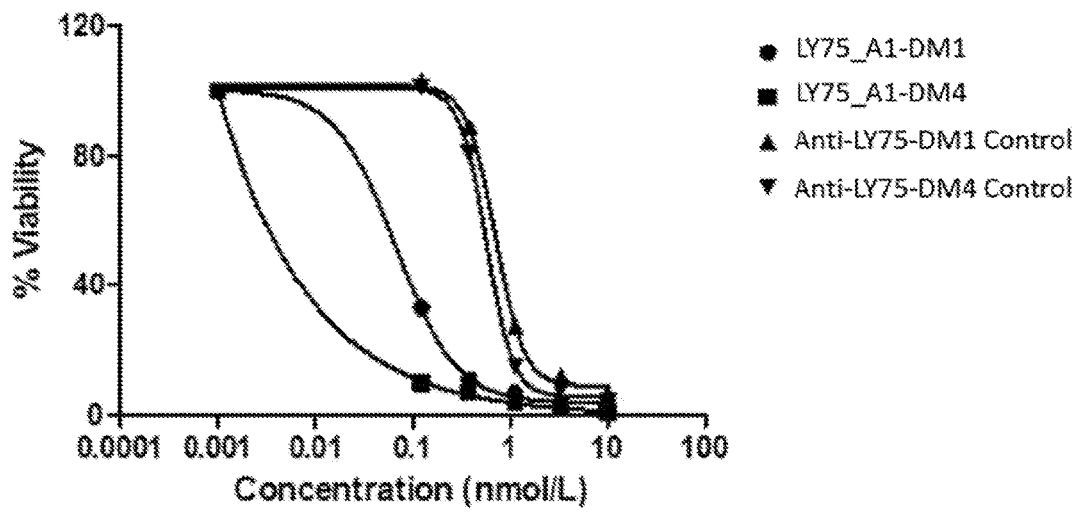
FIG. 3e depicts cytotoxic activity of anti-LY75 antibodies conjugated to either DM1 or DM4 in Karpas 299 cells.

FIG. 3c shows the cytotoxic activity of anti-LY75 antibodies conjugated to DM1 and DM4 towards RAJI cells. FIG. 3d shows the cytotoxic activity of anti-LY75 antibodies conjugated to DM1 and DM4 towards Namalwa cells. FIG. 3e shows the cytotoxic activity of anti-LY75 antibodies conjugated to DM1 and DM4 towards Karpas 299 cells. These results demonstrates an increase in cytotoxic activity proportional to antibody concentration and other anti-LY75 antibodies conjugated to DM1 and DM4 (selected from Example 1).

Example 7: Efficacy of DM1-Conjugated and DM4-Conjugated Anti-LY75 Monoclonal Antibodies in Pancreatic Cancer Cell Lines Materials
Cell stripper (Non-enzymatic cell dissociation) (MT-25-056CI) from Fisher Scientific, PA, USA.
PBS pH 7.4 (1×) (SH30028LS) from Fisher Scientific, PA, USA.
RPMI 1640 Media (MT-10-041-CM) from Fisher Scientific, PA, USA.
Cell Titer Glo (G7572) from Promega, Wis., USA.
Method
Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

Figure 3F:
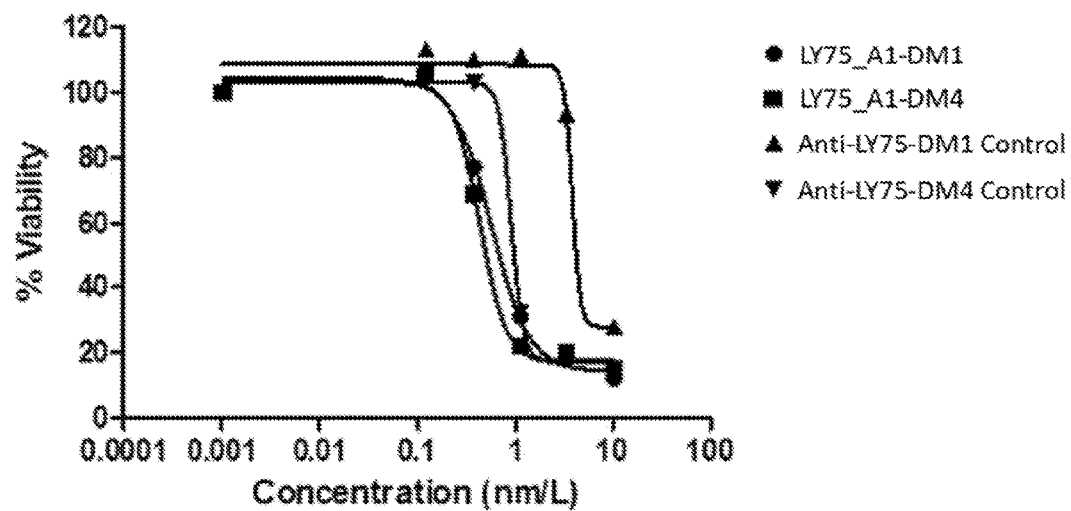
FIG. 3f depicts cytotoxic activity of anti-LY75 antibodies conjugated to either DM1 or DM4 in BxPC3 cells.
Figure 3G:
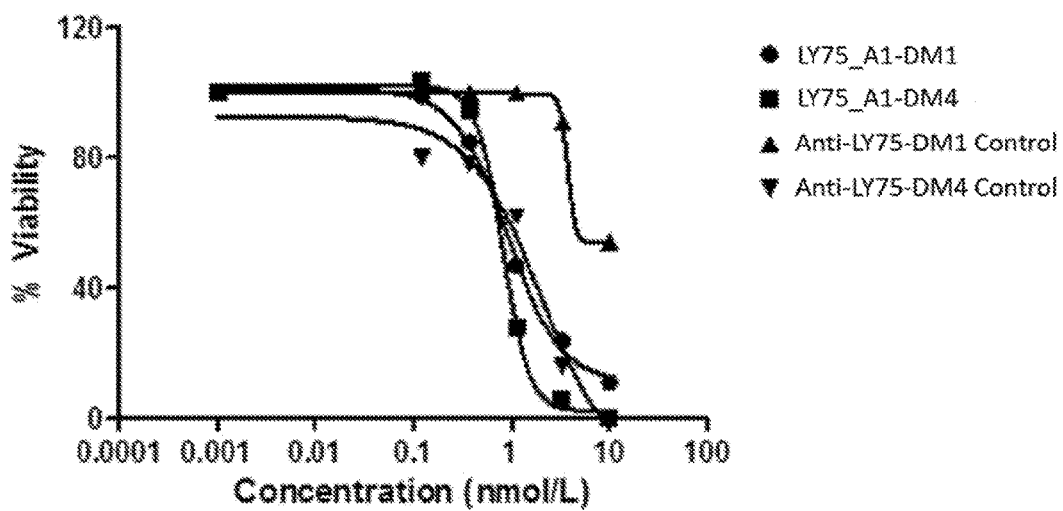
FIG. 3g depicts cytotoxic activity of anti-LY75 antibodies conjugated to either DM1 or DM4 in HupT4 cells.
Figure 3H:
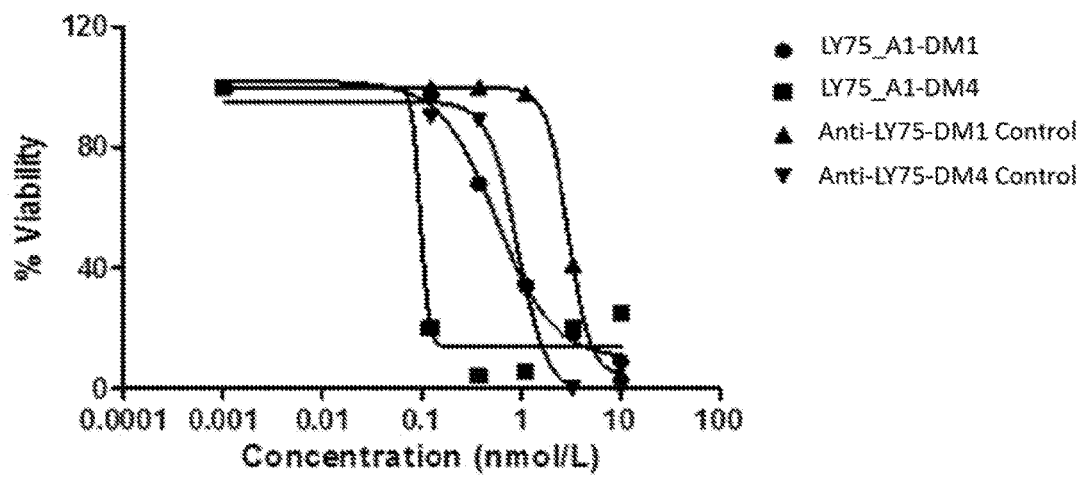
FIG. 3h depicts cytotoxic activity of anti-LY75 antibodies conjugated to either DM1 or DM4 in HPAFFII cells.

FIG. 3f shows the cytotoxic activity of anti-LY75 antibodies conjugated to DM1 and DM4 towards BxPC3 cells. FIG. 3g shows the cytotoxic activity of anti-LY75 antibodies conjugated to DM1 and DM4 towards HupT4 cells. FIG. 3h shows the cytotoxic activity of anti-LY75 antibodies conjugated to DM1 and DM4 towards HPAFFII cells. These results demonstrates an increase in cytotoxic activity proportional to antibody concentration and other anti-LY75 antibodies conjugated to DM1 and DM4 (selected from Example 1).

Example 8: Efficacy of DM1-Conjugated and DM4-Conjugated Anti-LY75 Monoclonal Antibodies in Chronic Lymphocytic Leukaemia Cell Lines Materials
Cell stripper (Non-enzymatic cell dissociation) (MT-25-056CI) from Fisher Scientific, PA, USA.
PBS pH 7.4 (1×) (SH30028LS) from Fisher Scientific, PA, USA.
RPMI 1640 Media (MT-10-041-CM) from Fisher Scientific, PA, USA.
Cell Titer Glo (G7572) from Promega, Wis., USA.
Method
Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

Figure 3I:
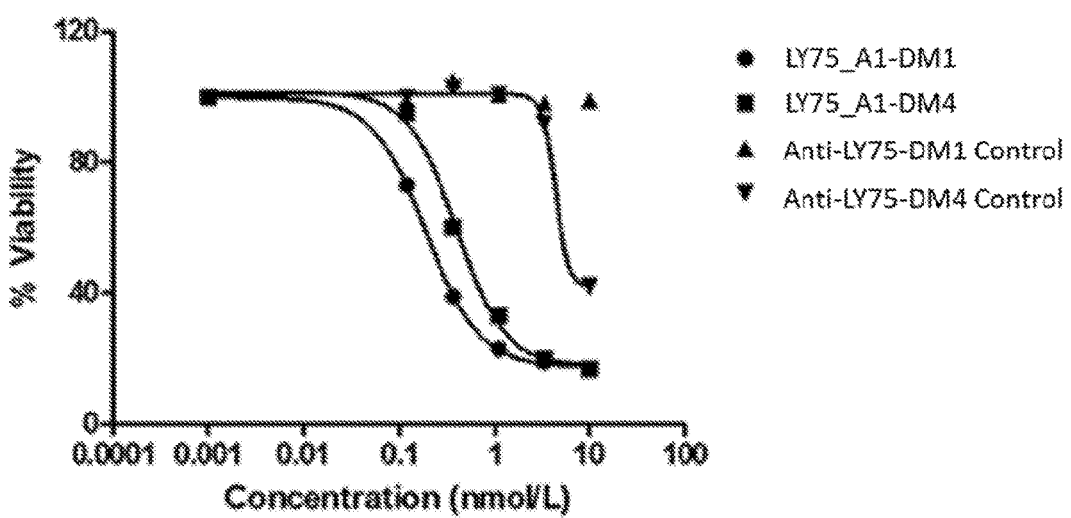
FIG. 3i depicts cytotoxic activity of anti-LY75 antibodies conjugated to either DM1 or DM4 in EHEB cells.
Figure 3J:
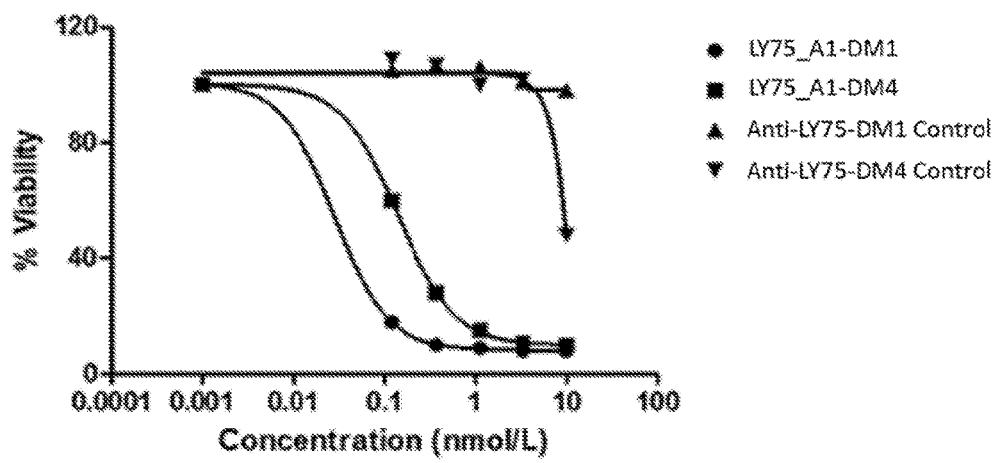
FIG. 3j depicts cytotoxic activity of anti-LY75 antibodies conjugated to either DM1 or DM4 in Mec-1 cells.
Figure 3K:
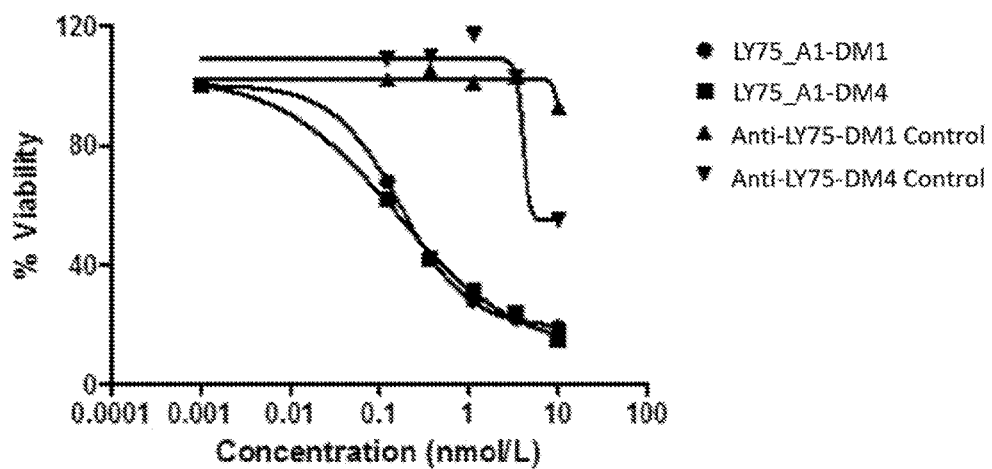
FIG. 3k depicts cytotoxic activity of anti-LY75 antibodies conjugated to either DM1 or DM4 in AML-193 cells.
Figure 3L:
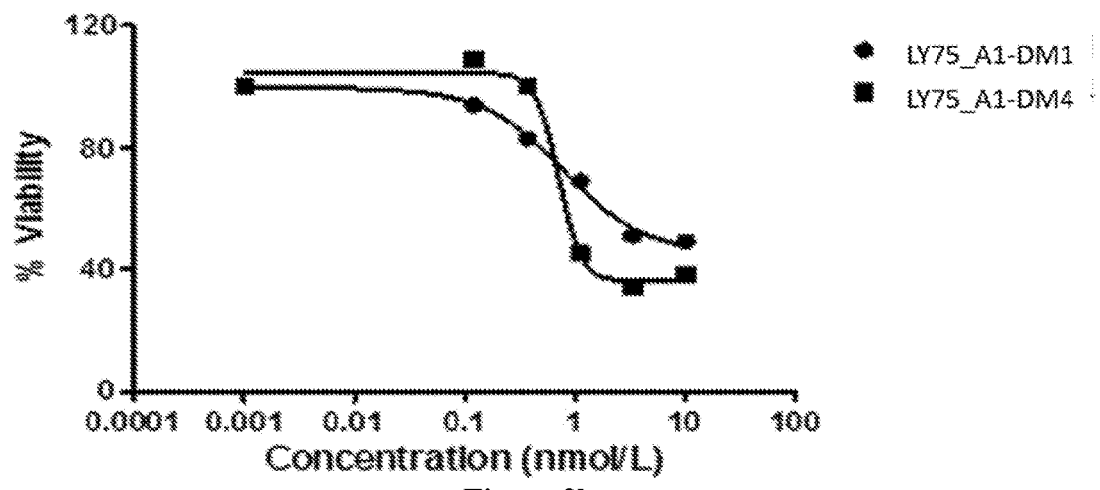
FIG. 3l depicts cytotoxic activity of anti-LY75 antibodies conjugated to either DM1 or DM4 in HCC 70 cells.
Figure 3M:
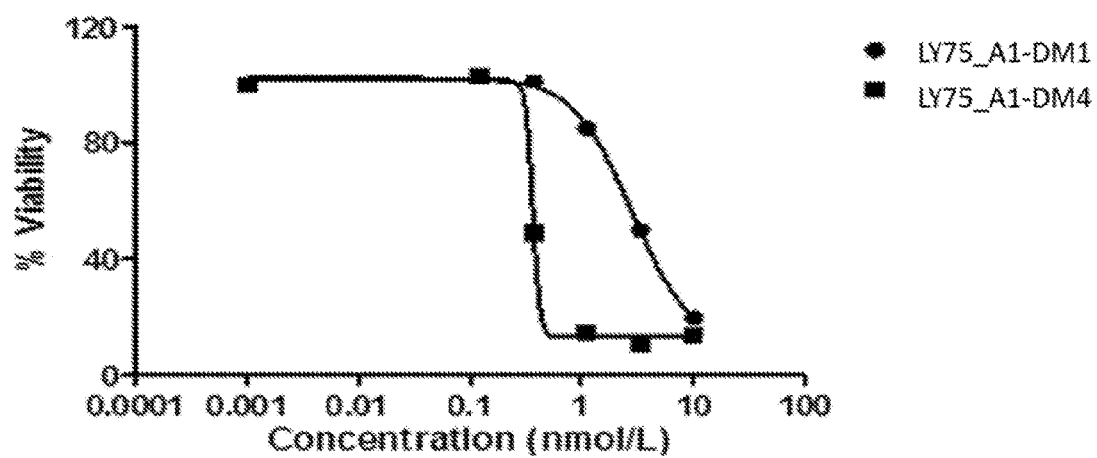
FIG. 3m depicts cytotoxic activity of anti-LY75 antibodies conjugated to either DM1 or DM4 in HCC 1806 cells.
Figure 3N:
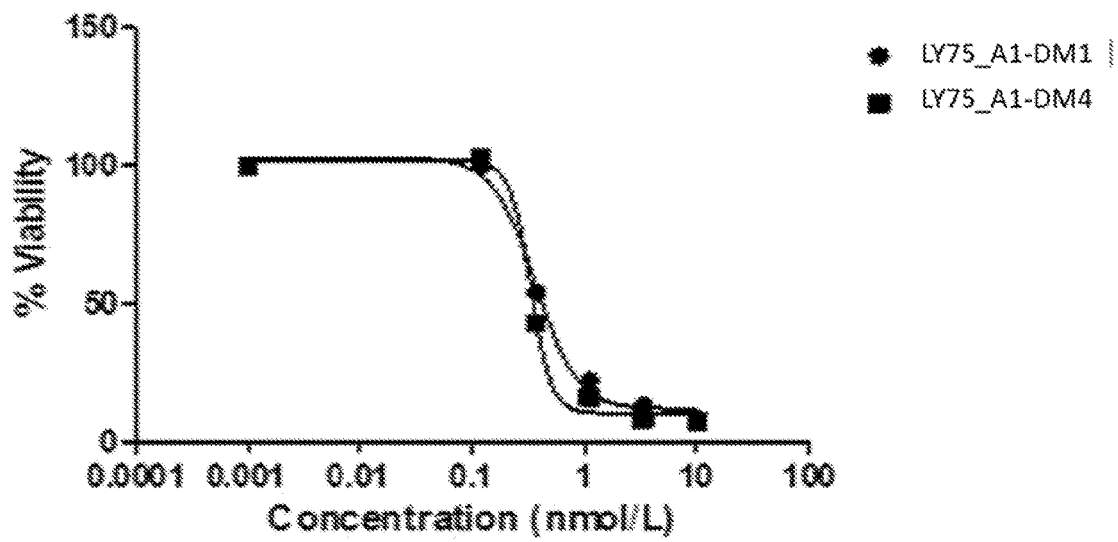
FIG. 3n depicts cytotoxic activity of anti-LY75 antibodies conjugated to either DM1 or DM4 in MDA-MB-468 cells.

FIG. 3i shows the cytotoxic activity of anti-LY75 antibodies conjugated to DM1 and DM4 towards EHEB cells. FIG. 3j shows the cytotoxic activity of anti-LY75 antibodies conjugated to DM1 and DM4 towards Mec-1 cells. These results demonstrates an increase in cytotoxic activity proportional to antibody concentration and other anti-LY75 antibodies conjugated to DM1 and DM4 (selected from Example 1).

Example 9: Efficacy of DM1-Conjugated and DM4-Conjugated Anti-LY75 Monoclonal Antibodies in Acute Monocytic Leukaemia Cell Lines Materials
Cell stripper (Non-enzymatic cell dissociation) (MT-25-056CI) from Fisher Scientific, PA, USA.
PBS pH 7.4 (1×) (SH30028LS) from Fisher Scientific, PA, USA.
RPMI 1640 Media (MT-10-041-CM) from Fisher Scientific, PA, USA.
Cell Titer Glo (G7572) from Promega, Wis., USA.
Method
Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.
50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.
The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.
Results
FIG. 3$k$ shows the cytotoxic activity of anti-LY75 antibodies conjugated to DM1 and DM4 towards AML-193 cells. These results demonstrates an increase in cytotoxic activity proportional to antibody concentration and other anti-LY75 antibodies conjugated to DM1 and DM4 (selected from Example 1).

Example 10: Efficacy of DM1-Conjugated and DM4-Conjugated Anti-LY75 Monoclonal Antibodies in Breast Cancer Cell Lines Materials
Cell stripper (Non-enzymatic cell dissociation) (MT-25-056CI) from Fisher Scientific, PA, USA.
PBS pH 7.4 (1×) (SH30028LS) from Fisher Scientific, PA, USA.
RPMI 1640 Media (MT-10-041-CM) from Fisher Scientific, PA, USA.
Cell Titer Glo (G7572) from Promega, Wis., USA.
Method
Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.
50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.
The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.
Results
FIG. 3$l$ shows the cytotoxic activity of anti-LY75 antibodies conjugated to DM1 and DM4 towards HCC 70 (ER negative, PR negative and Her2 negative) cells. FIG. 3$m$ shows the cytotoxic activity of anti-LY75 antibodies conjugated to DM1 and DM4 towards HCC 1806 (ER negative, PR negative and Her2 negative) cells. FIG. 3$n$ shows the cytotoxic activity of anti-LY75 antibodies conjugated to DM1 and DM4 towards MDA-MB-468 cells. These results demonstrates an increase in cytotoxic activity proportional to antibody concentration.

Example 11: Efficacy of DM1-Conjugated and DM4-Conjugated Anti-LY75 Monoclonal Antibodies in Bladder Cancer Cell Lines Materials
Cell stripper (Non-enzymatic cell dissociation) (MT-25-056CI) from Fisher Scientific, PA, USA.
PBS pH 7.4 (1×) (SH30028LS) from Fisher Scientific, PA, USA.
RPMI 1640 Media (MT-10-041-CM) from Fisher Scientific, PA, USA.
Cell Titer Glo (G7572) from Promega, Wis., USA.
Method
Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.
50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.
The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

Figure 3O:
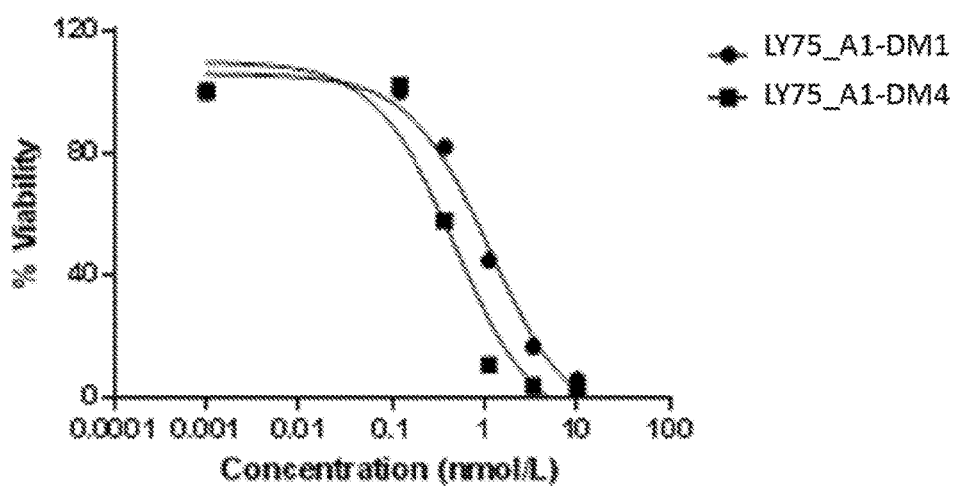
FIG. 3o depicts cytotoxic activity of anti-LY75 antibodies conjugated to either DM1 or DM4 in RT4 cells.
Figure 3P:
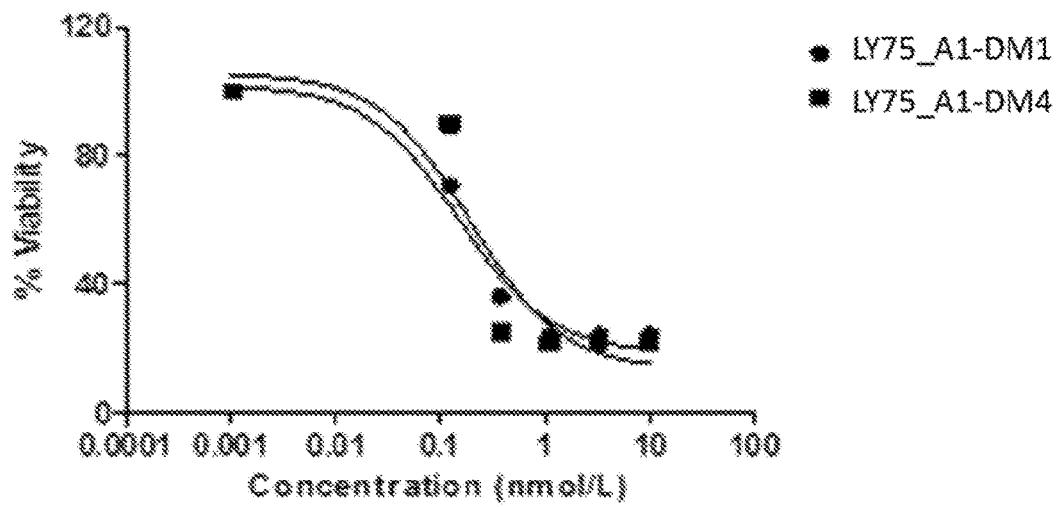
FIG. 3p depicts cytotoxic activity of anti-LY75 antibodies conjugated to either DM1 or DM4 in 5637 cells.
Figure 3Q:
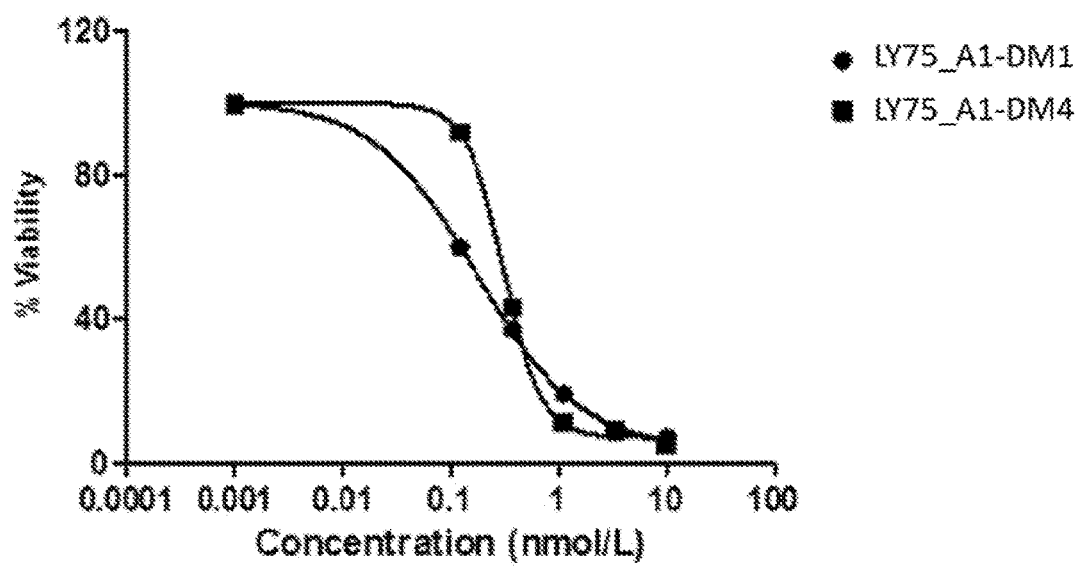
FIG. 3q depicts cytotoxic activity of anti-LY75 antibodies conjugated to either DM1 or DM4 in SW780 cells.

FIG. 3o shows the cytotoxic activity of anti-LY75 antibodies conjugated to DM1 and DM4 towards RT4 cells. FIG. 3p shows the cytotoxic activity of anti-LY75 antibodies conjugated to DM1 and DM4 towards 5637 cells. FIG. 3q shows the cytotoxic activity of anti-LY75 antibodies conjugated to DM1 and DM4 towards SW780 cells. These results demonstrate an increase in cytotoxic activity proportional to antibody concentration.

Example 12: Efficacy of DM1-Conjugated and DM4-Conjugated Anti-LY75 Monoclonal Antibodies in Head and Neck Cancer Cell Lines Materials
Cell stripper (Non-enzymatic cell dissociation) (MT-25-056CI) from Fisher Scientific, PA, USA.
PBS pH 7.4 (1×) (SH30028LS) from Fisher Scientific, PA, USA.
RPMI 1640 Media (MT-10-041-CM) from Fisher Scientific, PA, USA.
Cell Titer Glo (G7572) from Promega, Wis., USA.
Method
Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

Figure 3R:
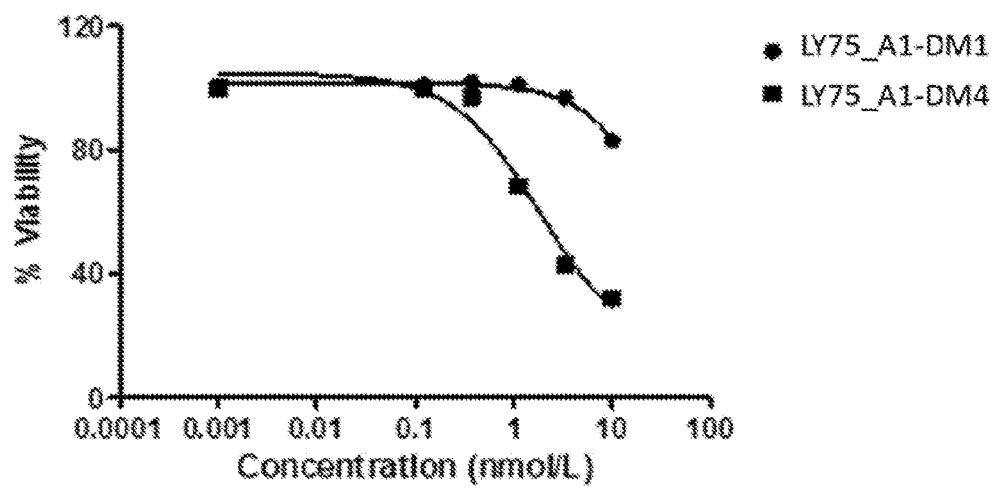
FIG. 3r depicts cytotoxic activity of anti-LY75 antibodies conjugated to either DM1 or DM4 in SCC-9 cells.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.
Results FIG. 3r shows the cytotoxic activity of anti-LY75 antibodies conjugated to DM1 and DM4 towards SCC-9 cells. These results demonstrate an increase in cytotoxic activity proportional to antibody concentration.

Example 13: Efficacy of DM1-Conjugated and DM4-Conjugated Anti-LY75 Monoclonal Antibodies in Oesophageal Cancer Cell Lines Materials
Cell stripper (Non-enzymatic cell dissociation) (MT-25-056CI) from Fisher Scientific, PA, USA.
PBS pH 7.4 (1×) (SH30028LS) from Fisher Scientific, PA, USA.
RPMI 1640 Media (MT-10-041-CM) from Fisher Scientific, PA, USA.
Cell Titer Glo (G7572) from Promega, Wis., USA.
Method
Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

Figure 3S:
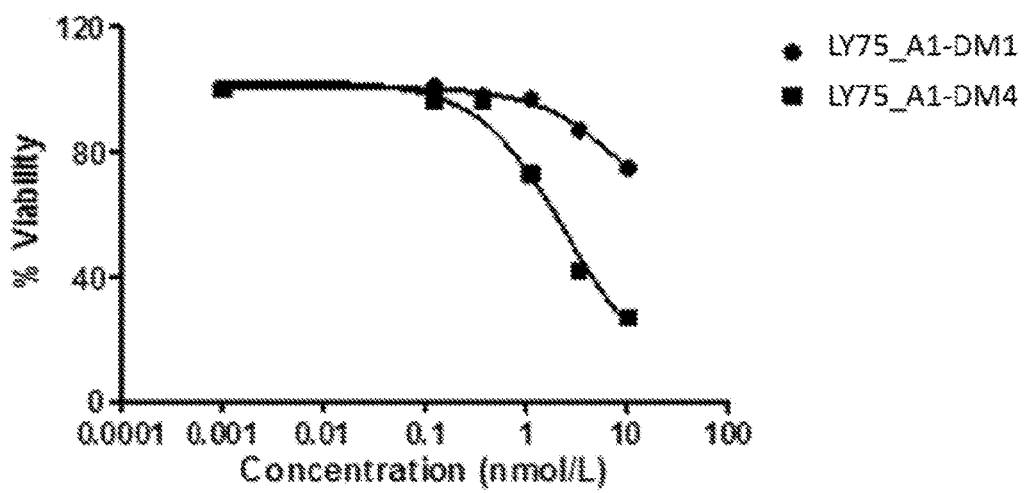
FIG. 3s depicts cytotoxic activity of anti-LY75 antibodies conjugated to either DM1 or DM4 in OE 19 cells.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.
Results FIG. 3s shows the cytotoxic activity of anti-LY75 antibodies conjugated to DM1 and DM4 towards OE 19 cells. These results demonstrate an increase in cytotoxic activity proportional to antibody concentration.

Example 14: Efficacy of DM1-Conjugated and DM4-Conjugated Anti-LY75 Monoclonal Antibodies in Ovarian Cancer Cell Lines Materials
Cell stripper (Non-enzymatic cell dissociation) (MT-25-056CI) from Fisher Scientific, PA, USA.
PBS pH 7.4 (1×) (SH30028LS) from Fisher Scientific, PA, USA.
RPMI 1640 Media (MT-10-041-CM) from Fisher Scientific, PA, USA.
Cell Titer Glo (G7572) from Promega, Wis., USA.
Method
Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Figure 3T:
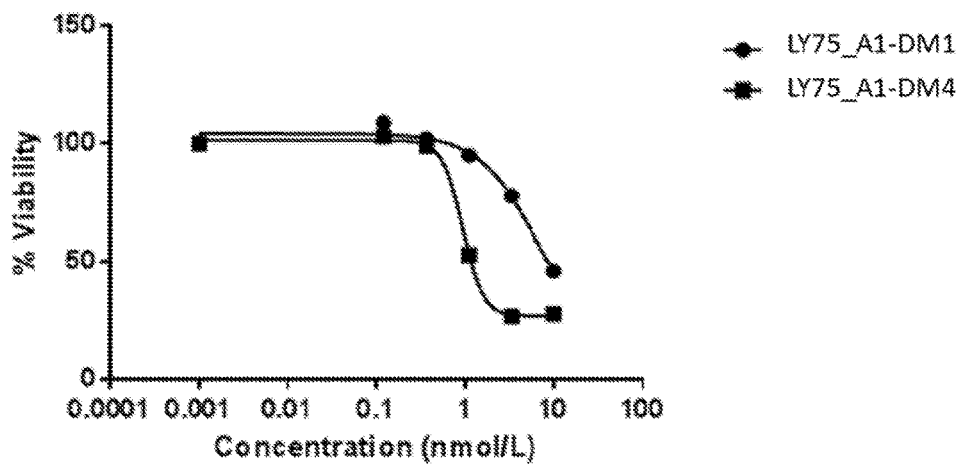
FIG. 3t depicts cytotoxic activity of anti-LY75 antibodies conjugated to either DM1 or DM4 in OVCAR-3 cells.
Figure 3U:
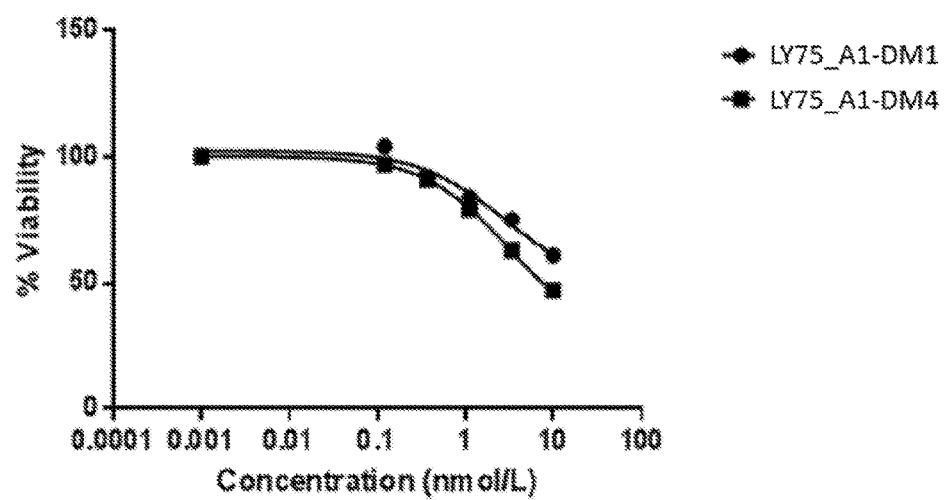
FIG. 3u depicts cytotoxic activity of anti-LY75 antibodies conjugated to either DM1 or DM4 in SK-OV-3 cells.

Results
FIG. 3t shows the cytotoxic activity of anti-LY75 antibodies conjugated to DM1 and DM4 towards OVCAR-3 cells. FIG. 3u shows the cytotoxic activity of anti-LY75 antibodies conjugated to DM1 and DM4 towards SK-OV-3 cells. These results demonstrate an increase in cytotoxic activity proportional to antibody concentration.

Figure 3V:
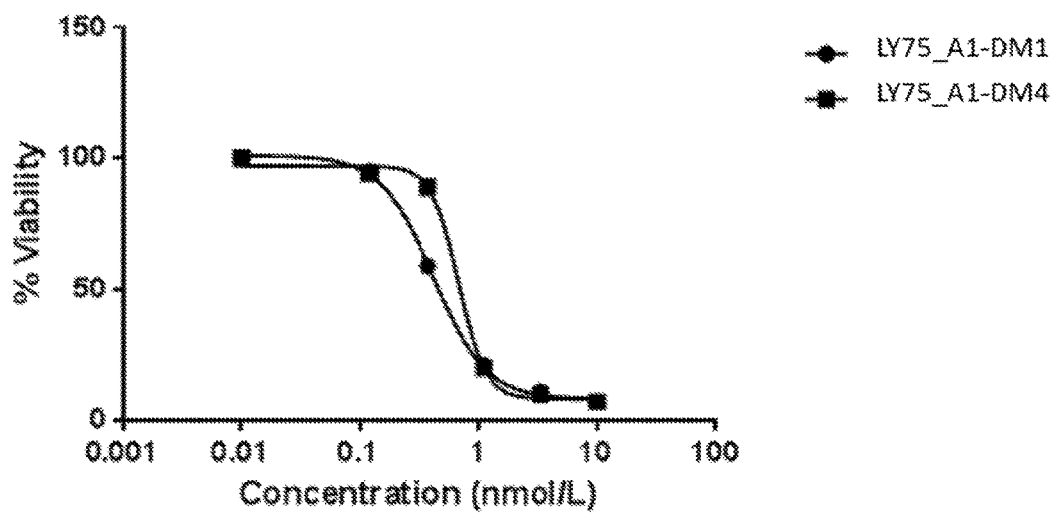
FIG. 3v depicts cytotoxic activity of anti-LY75 antibodies conjugated to either DM1 or DM4 in MOLP-8 cells.
Figure 3W:
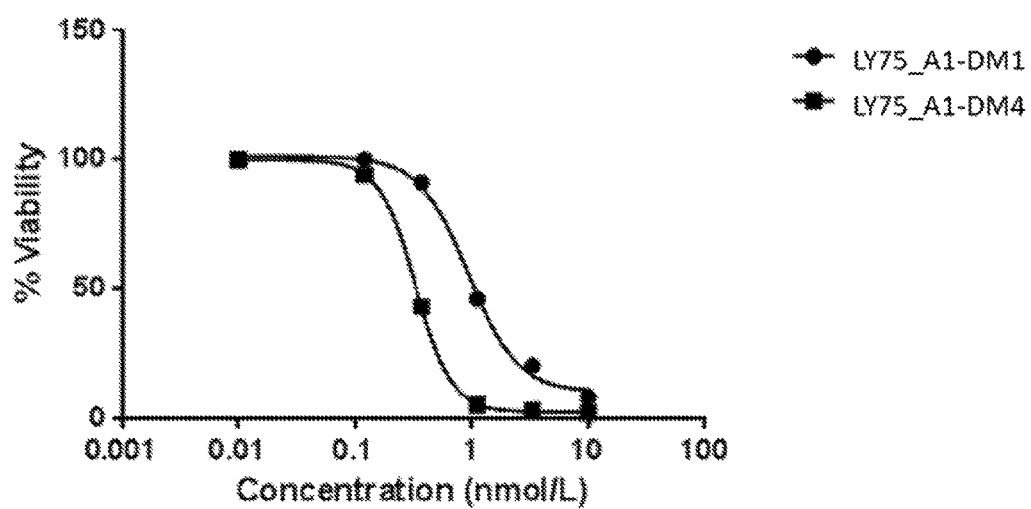
FIG. 3w depicts cytotoxic activity of anti-LY75 antibodies conjugated to either DM1 or DM4 in RPMI8226 cells.

Example 15: Efficacy of DM1-Conjugated and DM4-Conjugated Anti-LY75 Monoclonal Antibodies in Multiple Myeloma Cell Lines Materials
Cell stripper (Non-enzymatic cell dissociation) (MT-25-056CI) from Fisher Scientific, PA, USA.
PBS pH 7.4 (1×) (SH30028LS) from Fisher Scientific, PA, USA.
RPMI 1640 Media (MT-10-041-CM) from Fisher Scientific, PA, USA.
Cell Titer Glo (G7572) from Promega, Wis., USA.
Method
Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.
50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.
The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.
Results
FIG. 3v shows the cytotoxic activity of anti-LY75 antibodies conjugated to DM1 and DM4 towards MOLP-8 cells. FIG. 3w shows the cytotoxic activity of anti-LY75 antibodies conjugated to DM1 and DM4 towards RPMI8226 cells. These results demonstrate an increase in cytotoxic activity proportional to antibody concentration.

Figure 4A:
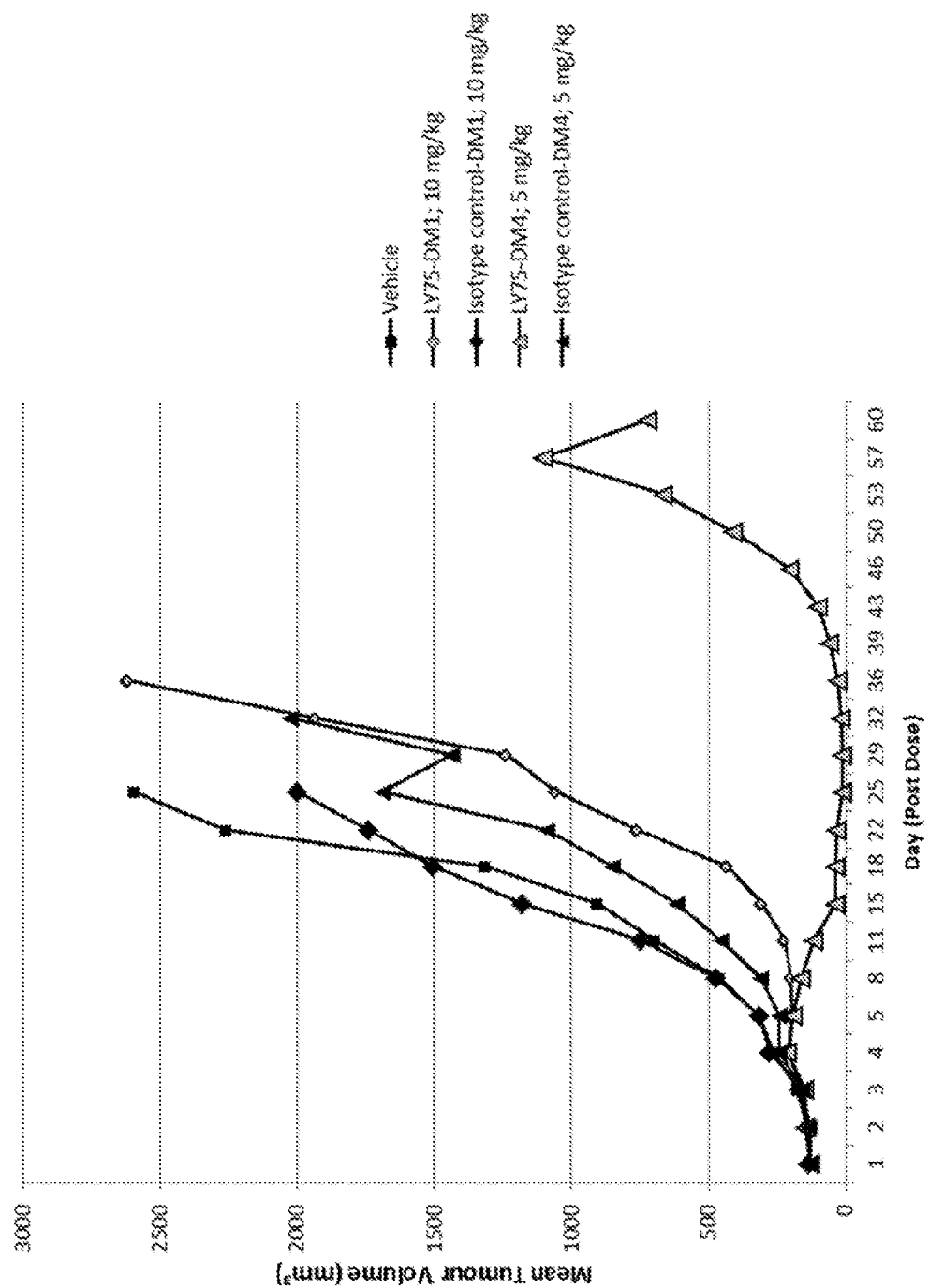
FIG. 4a depicts the efficacy of anti-LY75 antibodies conjugated to either DM1 or DM4 in Raji Burkitt's lymphoma SCID mouse xenograft model.

Example 16: Efficacy of DM1-Conjugated and DM4-Conjugated Anti-LY75 Monoclonal Antibodies in Raji Xenograft Models The efficacy of LY75_DM1 and LY75_DM4 were tested in subcutaneous Raji Burkitt's lymphoma SCID mouse xenograft model.
Immunodeficient SCID mice were inoculated subcutaneously with Raji (human Burkitt's lymphoma) tumour cells. Tumours were allowed to establish and mice were sorted into five treatment groups of 3-6 mice per group. When the mean tumour volume reached an average size of 129-132 mm3 per group, each group was treated with one of the following compounds, administered intravenously at the indicated dosages: Group 1 (Vehicle; phosphate buffered saline (PBS)); Group 2 (LY75_DM1; 10 mg/kg), Group 3 (Isotype control-DM1; 10 mg/kg), Group 4 (LY75_DM4; 5 mg/kg), Group 5 (isotype control-SPBDDM4; 5 mg/kg). A second dose was administered one week later. Body weights (BW) were monitored, the mice were examined frequently for health and adverse side effects, and tumours were measured twice weekly. Mice were euthanized when their tumours reached the tumour volume endpoint of 2000 mm3 or after 60 days, whichever came first. Efficacy was determined from tumour growth delay (TGD), the increase in median time-to-endpoint (TTE) and from logrank analysis of differences in Kaplan Meier survival curves in ADC-treated versus PBS-treat mice. The first five vehicle-treated control mice to reach endpoint were sampled for tumours that were processed by formalin fixation and paraffin embedded.
Results
FIG. 4a shows LY75_DM1 and LY75_DM4 each demonstrated significant anti-tumour activity and significantly extended survival in the Raji Burkitt's lymphoma SCID mouse xenograft model compared to controls; however, the 5 mg/kg LY75_DM4 doses were significantly more effective than the 10 mg/kg doses of LY75_DM1, resulting in 5 of 6 mice with complete but transient tumour regression. All treatments were well-tolerated and no clinical signs of toxicity were observed. These data suggest the potential for ADCs directed towards LY75, for example LY75_DM1 and LY75_DM4, to provide clinical benefit in the treatment of human non-Hodgkin lymphoma cancer patients.

Figure 4B:
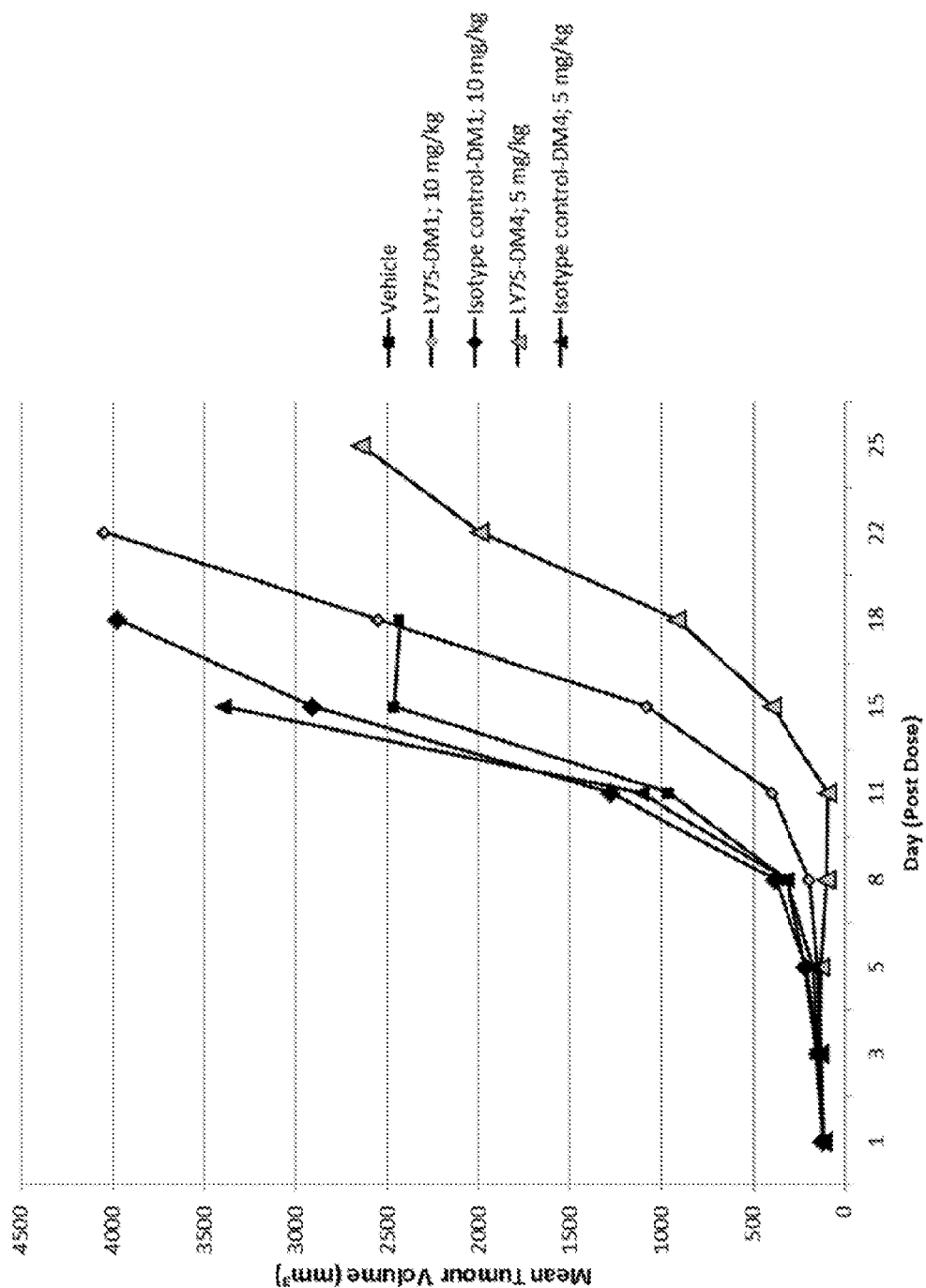
FIG. 4b depicts the efficacy of anti-LY75 antibodies conjugated to either DM1 or DM4 in Namalwa Burkitt's lymphoma SCID mouse xenograft model.

Example 17: Efficacy of DM1-Conjugated and DM4-Conjugated Anti-LY75 Monoclonal Antibodies in Namalwa Xenograft Models The efficacy of LY75_DM1 and LY75_DM4 were tested in subcutaneous Namalwa Burkitt's lymphoma SCID mouse xenograft model.
Immunodeficient SCID mice were inoculated subcutaneously with Namalwa (human Burkitt's lymphoma) tumour cells. Tumours were allowed to establish and mice were sorted into five treatment groups of 6 mice per group. When the mean tumour volume reached an average size of 114 mm3 per group, each group was treated with one of the following compounds, administered intravenously at the indicated dosages: Group 1 (Vehicle; phosphate buffered saline (PBS)); Group 2 (LY75_DM1; 10 mg/kg), Group 3 (Isotype control-DM1; 10 mg/kg), Group 4 (LY75_DM4; 5 mg/kg), Group 5 (isotype control-SPBDDM4; 5 mg/kg). Body weights (BW) were monitored, the mice were examined frequently for health and adverse side effects, and tumours were measured twice weekly. Mice were euthanized when their tumours reached the tumour volume endpoint of 2000 mm3 or after 60 days, whichever came first. Efficacy was determined from tumour growth delay (TGD), the increase in median time-to-endpoint (TTE), and from log rank analysis of differences in Kaplan Meier survival curves in ADC-treated versus PBS-treated mice. The first five vehicle-treated control mice to reach endpoint were sampled for tumours that were processed by formalin fixation and paraffin embedded.
Results
FIG. 4b shows LY75_DM1 and LY75_DM4 each demonstrated significant anti-tumour activity and survival extension in the Namalwa Burkitt's lymphoma SCID mouse xenograft model compared to controls; however, the 5 mg/kg LY75_DM4 dose was significantly more effective than the 10 mg/kg dose of LY75_DM1, causing a brief reduction in tumour volume. All treatments were well-tolerated and no clinical signs of toxicity were observed. These data suggest the potential for ADCs directed towards LY75, for example LY75_DM1 and LY75_DM4, to provide clinical benefit in the treatment of human non-Hodgkin lymphoma cancer patients.

Example 18: Efficacy of DM1-Conjugated and DM4-Conjugated Anti-LY75 Monoclonal Antibodies in Pancreatic Cancer Xenograft Models The efficacy of LY75_DM1 and LY75_DM4 were tested in the subcutaneous HPAFII pancreatic adenocarcinoma athymic nude mousexenograft model.

Immunodeficient athymic nude mice were inoculated subcutaneously with HPAFII (human pancreatic adenocarcinoma) tumor cells. Tumors were allowed to establish and mice were sorted into five treatment groups of 6 mice per group. When the mean tumor volume reached an average size of ~114 mm3/group, each group was treated with one of the following compounds, administered intravenously at the indicated dosages: Group 1 (Vehicle; phosphate buffered saline (PBS)); Group 2 (LY75_DM1; 10 mg/kg), Group 3 (Isotype control-DM1; 10 mg/kg), Group 4 (LY75_DM4; 5 mg/kg), Group 5 (isotype control-SPBDDM4; 5 mg/kg). Body weights (BW) were monitored, the mice were examined frequently for health and adverse side effects, and tumors were measured thrice weekly. Mice were euthanized when their tumors reached the tumor volume endpoint of 2000 mm3 or after 90 days, whichever came first. Efficacy was determined from the effect of treatment on tumor volume and from log rank analysis of differences in Kaplan-Meier survival curves in ADC-treated or PBS-treated mice. The tumors were sampled from vehicle-treated control mice and processed by formalin fixation and paraffin embedded.

Results

Figure 4C:
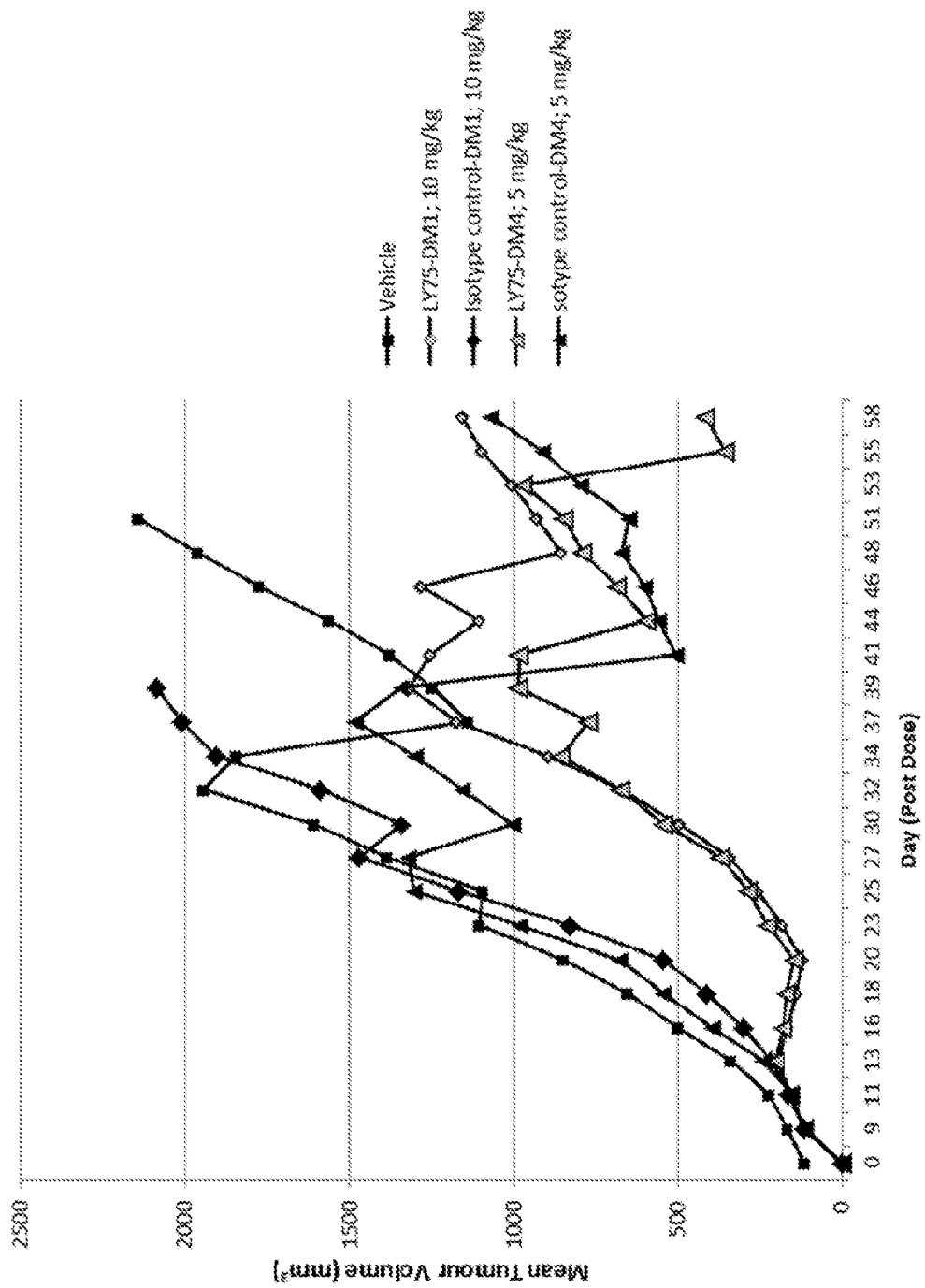
FIG. 4c depicts the efficacy of anti-LY75 antibodies conjugated to either DM1 or DM4 in HPAFII pancreatic adenocarcinoma athymic nude mousexenograft model.

FIG. 4c shows LY75_DM1 and LY75_DM4 displayed significant and similarly potent anti-tumor activity and survival extension in the HPAFII nude mouse xenograft model compared to controls. All treatments were well-tolerated and no clinical signs of toxicity were observed. These data suggest the potential for ADCs directed towards LY75, for example LY75_DM1 and LY75_DM4, to provide clinical benefit in the treatment of human pancreatic cancer patients.

Example 19: Efficacy of DM1-Conjugated and DM4-Conjugated Anti-LY75 Monoclonal Antibodies in Bladder Cancer Xenograft Models The efficacy of LY75_DM1 and LY75_DM4 were tested in the subcutaneous SW780 human bladder carcinoma SCID mouse xenograft model.

Immunodeficient athymic nude mice were inoculated subcutaneously with HPAFII (human pancreatic adenocarcinoma) tumor cells. Tumors were allowed to establish and mice were sorted into five treatment groups of 6 mice per group. When the mean tumor volume reached an average size of ~114 mm3/group, each group was treated with one of the following compounds, administered intravenously at the indicated dosages: Group 1 (Vehicle; phosphate buffered saline (PBS)); Group 2 (LY75_DM1; 1 mg/kg), Group 3 (LY75_DM1; 2.5 mg/kg), Group 4 (LY75_DM1; 5 mg/kg), Group 5 (LY75_DM4; 1 mg/kg)), Group 6 (LY75_DM4; 2.5 mg/kg)), Group 7 (LY75_DM4; 5 mg/kg)), Group 8 (isotype control-SPBDDM4; 5 mg/kg). Body weights (BW) were monitored, the mice were examined frequently for health and adverse side effects, and tumors were measured thrice weekly. Mice were euthanized when their tumors reached the tumor volume endpoint of 2000 mm3 or after 90 days, whichever came first. Efficacy was determined from the effect of treatment on tumor volume and from log rank analysis of differences in Kaplan-Meier survival curves in ADC-treated or PBS-treated mice. The tumors were sampled from vehicle-treated control mice and processed by formalin fixation and paraffin embedded.

Results

Figure 4D:
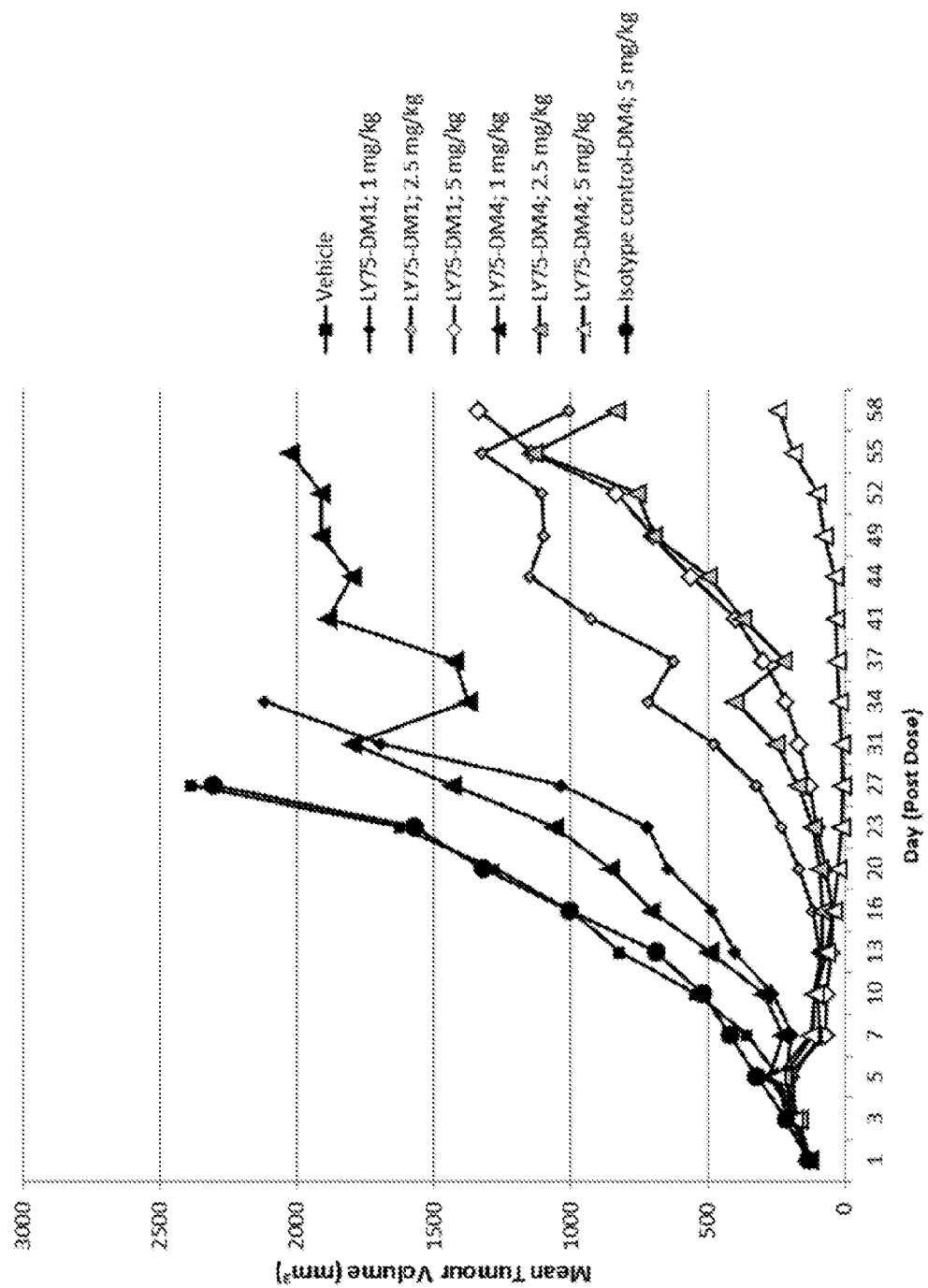
FIG. 4d depicts the efficacy of anti-LY75 antibodies conjugated to either DM1 or DM4 in SW780 human bladder carcinoma SCID mouse xenograft model.

FIG. 4d shows LY75_DM1 and LY75_DM4 displayed significant and similarly potent anti-tumor activity and survival extension in the SW780 nude mouse xenograft model compared to controls. All treatments were well-tolerated and no clinical signs of toxicity were observed. These data suggest the potential for ADCs directed towards LY75, for example LY75_DM1 and LY75_DM4, to provide clinical benefit in the treatment of human bladder cancer patients.

Example 20: Efficacy of DM1-Conjugated and DM4-Conjugated Anti-LY75 Monoclonal Antibodies in Breast Cancer Xenograft Models The efficacy of LY75_DM1 and LY75_DM4 were tested in the subcutaneous MDA-MB-468 athymic nude mouse xenograft model.

Immunodeficient athymic nude mice were inoculated subcutaneously with MDA-MB-468 (human triple negative breast adenocarcinoma) tumour cells. Tumours were allowed to establish and mice were sorted into seven treatment groups of 10 mice per group. When the mean tumour volume reached an average size of 167 mm3 per group, each group was treated with one of the following compounds, administered intravenously at the indicated dosages: Group 1 (Vehicle; 20 mM sodium succinate, pH 5.0, 6% trehalose, 0.04% polysorbate); Group 2 (LY75_DM1; 5 mg/kg), Group 3 (LY75_DM1; 10 mg/kg), Group 4 (LY75_DM4; 5 mg/kg), Group 5 (LY75_DM4; 2.5 mg/kg), Group 6 (LY75_DM4; 1 mg/kg), Group 7 (Isotype control-DM4; 5 mg/kg). Body weights (BW) were monitored, the mice were examined frequently for health and adverse side effects, and tumours were measured twice weekly. Mice were euthanized 82 days after tumour inoculation. Efficacy was determined from anti-tumour activity (mean tumour size in treatment group/mean tumour size in control group×100) and the increase in mean time-to-endpoint (TTE) in ADC-treated versus PBS-treated mice. The five largest tumours in vehicle-treated control mice on day 71 post inoculation were sampled processed by formalin fixation and paraffin embedded.

Results

Figure 4E:
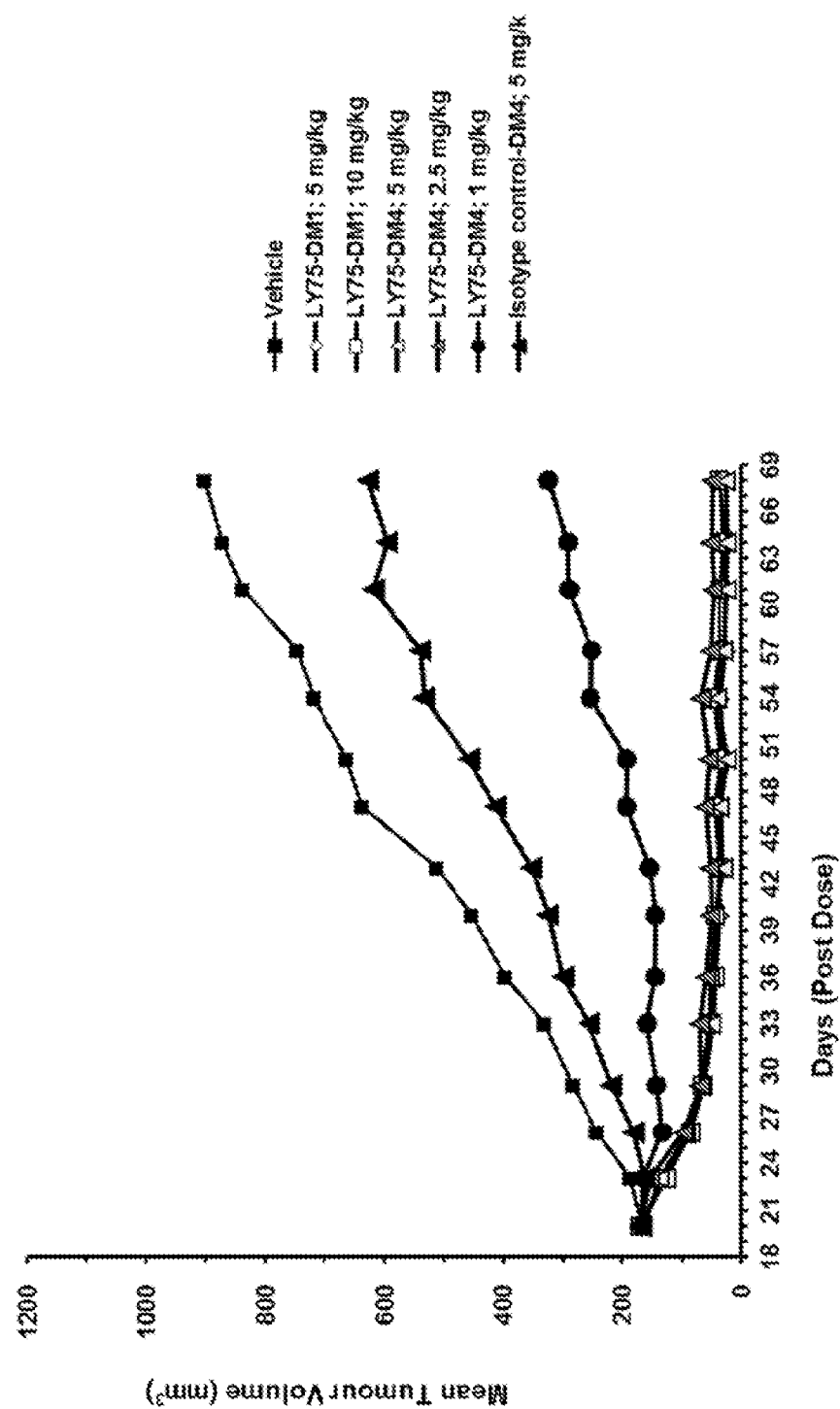
FIG. 4e depicts the efficacy of anti-LY75 antibodies conjugated to either DM1 or DM4 in MDA-MB-468 athymic nude mouse xenograft model.

FIG. 4e shows LY75_DM1 and LY75_DM4 each demonstrated dramatic anti-tumour activity in the MDA-MB-468 nude mouse xenograft model compared to controls. Dose dependent activity was observed with LY75_DM4, where 2.5 and 5 mg/kg were much more potent than 1 mg/kg. At 5 mg/kg, LY75_DM1 and LY75_DM4 were similarly effective. Sustained regressions in mean tumour volume were observed for LY75_DM1 at 10 and 5 mg/kg and LY75_DM4 at 5 and 2.5 mg/kg. All treatments were well-tolerated and no clinical signs of toxicity were observed. These data suggest the potential for ADCs directed towards LY75, for example LY75_DM1 and LY75_DM4, to provide clinical benefit in the treatment of human triple negative breast cancer patients.

Example 21: Efficacy of DM1-Conjugated and DM4-Conjugated Anti-LY75 Monoclonal Antibodies in Colorectal Cancer Xenograft Models The efficacy of LY75_DM1 and LY75_DM4 were tested in the subcutaneous COLO205 colorectal adenocarcinoma athymic nude mouse xenograft model.

Immunodeficient athymic nude mice were inoculated subcutaneously with COLO205 (human colorectal adenocarcinoma) tumor cells. Tumors were allowed to establish and mice were sorted into five treatment groups of 6 mice per group. When the mean tumor volume reached an average size of 117 mm3 per group, each group was treated with one of the following compounds, administered intravenously at the indicated dosages: Group 1 (Vehicle; phosphate buffered saline (PBS)); Group 2 LY75_DM1; 10 mg/kg), Group 3 (Isotype control-DM1; 10 mg/kg), Group 4 (LY75_DM4; 5 mg/kg), Group 5 (Isotype control-DM4; 5 mg/kg). A second dose was administered twelve days after the first. Body weights (BW) were monitored, the mice were examined frequently for health and adverse side effects, and tumors were measured twice weekly. Mice were euthanized when their tumors reached the tumor volume endpoint of 1000 mm3 or after 60 days, whichever came first. Efficacy was determined from tumor growth delay (TGD), the increase in median time-to-endpoint (TTE) and from log rank analysis of differences in Kaplan Meier survival curves in ADC-treated versus PBS-treated mice. The first five vehicle-treated control mice to reach endpoint were sampled for tumors that were processed by formalin fixation and paraffin embedded.

Results

Figure 4F:
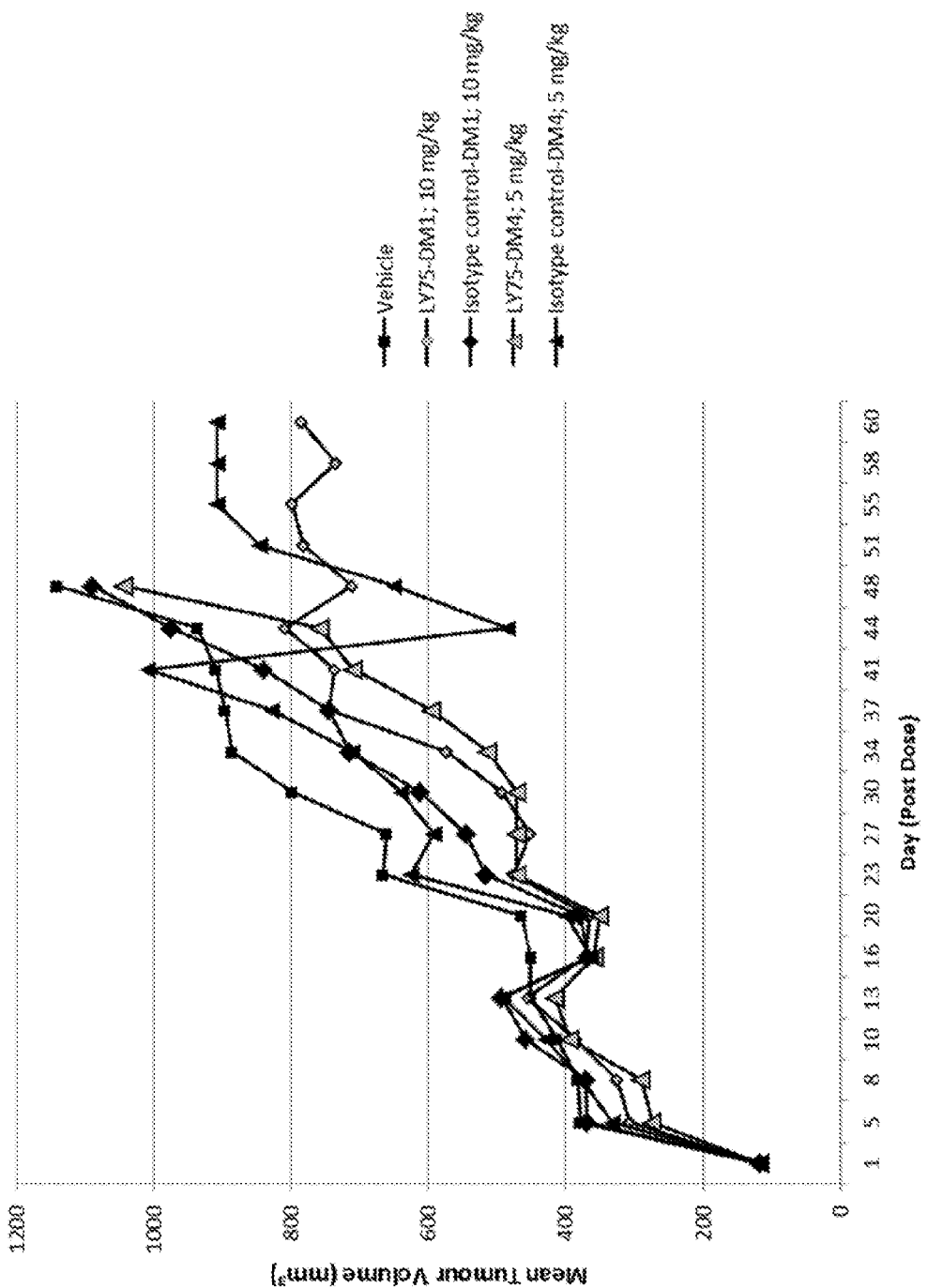
FIG. 4f depicts the efficacy of anti-LY75 antibodies conjugated to either DM1 or DM4 in COLO205 colorectal adenocarcinoma athymic nude mouse xenograft model.

FIG. 4f shows LY75_DM1 and LY75_DM4 exhibited similar modest anti-tumor activity and survival extension in the COLO205 colorectal adenocarcinoma nude mouse xenograft model compared to controls. All treatments were well-tolerated and no clinical signs of toxicity were observed. These data suggest the potential for ADCs directed towards LY75, for example LY75_DM1 and LY75_DM4, to provide clinical benefit in the treatment of human colorectal cancer patients.

Example 22: Toxicity of DM1-Conjugated and DM4-Conjugated Anti-LY75 Monoclonal Antibodies in Cynomolgus Monkeys Six male monkeys were assigned to the study with 2 monkeys/group. Either vehicle (PBS), LY75_DM4 (cleavable) or LY75_DM1 (non-cleavable) was administered twice (on Day 1 and Day 29) by a 15-minute intravenous infusion at 0 mg/kg/dose (PBS, vehicle), 5 mg/kg/dose (LY75_DM4, cleavable) or 10 mg/kg/dose (LY75_DM1, non-cleavable). Blood samples were collected for toxicokinetic evaluations prior to dose initiation (Day 1), and 1, 2, 3, 7, 14, 21 and 28 days post each dose. Blood samples for clinical pathology analyses were collected prior to dose initiation (Day 1), and 1, 3, 7, 14, 21 and 28 days post each dose (28 days post the 1st dose was also served as the pre-dose time point for the 2nd dose). All study animals were euthanized and necropsied following the final blood collection on Day 57. The plasma separated from each blood draw was isolated, frozen and shipped to Oxford BioTherapeutics, Inc. to be analyzed for ADC concentration by ELISA.

Treatment-related clinical pathology findings included a mild regenerative anemia and transient decreases in the blood leukocyte profile most notably in neutrophils counts. Anemia was observed in both animals treated with 5 mg/kg LY75_DM4 and in one of the two animals treated with 10 mg/kg LY75_DM1. Severe neutropenia with a nadir at one-week post dose and a rapid recovery in counts was observed in all animals; the nadir in absolute neutrophil count was lower in LY75_DM4 treated animals. There were no test article-related effects on the APTT and PT coagulation parameters. Serum chemistry changes included transient increases in AST, CK, LDH (in 1 of 2 animals in each treatment group) and globulin following administration of 5 mg/kg LY75_DM4 and 10 mg/kg LY75_DM1. In addition, a transient increase in the liver specific enzyme ALT was observed only in the LY75_DM4 treated animals. The short duration of and/or the magnitude of the increases in serum chemistry parameters suggest they were not adverse. There were no test-article related urinalysis findings. Upon examination at necropsy following a 4-week recovery period there were no treatment related gross pathology findings or changes in absolute and relative organ weights. Histopathology findings only in the thyroid gland (an alteration in the colloid morphology in follicles) and kidney (dilated tubules in the outer cortex), were graded as minimal severity; not associated with changes in other study parameters; and, not adverse and of minimal toxicological significance. Conclusion: Repeated dose treatment with two doses of 5 mg/kg LY75_DM4 or 10 mg/kg LY75_DM1 was well tolerated in cynomologus monkeys. All treatment-related toxicity findings were reversible following a 4-week recovery period.

Example 23: Epitope Characterisation of LY75_A1 by Competitive Fluorescence Activated Cell Sorting (FACS) Binding Analysis Method COLO205 cells (ATCC, catalog # CCL-222) were detached from tissue culture flasks with Cell Stripper (Cellgro, catalog # MT-25-056CI). Cells were washed and resuspended in FACS buffer (PBS+2% FBS), neutralized with growth media, and counted. Cells were plated at 50,000 cells per well in a V Bottom 96-well plate. Cells were washed once with FACS buffer (PBS (Fisher, catalog # SH30028-03)+2% FBS). An anti-LY75-mAb (Selected from Example 1) or LY75_A1 was added to wells starting at 250 nM and diluted serially 3 fold and applied to the relevant wells for 45 minutes on ice. Test wells that required single or multiple staining steps were left in FACS buffer as appropriate to ensure the final staining was completed simultaneously for all conditions tested. Two wells were left unstained in FACS buffer as controls.

After the incubation with blocking antibody, cells were washed twice in FACS buffer. The cells were resuspended in FACS buffer containing the anti-LY75-mAb conjugated to MCC-DM1 (1 nM) and incubated on ice for 45 minutes. The cells were washed as above and resuspended in FACS buffer plus 1 ug/ml mouse anti-maytansine antibody and incubated in ice for 45 minutes. The cells were washed as above and resuspended in FACS buffer containing 2 ug/ml goat anti-mouse kappa RPE. The cells were incubated on ice for 45 minutes then washed as above. The cells were resuspended in FACS buffer at 200 ul per well. Mean fluorescence intensity of each sample was determined using a Guava EasyCyte Plus HT Flow Cytometer (96 well plate formats) and the raw data was analyzed using the Guava Cytosoft.

Results

Figure 5A:
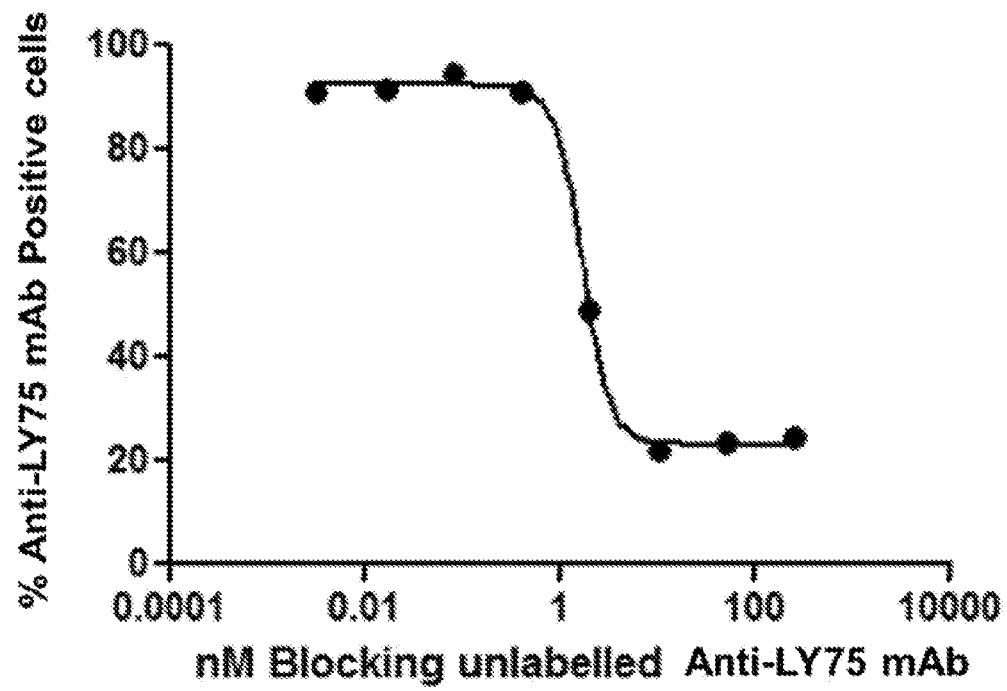
FIG. 5a shows competitive binding of anti-LY75-mAb and an anti-LY75-mAb conjugated to MCC-DM1.
Figure 5B:
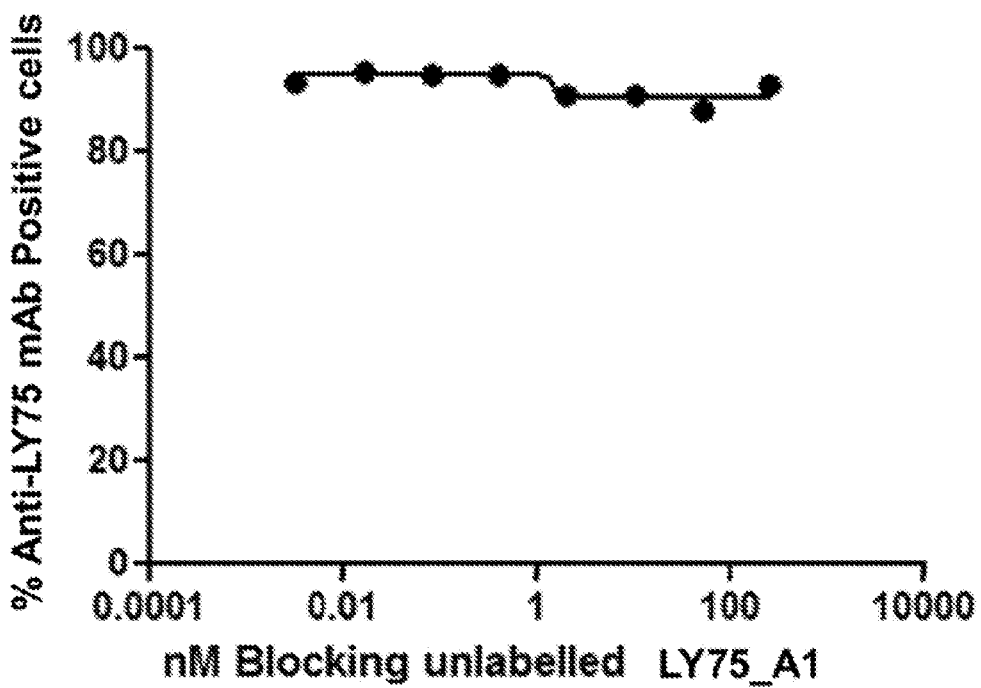
FIG. 5b shows non-competitive binding of LY75_A1 and an anti-LY75-mAb conjugated to MCC-DM1.
Figure 6A:
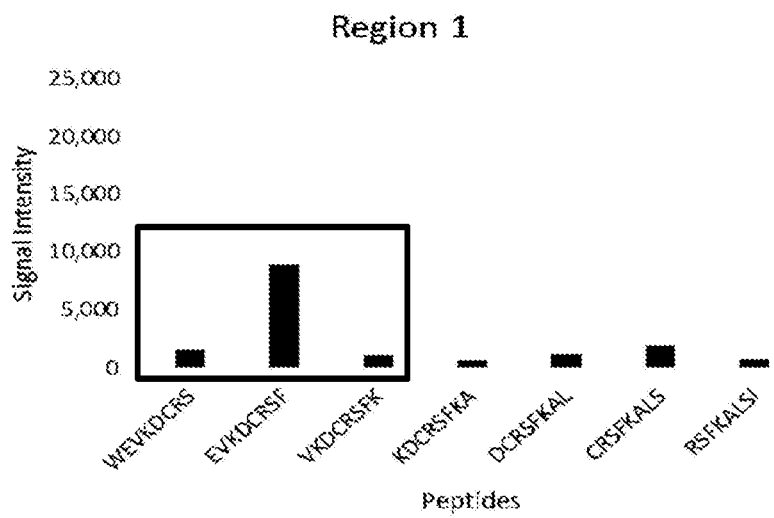
FIG. 6a-6j show graphical representations of the binding of antibody LY75_A1 to LY75 peptides on a peptide microarray.
Figure 6B:
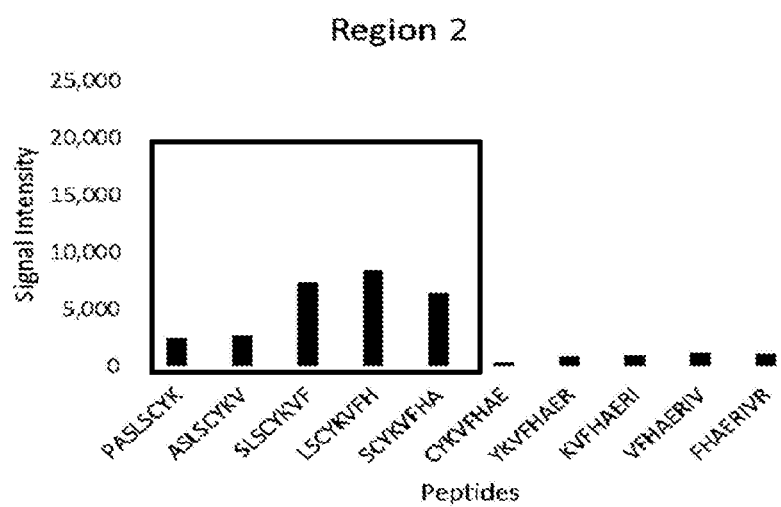
Figure 6C:
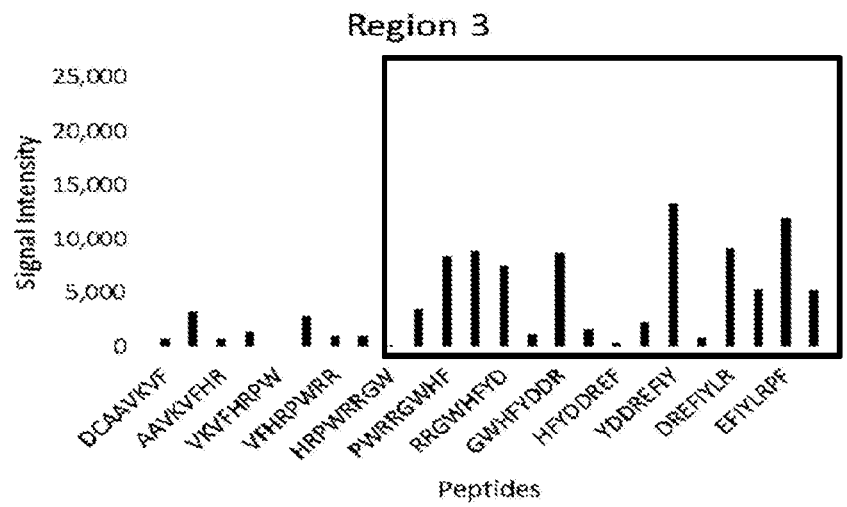
Figure 6D:
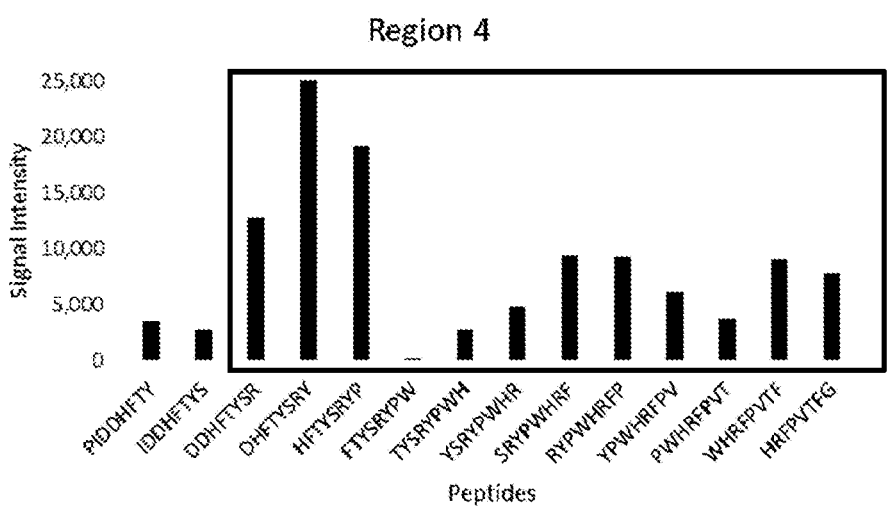
Figure 6E:
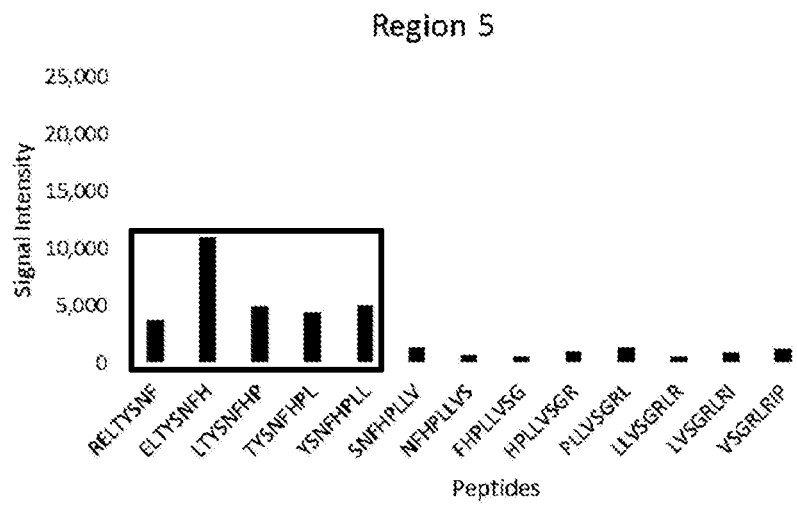
Figure 6F:
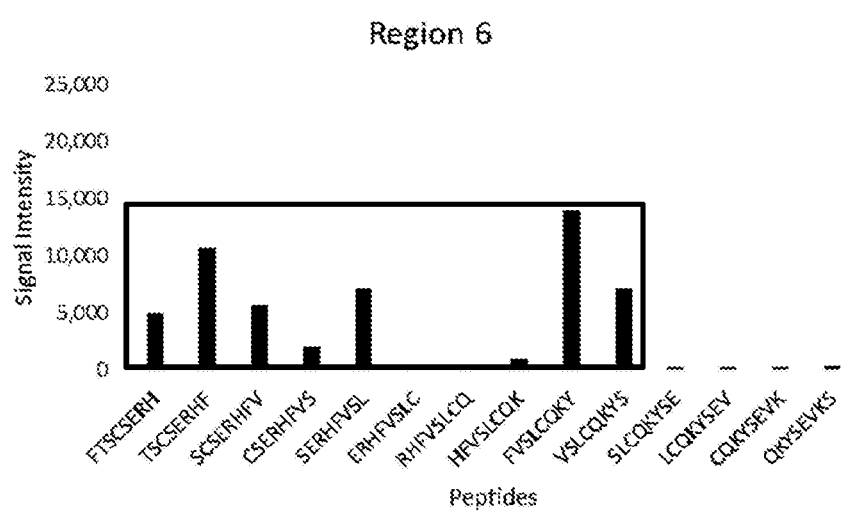
Figure 6G:
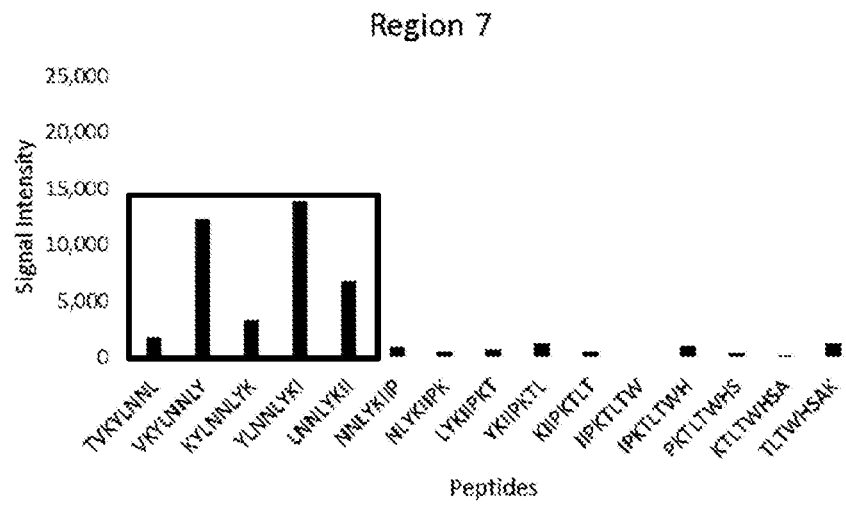
Figure 6H:
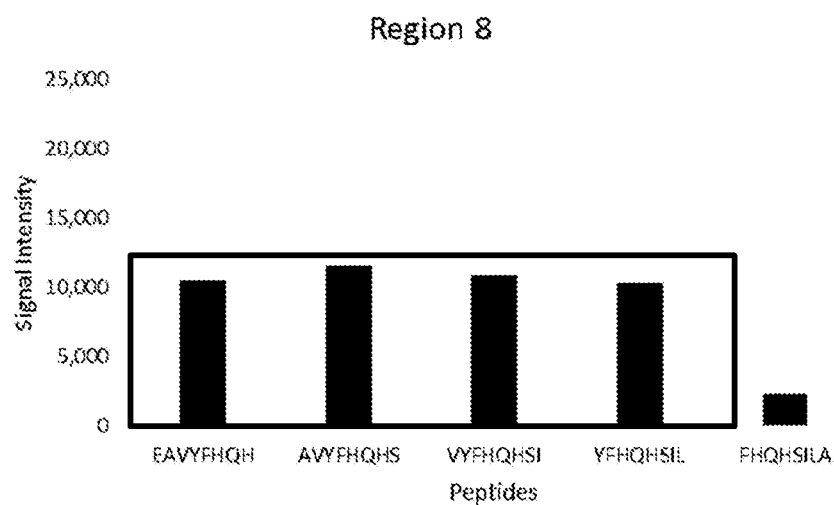
Figure 6I:
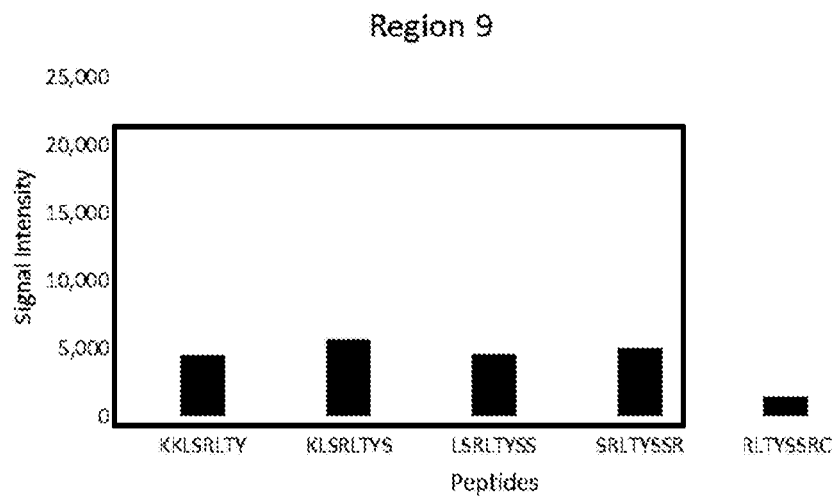
Figure 6J:
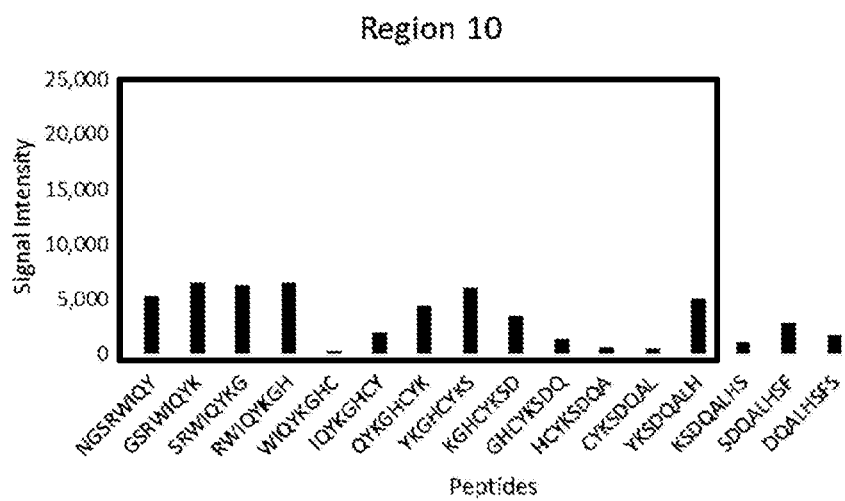

FIG. 5a shows blocking with the anti-LY75-mAb-MCC-DM1 reduced the binding of anti-LY75-mAb. Analysis of the binding of LY75_A1 to COLO205 cells showed that LY75_A1 is unable to block binding of anti-LY75-mAb-MCC-DM1 (see FIG. 5b). It can therefore be determined that the anti-LY75-mAb and LY75_A1 are non-competing antibodies and LY75_A1 recognizes a different and unique epitope of LY75 to that of other anti-LY75 antibodies.

Example 24: Epitope Characterization of LY75_A1 by Peptide Micro Array Assay

Method

The peptide microarray analysis was performed by LC Sciences, Houston Tex., in brief the method comprised the following steps:—Contiguous 8mer peptides of LY75 protein having one amino acid overlap spanning residues 216 to 1666 of the full length LY75 protein were synthesized and immobilized on a microarray chip. The chip comprised three panels such that the experiment was performed in in triplicate. The microarray was addressed with LY75_A1 to identify the peptides to which the antibody bound. The binding assay was performed under the following conditions:—The microarray comprising the contiguous peptides in triplicate was washed with 1 mL of binding buffer at 4° C. for 20 min. It was then incubated with 1 µg/mL LY75_A1 in binding buffer (pH 7.0) at 4° C. for 2 hrs. The array was again washed with 0.5 mL of washing buffer at 4° C. for 30 min then incubated with 25 ng/mL anti-human IgG Alexa 647 conjugate in binding buffer (pH 7.0) at 4° C. for 1 hr. The array was again washed with 0.5 mL of washing buffer at 4° C. for 30 min.

The array was then Scanned at 635 nm and PMT 500 and the signal Intensity was recorded. The peptide was classed as detectable if it was present in at least ⅔ legal duplicates. The average signal intensity of the replicates was reported as the final signal intensity.

Results

As can be seen from FIG. 6 antibody LY75_A1 showed specific binding to a number of peptides located on the array. The maximum signal seen for LY75_A1 binding was 25000 (scale 1-65535), with the average signal for all spots on the array being about 885. A signal intensity of 3000 was set as the background cut off point for non-specific binding. Based on the level of antibody binding signal intensity seen potential sequences forming the epitope for LY75_A1 were identified. These regions are shown in FIGS. 6a-6j and as SEQ ID NOs: 22-31.

Example 25: LY75_A1 Peptide Pull Down Assay

Method 1.1 Pull Down Assay

Recombinant LY75 protein was digested by on-bead tryptic proteolysis (Promega, US). The resulting digest peptides were recovered using a C18 capture column (Thermo Fisher Scientific). Purified peptides were then incubated with 200 µl of protein A beads cross-linked with LY75A1 antibody overnight at 4° C. Next day the unbound peptides were collected and the beads were washed with 1 ml of PBS twice. The antibody bound peptides were eluted from beads by heating them at 90° C. in 100 µl of PBS for 5 minutes. This elution step was repeated.

1.2 Mass Spectrometry

Samples were analysed by liquid chromatography-mass spectrometry using a Waters nanoACQUITY UPLC System fitted with a nanoACQUITY BEH 130 C18 column, 75 µm×250 mm (186003545) and a LTQ Orbitrap Velos (Thermo Fisher Scientific). Peptides were eluted with a 300 nl/min gradient increasing from 3% to 35% acetonitrile over 120 min. Full-scan mass spectra were acquired at 60000 resolving power between 400-2000 m/z mass range in the Orbitrap. In each cycle, the twenty most intense peptides were selected for CID MS/MS scans in the linear ion trap with nanospray ion source fitted on the instrument.

1.3 Amino Acid Sequence Analysis of Peptide

The raw data generated from the LTQ Orbitrap Velos was processed through the Mascot software (Matrix Science) which uses the Mowse algorithm (Curr Biol. 1993 Jun. 1; 3(6):327-3) to infer amino acids sequences from the peak lists by searching against a sequence database consisting of Ensembl (http://www.ensembl.org/index.html), IPI (www.e-bi.ac.uk/IPI/IPIhuman.html) and SwissProt (http://www.uniprot.org) along with contaminant protein sequences. Criteria for peptide identification included trypsin digestion, up to 2 missed cleavage sites and various biological and chemical modifications (oxidized methionine, cysteine modification by MMTS or iodoacetamide and phosphorylation of serine, threonine and tyrosine). Peptides ranked 1 with an expectation value of 0.05% or less, an ion score of 28 or higher were loaded into our OGAP database.

1.4 Discrimination of LY75 Associated Peptides

The process to identify LY75 used the peptide sequences obtained experimentally by mass spectrometry, as described above, of naturally occurring human proteins to identify and organize coding exons in the published human genome sequence. These experimentally determined sequences were compared with the OGAP® database which was compiled by processing and integration of peptide masses, peptide signatures, ESTs and Public Domain Genomic Sequence Data as described in International Patent Application WO2009/087462.

Results

The results of the peptide pull down assay using antibody LY75_A1 are shown in Table 1 below and in FIG. 7. Peptides which were identified in both peptide elutions 1a and 1b in the pull down assay and in the microarray assay were considered to be the most likely candidates for forming the epitope.

TABLE 1

Comparison of peptide microarray and peptide pull down experiments.

| Peptide Identified by Microarray Assay | | Peptide Identified by Pull Down Assay |
|---|---|---|
| Region 1 | (aa609-618) | - |
| Region 2 | (aa651-662) | - |
| Region 3 | (aa761-780) | GWHFYDDR (765-772) |
| Region 4 | (aa883-901) | ISEWPIDDHFTYSR (877 to 890) FPVTFGEECLYMSAK (896-910) |
| Region 5 | (aa1029-1040) | ELTYSNFHPLLVSGR (1030-1044) |
| Region 6 | (aa1077-1093) | HFVSLCQK (1084-1091) |
| Region 7 | (aa1107-1118) | QTLQNASETVK (1099-1109) |

TABLE 1-continued

Comparison of peptide microarray and peptide pull down experiments.

| Peptide Identified by Microarray Assay | Peptide Identified by Pull Down Assay |
|---|---|
| Region 8 (aa1368-1378) | - |
| Region 9 (aa1518-1528) | - |
| Region 10 (aa1535-1554) | - |

Table 1 shows that a number of overlapping LY75 peptide regions were identified in both the Peptide Microarray assay and in both elutions 1a and 1b the Peptide pull down assay. These regions are considered to be the most likely to contain the epitope recognized by antibody LY75_A1 as they are bound by LY75_A1 tested by both techniques employed.

SEQUENCE LIST:

| SEQ ID No | Description | Sequence |
|---|---|---|
| 1 | A1_VH aa | EVQLVESGGGLVKPGGSLRLSCAAS GFTYSNAWMSWVRQAPGK-GLEWVGR IKSKTDGGTTDYAAPVQGRFTISRD DSKNTLYLQMNSLKTEDTAVYYCTI FGVVSFDYWGQGTLVTVSS |
| 2 | A1_VL aa | DVQMTQSPSSLSASVGDRVTITCRA SQSISDYLSWYQQRPGKAPNLLIYA ASNLKTGVPSRFSGSGSGTDFTLTI STLQPEDFATYYCQQSYRSPWTFGQ GTKVEIKR |
| 3 | A1_VH nt | gaggtgcagctggtggagtctggg gaggcttggtaaagccggggggtc ccttagactctcctgtgcagcctct ggcttcacttacagtaacgcctgga tgagctgggtccgccaggctccagg gaaggggctggagtgggttggcgt attaaaagcaaaactgatggtggga caacagactacgctgcacccgtgca aggcagattcaccatctcaagagat gattcaaaaaacacgctgtatctgc aaatgaacagcctgaaaaccgagga cacagccgtgtattactgtacgatt tttggagtggttagctttgactact ggggccagggaacccctggtcaccgt ctcctca |
| 4 | A1_VL nt | gacgtccagatgacccagtctccat cctccctgtctgcatctgttggaga cagagtcaccatcacttgccgggca agtcagagcattagcgactatttaa gttggtatcagcagagaccaggga agcccctaacctcctgatctatgct gcatccaatttaaagactgggtcc catcaaggttcagtggcagtggatc tgggacagatttcactctcaccatc agcactctgcaacctgaagattttg caacgtactactgtcaacagagtta caggtccccgtgacgttcggccaa gggaccaaggtggaaatcaaacga |
| 5 | A1_VH_CDR1 aa | NAWMS |
| 6 | A1_VH_CDR2 aa | RIKSKTDGGTTDYAAPVQG |
| 7 | A1_VH_CDR3 aa | FGVVSFDY |
| 8 | A1_VL_CDR1 aa | RASQSISDYLS |
| 9 | A1_VL_CDR2 aa | AASNLKT |

SEQUENCE LIST:

| SEQ ID No | Description | Sequence |
|---|---|---|
| 10 | A1_VL_CDR3 aa | QQSYRSPWT |
| 11 | VH3\|3-15/D4\|411 | EVQLVESGGGLVKPGGSLRLSCAAS GFTFSNAWMSWVRQAPGKGLEWVGR IKSKTDGGIIDYAAPVKGRFTISRD DSKNTLYLQMNSLKTEDTAVYYCTT TTVT |
| 12 | JH4 | YFDYWGQGTLVTVSS |
| 13 | O12 | DIQMTQSPSSLSASVGDRVTITCRA SQSISSYLNWYQQKPGKAPKLLIYA ASSLQSGVPSRFSGSGSGTDFTLTI SSLQPEDFATYYCQQSYS |
| 14 | JK1 | WTFGQGTKVEIKR |
| 15 | LY75 (DEC-205) | MRTGWATPRRPAGLLMLLFWFFDLA EPSGRAANDPFTIVHGNTGKCIKPV YGWIVADDCDETEDKLWKWVSQHRL FHLHSQKCLGLDITKSVNELRMFSC DSSAMLWWKCEHHSLYGAARYRLAL KDGHGTAISNASDVWKKGGSEESLC DQPYHEIYTRDGNSYGRPCEFPFLI DGTWHHDCILDEDHSGPWCATTLNY EYDRKWGICLKPENGCEDNWEKNEQ FGSCYQFNTQTALSWKEAYVSCQNQ GADLLSINSAAELTYLKEKEGIAKI FWIGLNQLYSARGWEWSDHKPLNFL NWDPDRPSAPTIGGSSCARMDAESG LWQSFSCEAQLPYVCRKPLNNTVEL TDVWTYSDTRCDAGWLPNNGFCYLL VNESNSWDKAHAKCKAFSSDLISIH SLADVEVVVTKLHNEDIKEEVWIGL KNINIPTLFQWSDGTEVTLTYWDEN EPNVPYNKTPNCVSYLGELGQWKVQ SCEEKLKYVCKRKGEKLNDASSDKM CPPDEGWKRHGETCYKIYEDEVPFG TNCNLTITSRFEQEYLNDLMKKYDK SLRKYFWTGLRDVDSCGEYNWATVG GRRRAVTFSNWNFLEPASPGGCVAM STGKSVGKWEVKDCRSFKALSICKK MSGPLGPEEASPKPDDPCPEGWQSF PASLSCYKVFHAERIVRKRNWEEAE RFCQALGAHLSSFSHVDEIKEFLHF LTDQFSGQHWLWIGLNKRSPDLQGS WQWSDRTPVSTIIMPNEFQQDYDIR DCAAVKVFHRPWRRGWHFYDDREFI YLRPFACDTKLEWVCQIPKGRTPKT PDWYNPDRAGIHGPPLIIEGSEYWF VADLHLNYEEAVLYCASNHSFLATI TSFVGLKAIKNKIANISGDGQKWWI RISEWPIDDHFTYSRYPWHRFPVTF GEEECLYMSAKTWLIDLGKPTDCSTK LPFICEKYNVSSLEKYSPDSAAKVQ CSEQWIPFQNKCFLKIKPVSLTFSQ ASDTCHSYGGTLPSVLSQIEQDFIT SLLPDMEATLWIGLRWTAYEKINKW TDNRELTYSNFHPLLVSGRLRIPEN FFEEESRYHCALILNLQKSPFTGTW NFTSCSERHFVSLCQKYSEVKSRQT LQNASETVKYLNNLYKIIPKTLTWH SAKRECLKSNMQLVSITDPYQQAFL SVQALLHNSSLWIGLFSQDDELNFG WSDGKRLHFSRWAETNGQLEDCVVL DTDGFWKTVDCNDNQPGAICYYSGN ETEKEVKPVDSVKCPSPVLNTPWIP FQNCCYNFIITKNRHMATTQDEVHT KCQKLNPKSHILSIRDEKENNFVLE QLLYFNYMASWVMLGITYRNKSLMW FDKTPLSYTHWRAGRPTIKNEKFLA GLSTDGFWDIQTFKVIEEAVYFHQH SILACKIEMVDYKEEYNTTLPQFMP |

SEQUENCE LIST:

| SEQ ID No | Description | Sequence |
|---|---|---|
|  |  | YEDGIYSVIQKKVTWYEALNMCSQS GGHLASVHNQNGQLFLEDIVKRDGF PLWVGLSSHDGSESSFEWSDGSTFD YIPWKGQTSPGNCVLLDPKGTWKHE KCNSVKDGAICYKPTKSKKLSRLTY SSRCPAAKENGSRWIQYKGHCYKSD QALHSFSEAKKLCSKHDHSATIVSI KDEDENKFVSRLMRENNNITMRVWL GLSQHSVDQSWSWLDGSEVTFVKWE NKSKSGVGRCSMLIASNETWKKVEC EHGFGRVVCKVPLGPDYTAIAIIVA TLSILVLMGGLIWFLFQRHRLHLAG FSSVRYAQGVNEDEIMLPSFHD |
| 16 | A1_VH_FR1 | EVQLVESGGGLVKPGGSLRLSCAAS GFTYS |
| 17 | A1_VH_FR2 | WVRQAPGKGLEWVG |
| 18 | A1_VH_FR3 | RFTISRDDSKNTLYLQMNSLKTEDT AVYYCTI |
| 19 | A1_VH_FR4 | WGQGTLVTVSS |
| 20 | A1_VL_FR1 | DVQMTQSPSSLSASVGDRVTITC |
| 21 | A1_VL_FR2 | WYQQRPGKAPNLLIY |
| 22 | A1_VL_FR3 | GVPSRFSGSGSGTDFTLTISTLQPE DFATYYC |
| 23 | A1_VL_FR4 | FGQGTKVEIKR |
| 24 | LY75 609-618 | WEVKDCRSFK |
| 25 | LY75 651-662 | PASLSCYKVFHA |
| 26 | LY75 761-780 | PWRRGWHFYDDREFIYLRPF |
| 27 | LY75 883-901 | DDHFTYSRYPWHRFPVTFG |
| 28 | LY75 1029-1040 | RELTYSNFHPLL |
| 29 | LY75 1077-1093 | FTSCSERHFVSLCQKYS |
| 30 | LY75 1107-1118 | TVKYLNNLYKII |
| 31 | LY75 1368-1378 | EAVYFHQHSIL |
| 32 | LY75 1518-1528 | KKLSRLTYSSC |
| 33 | LY75 1535-1554 | NGSRWIQYKGHCYKSDQALH |
| 34 | LY75 877-901 | ISEWPIDDHFTYSRYPWHRFPVTFG |
| 35 | LY75 1099-1118 | QTLQNASETVKYLNNLYKII |
| 36 | LY75 883-892 | DDHFTYSRYP |
| 37 | LY75 1077-1091 | FTSCSERHFVSLCQK |

The invention claimed is:

1. An isolated antibody, or an antigen-binding portion thereof, that binds to LY75, said antibody comprising:
   a) a heavy chain variable region comprising:
      i) a first vhCDR comprising SEQ ID NO: 5;
      ii) a second vhCDR comprising SEQ ID NO: 6; and
      iii) a third vhCDR comprising SEQ ID NO: 7; and
   b) a light chain variable region comprising:
      i) a first vlCDR comprising SEQ ID NO: 8;
      ii) a second vlCDR comprising SEQ ID NO: 9; and
      iii) a third vlCDR comprising SEQ ID NO: 10.

2. An isolated antibody or an antigen-binding portion thereof, comprising a heavy chain variable region comprising SEQ ID NO: 1 and a light chain variable region comprising SEQ ID NO: 2.

3. The isolated antibody or an antigen-binding portion thereof according to claim 1 further comprising a covalently-attached moiety.

4. The isolated antibody or an antigen-binding portion thereof according to claim 3, wherein said moiety is a drug.

5. The isolated antibody or an antigen-binding portion thereof according to claim 4, wherein said drug is selected from the group consisting of a maytansinoid, a dolastatin, a hemiasterlin, an auristatin, a trichothecene, a calicheamicin, CC1065 and derivatives thereof.

6. The isolated antibody or an antigen-binding portion thereof according to claim 5, wherein said drug is a maytansinoid selected from the group consisting of DM4 and DM1.

7. The isolated antibody according to claim 1, wherein said antibody induces antibody-dependent cell-mediated cytotoxicity (ADCC) and/or complement dependent cytotoxicity (CDC).

8. The isolated antibody according to claim 7, wherein the antibody is an engineered antibody having increased binding to Fc receptors and/or increased potency for ADCC, and/or a bispecific antibody.

9. A pharmaceutical composition comprising an antibody or antigen binding portion thereof according to claim 1, together with one or more pharmaceutically-acceptable diluents, excipients or carriers.

10. A nucleic acid encoding a heavy chain of the antibody or an antigen-binding portion thereof of claim 1.

11. A nucleic acid encoding a light chain of the antibody or an antigen-binding portion thereof of claim 1.

12. An expression vector comprising the nucleic acid of claim 10 operably linked to one or more regulatory elements and/or the nucleic acid of claim 11 operably linked to one or more regulatory elements.

13. A host cell comprising:
   (i) an expression vector comprising the nucleic acid of claim 10 operably linked to one or more regulatory elements and the nucleic acid of claim 11 operably linked to one or more regulatory elements; or
   (ii) a first expression vector comprising the nucleic acid of claim 10 operably linked to one or more regulatory elements and a second expression vector comprising the nucleic acid of claim 11 operably linked to one or more regulatory elements.

14. A method of making an antibody or an antigen-binding portion thereof, comprising culturing a host cell according to claim 13 under conditions where the antibody or an antigen-binding portion thereof is expressed and optionally isolating the antibody or an antigen-binding portion thereof.

15. A method of treating cancer expressing LY75 comprising administering to a patient in need thereof an antibody or an antigen-binding portion thereof of claim 1 wherein the antibody or antigen-binding portion comprises a covalently attached drug conjugate.

16. The method of claim 15, wherein the covalently attached drug conjugate is a maytansinoid.

17. The method according to claim 15 wherein the antibody induces antibody-dependent cell-mediated cytotoxicity (ADCC) and/or complement dependent cytotoxicity (CDC).

18. The method according to claim 15 wherein said cancer is selected from the group consisting of pancreatic cancer, ovarian cancer, breast cancer, colorectal cancer, esophageal cancer, skin cancer, thyroid cancer, lung cancer, kidney cancer, liver cancer, head and neck cancer, bladder cancer, gastric cancer, leukaemia, myeloma, and lymphoma.

19. The method of claim 18, wherein the cancers is selected from the group consisting of bladder cancer, pancreatic cancer, triple-negative breast cancer and DLBCL.

20. The method of claim 16, wherein the maytansinoid is DM4.

21. The method according to claim 18 wherein said leukaemia is acute myeloid leukaemia or chronic lymphocytic leukaemia, said myeloma is multiple myeloma and said lymphoma is selected from the group consisting of B-Cell Lymphoma, Follicular Lymphoma, Mantle Cell Lymphoma, Lymphoma of Mucosa-Associated Lymphoid Tissue (MALT), T-Cell/Histiocyte-Rich B-Cell Lymphoma, Burkitt's Lymphoma, Lymphoplasmacytic Lymphoma, Small Lymphocytic Lymphoma, Marginal Zone Lymphoma, T Cell Lymphoma, Peripheral T-Cell Lymphoma, Anaplastic Large Cell Lymphoma and Angio Immunoblastic T-Cell Lymphoma.

* * * * *

SEQUENCE LISTING

<160> NUMBER OF SEQ ID NOS: 37

<210> SEQ ID NO 1
<211> LENGTH: 119
<212> TYPE: PRT
<213> ORGANISM: Human

<400> SEQUENCE: 1

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Tyr Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Gln Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Ile Phe Gly Val Val Ser Phe Asp Tyr Trp Gly Gln Gly
            100                 105                 110
```

```
Thr Leu Val Thr Val Ser Ser
        115

<210> SEQ ID NO 2
<211> LENGTH: 108
<212> TYPE: PRT
<213> ORGANISM: Human

<400> SEQUENCE: 2

Asp Val Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Tyr
            20                  25                  30

Leu Ser Trp Tyr Gln Gln Arg Pro Gly Lys Ala Pro Asn Leu Leu Ile
        35                  40                  45

Tyr Ala Ala Ser Asn Leu Lys Thr Gly Val Pro Ser Arg Phe Ser Gly
    50                  55                  60

Ser Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Ser Tyr Arg Ser Pro Trp
                85                  90                  95

Thr Phe Gly Gln Gly Thr Lys Val Glu Ile Lys Arg
            100                 105

<210> SEQ ID NO 3
<211> LENGTH: 357
<212> TYPE: DNA
<213> ORGANISM: Human

<400> SEQUENCE: 3
gaggtgcagc tggtggagtc tgggggaggc ttggtaaagc cggggggggtc ccttagactc      60 tcctgtgcag cctctggctt cacttacagt aacgcctgga tgagctgggt ccgccaggct     120
ccagggaagg ggctggagtg ggttggccgt attaaaagca aaactgatgg tgggacaaca     180
gactacgctg cacccgtgca aggcagattc accatctcaa gagatgattc aaaaaacacg     240
ctgtatctgc aaatgaacag cctgaaaacc gaggacacag ccgtgtatta ctgtacgatt     300
tttggagtgg ttagctttga ctactggggc cagggaaccc tggtcaccgt ctcctca       357

<210> SEQ ID NO 4
<211> LENGTH: 324
<212> TYPE: DNA
<213> ORGANISM: Human

<400> SEQUENCE: 4
gacgtccaga tgacccagtc tccatcctcc ctgtctgcat ctgttggaga cagagtcacc      60
atcacttgcc gggcaagtca gagcattagc gactatttaa gttggtatca gcagagacca     120
gggaaagccc ctaacctcct gatctatgct gcatccaatt taaagactgg ggtcccatca     180
aggttcagtg gcagtggatc tgggacagat ttcactctca ccatcagcac tctgcaacct     240
gaagattttg caacgtacta ctgtcaacag agttacaggt ccccgtggac gttcggccaa     300
gggaccaagg tggaaatcaa acga                                            324

<210> SEQ ID NO 5
<211> LENGTH: 5
<212> TYPE: PRT
<213> ORGANISM: Human

<400> SEQUENCE: 5
```

```
Asn Ala Trp Met Ser
1               5

<210> SEQ ID NO 6
<211> LENGTH: 19
<212> TYPE: PRT
<213> ORGANISM: Human

<400> SEQUENCE: 6

Arg Ile Lys Ser Lys Thr Asp Gly Gly Thr Thr Asp Tyr Ala Ala Pro
1               5                   10                  15

Val Gln Gly

<210> SEQ ID NO 7
<211> LENGTH: 8
<212> TYPE: PRT
<213> ORGANISM: Human

<400> SEQUENCE: 7

Phe Gly Val Val Ser Phe Asp Tyr
1               5

<210> SEQ ID NO 8
<211> LENGTH: 11
<212> TYPE: PRT
<213> ORGANISM: Human

<400> SEQUENCE: 8

Arg Ala Ser Gln Ser Ile Ser Asp Tyr Leu Ser
1               5                   10

<210> SEQ ID NO 9
<211> LENGTH: 7
<212> TYPE: PRT
<213> ORGANISM: Human

<400> SEQUENCE: 9

Ala Ala Ser Asn Leu Lys Thr
1               5

<210> SEQ ID NO 10
<211> LENGTH: 9
<212> TYPE: PRT
<213> ORGANISM: Human

<400> SEQUENCE: 10

Gln Gln Ser Tyr Arg Ser Pro Trp Thr
1               5

<210> SEQ ID NO 11
<211> LENGTH: 104
<212> TYPE: PRT
<213> ORGANISM: Human

<400> SEQUENCE: 11

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
```

```
                    50                  55                  60
Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                     85                  90                  95

Tyr Cys Thr Thr Thr Thr Val Thr
                100

<210> SEQ ID NO 12
<211> LENGTH: 15
<212> TYPE: PRT
<213> ORGANISM: Human

<400> SEQUENCE: 12

Tyr Phe Asp Tyr Trp Gly Gln Gly Thr Leu Val Thr Val Ser Ser
  1               5                  10                  15

<210> SEQ ID NO 13
<211> LENGTH: 93
<212> TYPE: PRT
<213> ORGANISM: Human

<400> SEQUENCE: 13

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser
                 85                  90

<210> SEQ ID NO 14
<211> LENGTH: 13
<212> TYPE: PRT
<213> ORGANISM: Human

<400> SEQUENCE: 14

Trp Thr Phe Gly Gln Gly Thr Lys Val Glu Ile Lys Arg
  1               5                  10

<210> SEQ ID NO 15
<211> LENGTH: 1722
<212> TYPE: PRT
<213> ORGANISM: Human

<400> SEQUENCE: 15

Met Arg Thr Gly Trp Ala Thr Pro Arg Arg Pro Ala Gly Leu Leu Met
  1               5                  10                  15

Leu Leu Phe Trp Phe Phe Asp Leu Ala Glu Pro Ser Gly Arg Ala Ala
                 20                  25                  30

Asn Asp Pro Phe Thr Ile Val His Gly Asn Thr Gly Lys Cys Ile Lys
             35                  40                  45

Pro Val Tyr Gly Trp Ile Val Ala Asp Asp Cys Asp Glu Thr Glu Asp
         50                  55                  60
```

-continued

Lys Leu Trp Lys Trp Val Ser Gln His Arg Leu Phe His Leu His Ser
65                  70                  75                  80

Gln Lys Cys Leu Gly Leu Asp Ile Thr Lys Ser Val Asn Glu Leu Arg
            85                  90                  95

Met Phe Ser Cys Asp Ser Ser Ala Met Leu Trp Trp Lys Cys Glu His
            100                 105                 110

His Ser Leu Tyr Gly Ala Ala Arg Tyr Arg Leu Ala Leu Lys Asp Gly
            115                 120                 125

His Gly Thr Ala Ile Ser Asn Ala Ser Asp Val Trp Lys Lys Gly Gly
        130                 135                 140

Ser Glu Glu Ser Leu Cys Asp Gln Pro Tyr His Glu Ile Tyr Thr Arg
145                 150                 155                 160

Asp Gly Asn Ser Tyr Gly Arg Pro Cys Glu Phe Pro Phe Leu Ile Asp
                165                 170                 175

Gly Thr Trp His His Asp Cys Ile Leu Asp Glu Asp His Ser Gly Pro
            180                 185                 190

Trp Cys Ala Thr Thr Leu Asn Tyr Glu Tyr Asp Arg Lys Trp Gly Ile
            195                 200                 205

Cys Leu Lys Pro Glu Asn Gly Cys Glu Asp Asn Trp Glu Lys Asn Glu
210                 215                 220

Gln Phe Gly Ser Cys Tyr Gln Phe Asn Thr Gln Thr Ala Leu Ser Trp
225                 230                 235                 240

Lys Glu Ala Tyr Val Ser Cys Gln Asn Gln Gly Ala Asp Leu Leu Ser
                245                 250                 255

Ile Asn Ser Ala Ala Glu Leu Thr Tyr Leu Lys Glu Lys Glu Gly Ile
            260                 265                 270

Ala Lys Ile Phe Trp Ile Gly Leu Asn Gln Leu Tyr Ser Ala Arg Gly
        275                 280                 285

Trp Glu Trp Ser Asp His Lys Pro Leu Asn Phe Leu Asn Trp Asp Pro
    290                 295                 300

Asp Arg Pro Ser Ala Pro Thr Ile Gly Gly Ser Ser Cys Ala Arg Met
305                 310                 315                 320

Asp Ala Glu Ser Gly Leu Trp Gln Ser Phe Ser Cys Glu Ala Gln Leu
                325                 330                 335

Pro Tyr Val Cys Arg Lys Pro Leu Asn Asn Thr Val Glu Leu Thr Asp
            340                 345                 350

Val Trp Thr Tyr Ser Asp Thr Arg Cys Asp Ala Gly Trp Leu Pro Asn
        355                 360                 365

Asn Gly Phe Cys Tyr Leu Leu Val Asn Glu Ser Asn Ser Trp Asp Lys
    370                 375                 380

Ala His Ala Lys Cys Lys Ala Phe Ser Ser Asp Leu Ile Ser Ile His
385                 390                 395                 400

Ser Leu Ala Asp Val Glu Val Val Thr Lys Leu His Asn Glu Asp
                405                 410                 415

Ile Lys Glu Glu Val Trp Ile Gly Leu Lys Asn Ile Asn Ile Pro Thr
            420                 425                 430

Leu Phe Gln Trp Ser Asp Gly Thr Glu Val Thr Leu Thr Tyr Trp Asp
        435                 440                 445

Glu Asn Glu Pro Asn Val Pro Tyr Asn Lys Thr Pro Asn Cys Val Ser
    450                 455                 460

Tyr Leu Gly Glu Leu Gly Gln Trp Lys Val Gln Ser Cys Glu Glu Lys
465                 470                 475                 480

Leu Lys Tyr Val Cys Lys Arg Lys Gly Glu Lys Leu Asn Asp Ala Ser

```
                    485             490             495
Ser Asp Lys Met Cys Pro Pro Asp Glu Gly Trp Lys Arg His Gly Glu
            500             505             510

Thr Cys Tyr Lys Ile Tyr Glu Asp Glu Val Pro Phe Gly Thr Asn Cys
            515             520             525

Asn Leu Thr Ile Thr Ser Arg Phe Glu Gln Glu Tyr Leu Asn Asp Leu
            530             535             540

Met Lys Lys Tyr Asp Lys Ser Leu Arg Lys Tyr Phe Trp Thr Gly Leu
545             550             555             560

Arg Asp Val Asp Ser Cys Gly Glu Tyr Asn Trp Ala Thr Val Gly Gly
            565             570             575

Arg Arg Arg Ala Val Thr Phe Ser Asn Trp Asn Phe Leu Glu Pro Ala
            580             585             590

Ser Pro Gly Gly Cys Val Ala Met Ser Thr Gly Lys Ser Val Gly Lys
            595             600             605

Trp Glu Val Lys Asp Cys Arg Ser Phe Lys Ala Leu Ser Ile Cys Lys
            610             615             620

Lys Met Ser Gly Pro Leu Gly Pro Glu Glu Ala Ser Pro Lys Pro Asp
625             630             635             640

Asp Pro Cys Pro Glu Gly Trp Gln Ser Phe Pro Ala Ser Leu Ser Cys
            645             650             655

Tyr Lys Val Phe His Ala Glu Arg Ile Val Arg Lys Arg Asn Trp Glu
            660             665             670

Glu Ala Glu Arg Phe Cys Gln Ala Leu Gly Ala His Leu Ser Ser Phe
            675             680             685

Ser His Val Asp Glu Ile Lys Glu Phe Leu His Phe Leu Thr Asp Gln
            690             695             700

Phe Ser Gly Gln His Trp Leu Trp Ile Gly Leu Asn Lys Arg Ser Pro
705             710             715             720

Asp Leu Gln Gly Ser Trp Gln Trp Ser Asp Arg Thr Pro Val Ser Thr
            725             730             735

Ile Ile Met Pro Asn Glu Phe Gln Gln Asp Tyr Asp Ile Arg Asp Cys
            740             745             750

Ala Ala Val Lys Val Phe His Arg Pro Trp Arg Arg Gly Trp His Phe
            755             760             765

Tyr Asp Asp Arg Glu Phe Ile Tyr Leu Arg Pro Phe Ala Cys Asp Thr
            770             775             780

Lys Leu Glu Trp Val Cys Gln Ile Pro Lys Gly Arg Thr Pro Lys Thr
785             790             795             800

Pro Asp Trp Tyr Asn Pro Asp Arg Ala Gly Ile His Gly Pro Pro Leu
            805             810             815

Ile Ile Glu Gly Ser Glu Tyr Trp Phe Val Ala Asp Leu His Leu Asn
            820             825             830

Tyr Glu Glu Ala Val Leu Tyr Cys Ala Ser Asn His Ser Phe Leu Ala
            835             840             845

Thr Ile Thr Ser Phe Val Gly Leu Lys Ala Ile Lys Asn Lys Ile Ala
            850             855             860

Asn Ile Ser Gly Asp Gly Gln Lys Trp Trp Ile Arg Ile Ser Glu Trp
865             870             875             880

Pro Ile Asp Asp His Phe Thr Tyr Ser Arg Tyr Pro Trp His Arg Phe
            885             890             895

Pro Val Thr Phe Gly Glu Glu Cys Leu Tyr Met Ser Ala Lys Thr Trp
            900             905             910
```

-continued

Leu Ile Asp Leu Gly Lys Pro Thr Asp Cys Ser Thr Lys Leu Pro Phe
        915                 920                 925

Ile Cys Glu Lys Tyr Asn Val Ser Ser Leu Glu Lys Tyr Ser Pro Asp
        930                 935                 940

Ser Ala Ala Lys Val Gln Cys Ser Glu Gln Trp Ile Pro Phe Gln Asn
945                 950                 955                 960

Lys Cys Phe Leu Lys Ile Lys Pro Val Ser Leu Thr Phe Ser Gln Ala
            965                 970                 975

Ser Asp Thr Cys His Ser Tyr Gly Thr Leu Pro Ser Val Leu Ser
            980                 985                 990

Gln Ile Glu Gln Asp Phe Ile Thr Ser Leu Leu Pro Asp Met Glu Ala
        995                 1000                1005

Thr Leu Trp Ile Gly Leu Arg Trp Thr Ala Tyr Glu Lys Ile Asn
    1010                1015                1020

Lys Trp Thr Asp Asn Arg Glu Leu Thr Tyr Ser Asn Phe His Pro
    1025                1030                1035

Leu Leu Val Ser Gly Arg Leu Arg Ile Pro Glu Asn Phe Phe Glu
    1040                1045                1050

Glu Glu Ser Arg Tyr His Cys Ala Leu Ile Leu Asn Leu Gln Lys
    1055                1060                1065

Ser Pro Phe Thr Gly Thr Trp Asn Phe Thr Ser Cys Ser Glu Arg
    1070                1075                1080

His Phe Val Ser Leu Cys Gln Lys Tyr Ser Glu Val Lys Ser Arg
    1085                1090                1095

Gln Thr Leu Gln Asn Ala Ser Glu Thr Val Lys Tyr Leu Asn Asn
    1100                1105                1110

Leu Tyr Lys Ile Ile Pro Lys Thr Leu Thr Trp His Ser Ala Lys
    1115                1120                1125

Arg Glu Cys Leu Lys Ser Asn Met Gln Leu Val Ser Ile Thr Asp
    1130                1135                1140

Pro Tyr Gln Gln Ala Phe Leu Ser Val Gln Ala Leu Leu His Asn
    1145                1150                1155

Ser Ser Leu Trp Ile Gly Leu Phe Ser Gln Asp Asp Glu Leu Asn
    1160                1165                1170

Phe Gly Trp Ser Asp Gly Lys Arg Leu His Phe Ser Arg Trp Ala
    1175                1180                1185

Glu Thr Asn Gly Gln Leu Glu Asp Cys Val Val Leu Asp Thr Asp
    1190                1195                1200

Gly Phe Trp Lys Thr Val Asp Cys Asn Asp Asn Gln Pro Gly Ala
    1205                1210                1215

Ile Cys Tyr Tyr Ser Gly Asn Glu Thr Glu Lys Glu Val Lys Pro
    1220                1225                1230

Val Asp Ser Val Lys Cys Pro Ser Pro Val Leu Asn Thr Pro Trp
    1235                1240                1245

Ile Pro Phe Gln Asn Cys Cys Tyr Asn Phe Ile Ile Thr Lys Asn
    1250                1255                1260

Arg His Met Ala Thr Thr Gln Asp Glu Val His Thr Lys Cys Gln
    1265                1270                1275

Lys Leu Asn Pro Lys Ser His Ile Leu Ser Ile Arg Asp Glu Lys
    1280                1285                1290

Glu Asn Asn Phe Val Leu Glu Gln Leu Leu Tyr Phe Asn Tyr Met
    1295                1300                1305

-continued

Ala Ser Trp Val Met Leu Gly Ile Thr Tyr Arg Asn Lys Ser Leu
1310                1315                1320

Met Trp Phe Asp Lys Thr Pro Leu Ser Tyr Thr His Trp Arg Ala
1325                1330                1335

Gly Arg Pro Thr Ile Lys Asn Glu Lys Phe Leu Ala Gly Leu Ser
1340                1345                1350

Thr Asp Gly Phe Trp Asp Ile Gln Thr Phe Lys Val Ile Glu Glu
1355                1360                1365

Ala Val Tyr Phe His Gln His Ser Ile Leu Ala Cys Lys Ile Glu
1370                1375                1380

Met Val Asp Tyr Lys Glu Glu Tyr Asn Thr Thr Leu Pro Gln Phe
1385                1390                1395

Met Pro Tyr Glu Asp Gly Ile Tyr Ser Val Ile Gln Lys Lys Val
1400                1405                1410

Thr Trp Tyr Glu Ala Leu Asn Met Cys Ser Gln Ser Gly Gly His
1415                1420                1425

Leu Ala Ser Val His Asn Gln Asn Gly Gln Leu Phe Leu Glu Asp
1430                1435                1440

Ile Val Lys Arg Asp Gly Phe Pro Leu Trp Val Gly Leu Ser Ser
1445                1450                1455

His Asp Gly Ser Glu Ser Ser Phe Glu Trp Ser Asp Gly Ser Thr
1460                1465                1470

Phe Asp Tyr Ile Pro Trp Lys Gly Gln Thr Ser Pro Gly Asn Cys
1475                1480                1485

Val Leu Leu Asp Pro Lys Gly Thr Trp Lys His Glu Lys Cys Asn
1490                1495                1500

Ser Val Lys Asp Gly Ala Ile Cys Tyr Lys Pro Thr Lys Ser Lys
1505                1510                1515

Lys Leu Ser Arg Leu Thr Tyr Ser Ser Arg Cys Pro Ala Ala Lys
1520                1525                1530

Glu Asn Gly Ser Arg Trp Ile Gln Tyr Lys Gly His Cys Tyr Lys
1535                1540                1545

Ser Asp Gln Ala Leu His Ser Phe Ser Glu Ala Lys Lys Leu Cys
1550                1555                1560

Ser Lys His Asp His Ser Ala Thr Ile Val Ser Ile Lys Asp Glu
1565                1570                1575

Asp Glu Asn Lys Phe Val Ser Arg Leu Met Arg Glu Asn Asn Asn
1580                1585                1590

Ile Thr Met Arg Val Trp Leu Gly Leu Ser Gln His Ser Val Asp
1595                1600                1605

Gln Ser Trp Ser Trp Leu Asp Gly Ser Glu Val Thr Phe Val Lys
1610                1615                1620

Trp Glu Asn Lys Ser Lys Ser Gly Val Gly Arg Cys Ser Met Leu
1625                1630                1635

Ile Ala Ser Asn Glu Thr Trp Lys Lys Val Glu Cys Glu His Gly
1640                1645                1650

Phe Gly Arg Val Val Cys Lys Val Pro Leu Gly Pro Asp Tyr Thr
1655                1660                1665

Ala Ile Ala Ile Ile Val Ala Thr Leu Ser Ile Leu Val Leu Met
1670                1675                1680

Gly Gly Leu Ile Trp Phe Leu Phe Gln Arg His Arg Leu His Leu
1685                1690                1695

Ala Gly Phe Ser Ser Val Arg Tyr Ala Gln Gly Val Asn Glu Asp

```
                    1700              1705              1710
         Glu Ile Met Leu Pro Ser Phe His Asp
                    1715              1720
```

<210> SEQ ID NO 16
<211> LENGTH: 30
<212> TYPE: PRT
<213> ORGANISM: Human

<400> SEQUENCE: 16

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Tyr Ser
            20                  25                  30
```

<210> SEQ ID NO 17
<211> LENGTH: 14
<212> TYPE: PRT
<213> ORGANISM: Human

<400> SEQUENCE: 17

```
Trp Val Arg Gln Ala Pro Gly Lys Gly Leu Glu Trp Val Gly
1               5                   10
```

<210> SEQ ID NO 18
<211> LENGTH: 32
<212> TYPE: PRT
<213> ORGANISM: Human

<400> SEQUENCE: 18

```
Arg Phe Thr Ile Ser Arg Asp Asp Ser Lys Asn Thr Leu Tyr Leu Gln
1               5                   10                  15

Met Asn Ser Leu Lys Thr Glu Asp Thr Ala Val Tyr Tyr Cys Thr Ile
            20                  25                  30
```

<210> SEQ ID NO 19
<211> LENGTH: 11
<212> TYPE: PRT
<213> ORGANISM: Human

<400> SEQUENCE: 19

```
Trp Gly Gln Gly Thr Leu Val Thr Val Ser Ser
1               5                   10
```

<210> SEQ ID NO 20
<211> LENGTH: 23
<212> TYPE: PRT
<213> ORGANISM: Human

<400> SEQUENCE: 20

```
Asp Val Gln Met Thr Gln Ser Pro Ser Ser Leu Ser Ala Ser Val Gly
1               5                   10                  15

Asp Arg Val Thr Ile Thr Cys
            20
```

<210> SEQ ID NO 21
<211> LENGTH: 15
<212> TYPE: PRT
<213> ORGANISM: Human

<400> SEQUENCE: 21

```
Trp Tyr Gln Gln Arg Pro Gly Lys Ala Pro Asn Leu Leu Ile Tyr
1               5                   10                  15
```

<210> SEQ ID NO 22
<211> LENGTH: 32
<212> TYPE: PRT
<213> ORGANISM: Human

<400> SEQUENCE: 22

Gly Val Pro Ser Arg Phe Ser Gly Ser Gly Thr Asp Phe Thr
1               5                   10                  15

Leu Thr Ile Ser Thr Leu Gln Pro Glu Asp Phe Ala Thr Tyr Tyr Cys
            20                  25                  30

<210> SEQ ID NO 23
<211> LENGTH: 11
<212> TYPE: PRT
<213> ORGANISM: Human

<400> SEQUENCE: 23

Phe Gly Gln Gly Thr Lys Val Glu Ile Lys Arg
1               5                   10

<210> SEQ ID NO 24
<211> LENGTH: 10
<212> TYPE: PRT
<213> ORGANISM: Human

<400> SEQUENCE: 24

Trp Glu Val Lys Asp Cys Arg Ser Phe Lys
1               5                   10

<210> SEQ ID NO 25
<211> LENGTH: 12
<212> TYPE: PRT
<213> ORGANISM: Human

<400> SEQUENCE: 25

Pro Ala Ser Leu Ser Cys Tyr Lys Val Phe His Ala
1               5                   10

<210> SEQ ID NO 26
<211> LENGTH: 20
<212> TYPE: PRT
<213> ORGANISM: Human

<400> SEQUENCE: 26

Pro Trp Arg Arg Gly Trp His Phe Tyr Asp Asp Arg Glu Phe Ile Tyr
1               5                   10                  15

Leu Arg Pro Phe
            20

<210> SEQ ID NO 27
<211> LENGTH: 19
<212> TYPE: PRT
<213> ORGANISM: Human

<400> SEQUENCE: 27

Asp Asp His Phe Thr Tyr Ser Arg Tyr Pro Trp His Arg Phe Pro Val
1               5                   10                  15

Thr Phe Gly

<210> SEQ ID NO 28
<211> LENGTH: 12
<212> TYPE: PRT

<213> ORGANISM: Human

<400> SEQUENCE: 28

```
Arg Glu Leu Thr Tyr Ser Asn Phe His Pro Leu Leu
1               5                   10
```

<210> SEQ ID NO 29
<211> LENGTH: 17
<212> TYPE: PRT
<213> ORGANISM: Human

<400> SEQUENCE: 29

```
Phe Thr Ser Cys Ser Glu Arg His Phe Val Ser Leu Cys Gln Lys Tyr
1               5                   10                  15

Ser
```

<210> SEQ ID NO 30
<211> LENGTH: 12
<212> TYPE: PRT
<213> ORGANISM: Human

<400> SEQUENCE: 30

```
Thr Val Lys Tyr Leu Asn Asn Leu Tyr Lys Ile Ile
1               5                   10
```

<210> SEQ ID NO 31
<211> LENGTH: 11
<212> TYPE: PRT
<213> ORGANISM: Human

<400> SEQUENCE: 31

```
Glu Ala Val Tyr Phe His Gln His Ser Ile Leu
1               5                   10
```

<210> SEQ ID NO 32
<211> LENGTH: 11
<212> TYPE: PRT
<213> ORGANISM: Human

<400> SEQUENCE: 32

```
Lys Lys Leu Ser Arg Leu Thr Tyr Ser Ser Cys
1               5                   10
```

<210> SEQ ID NO 33
<211> LENGTH: 20
<212> TYPE: PRT
<213> ORGANISM: Human

<400> SEQUENCE: 33

```
Asn Gly Ser Arg Trp Ile Gln Tyr Lys Gly His Cys Tyr Lys Ser Asp
1               5                   10                  15

Gln Ala Leu His
            20
```

<210> SEQ ID NO 34
<211> LENGTH: 25
<212> TYPE: PRT
<213> ORGANISM: Human

<400> SEQUENCE: 34

```
Ile Ser Glu Trp Pro Ile Asp Asp His Phe Thr Tyr Ser Arg Tyr Pro
1               5                   10                  15

Trp His Arg Phe Pro Val Thr Phe Gly
```

```
<210> SEQ ID NO 35
<211> LENGTH: 20
<212> TYPE: PRT
<213> ORGANISM: Human

<400> SEQUENCE: 35

Gln Thr Leu Gln Asn Ala Ser Glu Thr Val Lys Tyr Leu Asn Asn Leu
1               5                   10                  15

Tyr Lys Ile Ile
            20

<210> SEQ ID NO 36
<211> LENGTH: 10
<212> TYPE: PRT
<213> ORGANISM: Human

<400> SEQUENCE: 36

Asp Asp His Phe Thr Tyr Ser Arg Tyr Pro
1               5                   10

<210> SEQ ID NO 37
<211> LENGTH: 15
<212> TYPE: PRT
<213> ORGANISM: Human

<400> SEQUENCE: 37

Phe Thr Ser Cys Ser Glu Arg His Phe Val Ser Leu Cys Gln Lys
1               5                   10                  15
```